United States Patent
Suga et al.

(10) Patent No.: US 11,142,495 B2
(45) Date of Patent: Oct. 12, 2021

(54) COMPOSITION AND METHOD FOR MANUFACTURING DEVICE USING SAME

(71) Applicant: TOYO GOSEI CO., LTD., Chiba (JP)

(72) Inventors: Yusuke Suga, Chiba (JP); Satoshi Enomoto, Chiba (JP)

(73) Assignee: TOYO GOSEI CO., LTD., Chiba (JP)

( * ) Notice: Subject to any disclaimer, the term of this patent is extended or adjusted under 35 U.S.C. 154(b) by 260 days.

(21) Appl. No.: 16/339,525

(22) PCT Filed: Oct. 13, 2017

(86) PCT No.: PCT/JP2017/037266
§ 371 (c)(1),
(2) Date: Apr. 4, 2019

(87) PCT Pub. No.: WO2018/074382
PCT Pub. Date: Apr. 26, 2018

(65) Prior Publication Data
US 2020/0048191 A1 Feb. 13, 2020

(30) Foreign Application Priority Data

Oct. 17, 2016 (JP) .............................. JP2016-203780
Feb. 24, 2017 (JP) .............................. JP2017-033234

(51) Int. Cl.
| C07C 381/12 | (2006.01) |
| C07C 43/315 | (2006.01) |
| G03F 7/004  | (2006.01) |
| G03F 7/039  | (2006.01) |
| G03F 7/38   | (2006.01) |

(52) U.S. Cl.
CPC .......... *C07C 381/12* (2013.01); *C07C 43/315* (2013.01); *G03F 7/0045* (2013.01); *G03F 7/039* (2013.01); *G03F 7/38* (2013.01)

(58) Field of Classification Search
CPC .................................................. C07C 381/12
See application file for complete search history.

(56) References Cited

U.S. PATENT DOCUMENTS

| 5,968,713 A | 10/1999 | Nozaki et al. |
| 6,013,416 A | 1/2000  | Nozaki et al. |
| 6,200,725 B1 | 3/2001 | Takechi et al. |
| 2001/0003640 A1 | 6/2001 | Takechi et al. |
| 2002/0027646 A1* | 3/2002 | Sugita ............... G03F 7/70375 355/53 |
| 2002/0039701 A1* | 4/2002 | Takeda ................. C08F 220/30 430/270.1 |
| 2002/0061464 A1* | 5/2002 | Aoai ..................... G03F 7/0046 430/270.1 |
| 2008/0102407 A1* | 5/2008 | Ohsawa ................ G03F 7/0382 430/286.1 |
| 2009/0197987 A1* | 8/2009 | Hayoz ................... G03F 7/0045 522/17 |
| 2010/0297542 A1 | 11/2010 | Hayoz et al. |
| 2014/0363769 A1 | 12/2014 | Namai et al. |
| 2016/0004160 A1 | 1/2016 | Tagawa et al. |
| 2016/0357103 A1 | 12/2016 | Nagahara et al. |
| 2018/0231892 A1 | 8/2018 | Tagawa et al. |

FOREIGN PATENT DOCUMENTS

| JP | H09-90637 A | 4/1997 |
| JP | 2015-124240 A | 7/2015 |
| JP | 2015172741 A | 10/2015 |
| JP | 5881093 B1 | 3/2016 |
| TW | 200925144 A | 6/2009 |
| WO | 2016133073 A1 | 8/2016 |

OTHER PUBLICATIONS

Chinese Office Action dated Sep. 27, 2020, in connection with corresponding CN Application No. 201780063876.2 (14 pp., including machine-generated English translation).

Taiwanese Office Action dated Aug. 28, 2020, in connection with corresponding TW Application No. 106135350 (6 pp., including machine-generated English translation).

Translation of International Search Report dated Nov. 21, 2017 of corresponding International Application No. PCT/JP2017/037266; 1 page.

Marucci, Gabriella, et al., Synthesis and Antimuscarinic Activity of Derivatives of 2-Substituted-1,3-Dioxolanes,Medicinal Chemistry Research, 2005, vol. 14, No. 5, pp. 274-296, 23 pgs.

Seiji Nagahara et al., "Challenge toward breakage of RLS trade-off for EUV lithography by Photosensitized Chemically Amplified ResistTM (PSCARTM) with flood exposure", Proc. of SPIE vol. 9776 977607, 23 pgs.

* cited by examiner

Primary Examiner — Anca Eoff
(74) Attorney, Agent, or Firm — Maier & Maier, PLLC

(57) ABSTRACT

An onium salt and a composition having high sensitivity and excellent pattern characteristics such as LWR, which is preferably used for a resist composition for a lithography process using two active energy rays of a first active energy ray such as an electron beam or an extreme ultraviolet and a second active energy ray such as UV.

15 Claims, No Drawings

COMPOSITION AND METHOD FOR MANUFACTURING DEVICE USING SAME

CROSS-REFERENCE TO RELATED APPLICATIONS

The instant application is a National Stage of PCT/JP2017/027266 filed on Oct. 13, 2017, and claims benefit of foreign priority to the applications JP 2016-203780 filed on Oct. 17, 2016 and JP 2017-033234 filed on Feb. 24, 2017.

TECHNICAL FIELD

An embodiment of the present invention relates to a composition. Another embodiment of the present invention relates to a method of manufacturing a device using the composition.

BACKGROUND ART

In recent years, by making full use of a photolithography technique using a photoresist, manufacturing of a display device such as a liquid crystal display (LCD) and an organic EL display (OLED), and formation of semiconductor elements are active. As an active energy ray, i-line having a wavelength of 365 nm, and light such as h-line (405 nm) and g-line (436 nm) having a longer wavelength than i-line are widely used for the packaging of the electronic component and the electronic product.

Since a device integration has developed, a demand for miniaturization of lithography technology has been increased, a light having a very short wavelength such as KrF excimer laser (wavelength 248 nm), ArF excimer laser (wavelength 193 nm), extreme ultraviolet (EUV, wavelength 13.5 nm) and an electron beam (EB) tends to be used for exposure. Since the lithography techniques using these short wavelength lights, especially EUV or electron beam, can allow manufacturing by single patterning, a demand for a resist composition having high sensitivity to EUV, the electron beam or the like may further increase in the future.

Due to shortening the wavelength of the exposure light source, it is required for the resist composition to improve the sensitivity to the exposure light source and a resolution property of lithography which can reproduce a pattern of fine size. A chemically amplified resist is known as a resist composition satisfying such requirements (Patent Literature 1).

However, since conventional chemically amplified resist compositions for EUV, electron beam or the like have low EUV or electron beam absorption, it is difficult to simultaneously satisfy the required characteristics in sensitivity, resolution and pattern performance. Especially, it is difficult to overcome throughput reduction, collapse of resist pattern and deterioration of line width roughness (LWR) of a line pattern. The throughput reduction is caused by low sensitivity due to small absorption. The collapse and deterioration occur as resolution width of resist becomes finer.

For the above problems, to improve the throughput of EUV or electron beam lithography, a photosensitized chemically amplified resist composition to generate an acid and a sensitizer by lithography using a first active energy ray such as EUV, electron beam or the like, and then to be irradiated with a second active energy ray such as visible light, ultraviolet ray or the like has been proposed (Patent Literature 2 to 3 and Non-Patent Literature 1).

CITATION LIST

Patent Literature

Patent Literature 1: JPH9-90637
Patent Literature 2: JP5881093
Patent Literature 3: JP2015-172741

Non-Patent Literature

Non-Patent Literature 1: Proc. of SPIE Vol. 9776 977607

SUMMARY OF INVENTION

Technical Problem

When the resist reaction is promoted by the second active energy ray using the photosensitized chemically amplified resist composition utilizing a photosensitizing reaction, due to a photoinduced electron transfer reaction occuring between the sensitizer (electron donor) and the photoacid generator (electron acceptor). Therefore, an acid may be generated by the electron transfer reaction of a few nm in some cases. Even when an acid-diffusion controller is contained in the resist composition, unintended diffusion of the generated acid may cause without reacting with the acid-diffusion controller. As a result, pattern deterioration such as deterioration of LWR may occur. On the other hand, when a large amount of acid-diffusion controller is added to suppress the pattern deterioration, in the process of generating a photosensitizer by the acid generated by the first active energy ray, the amount of photosensitizer produced is less, so that the sensitization reaction hardly occurs. For example, even if it is irradiated with a large amount of energy of 1 J/cm$^2$, only a slight promoting effect of the resist reaction is obtained.

In view of such circumstances, it is an object according to some aspects of the present invention to provide a photoacid generator and a composition which is excellent in pattern characteristics such as sensitivity and LWR. More specifically, it is an object to provide an onium salt which is most suitable as a photoacid generator used for irradiating with a particle beam or an electromagnetic wave or the like. It is another object to provide a composition containing the onium salt and a specific resin whose solubility in a developing solution changes by an acid. It is another object to provide an onium salt which is most suitable as a photoacid generator used for irradiating with a second active energy ray such as ultraviolet ray, visible light or the like after irradiating with a first active energy ray such as a particle beam, an electromagnetic wave or the like. It is another object to provide a composition containing the onium salt and a specific resin whose solubility in a developing solution changes by an acid. Furthermore, it is an object according to some embodiments of the present invention to provide a photoacid generator containing the onium salt and a composition containing the photoacid generator. It is another object to provide a method of manufacturing a device using the composition.

Solution to Problem

As a result of extensive studies to solve the above-mentioned problems, the inventors of the present invention have found that a onium salt having a specific structure do not have significant absorption in the second active energy ray such as a ultraviolet ray, a visible light or the like, and the onium salt is converted into a ketone derivative having absorption in the second active energy ray by changing its structure by an acid generated by the first active energy ray such as a particle beam, an electromagnetic wave or the like. Then, the inventors completed some aspects of the present invention.

Compared with the resist composition described in Patent Literature 3 that uses the photosensitizing reaction generated between the electron donor and the electron acceptor, the acid is generated by irradiation with the second active energy ray with high efficiency by the photoacid generator containing an onium salt in the resist composition, so that it has been found that it has high sensitivity and excellent pattern characteristics such as LWR and the like.

An embodiment of the present invention for solving the above-problems is an onium salt represented by any one selected from a following general formula (1), a following general formula (2), a following general formula (11), and a following general formula (12).

[Chem. 1]

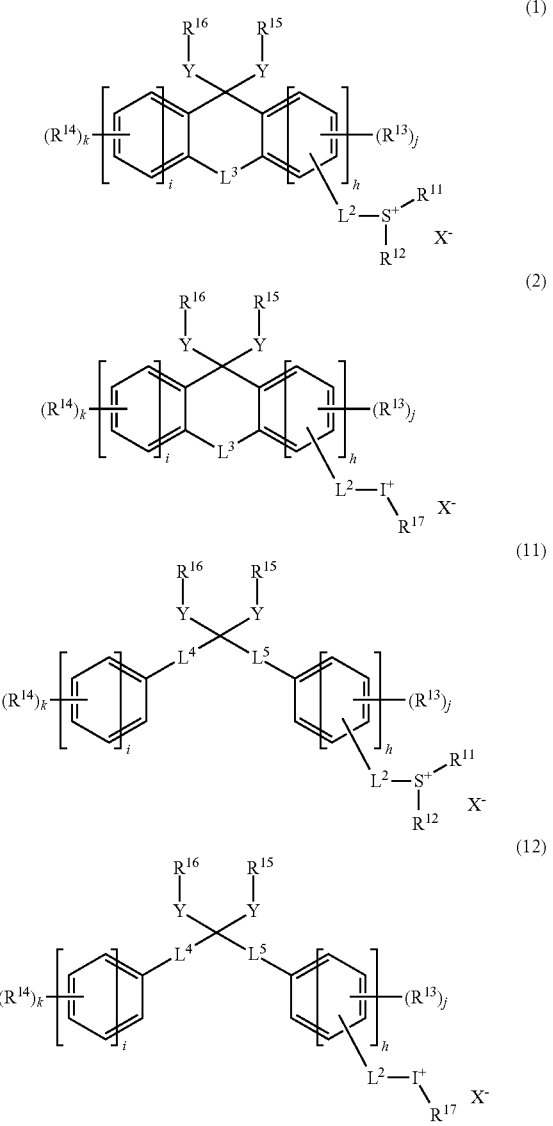

In the general formula (1), each of $R^{11}$ and $R^{12}$ is any one independently selected from the group consisting of: a linear, branched or cyclic alkyl group which may have a substituent, the alkyl group having 1 to 12 carbon atoms; a linear, branched or cyclic alkenyl group which may have a substituent, the alkenyl group having 1 to 12 carbon atoms; an aryl group which may have a substituent, the aryl group having 6 to 14 carbon atoms; and a heteroaryl group which may have a substituent, the heteroaryl group having 4 to 12 carbon atoms.

Any two or more of $R^{11}$, $R^{12}$ and an aryl group bonded to a sulfonium group may be bonded each other directly with a single bond or through any one selected from the group consisting of an oxygen atom, a sulfur atom, a nitrogen atom-containing group and a methylene group to form a ring structure with a sulfur atom ($S^+$) bonded to $R^{11}$, $R^{12}$ and the aryl group bonded to the sulfonium group.

At least one methylene group in $R^{11}$ and $R^{12}$ may be substituted with a divalent hetero atom-containing group.

Each of $R^{13}$ and $R^{14}$ is any one independently selected from the group consisting of an alkyl group, a hydroxy group, a mercapto group, an alkoxy group, an alkylcarbonyl group, an arylcarbonyl group, an alkoxycarbonyl group, an aryloxycarbonyl group, an arylsulfanylcarbonyl group, an arylsulfanyl group, an alkylsulfanyl group, an aryl group, a heteroaryl group, an aryloxy group, an alkylsulfinyl group, an arylsulfinyl group, an alkylsulfonyl group, an arylsulfonyl group, an arylsulfonyl group, a (meth)acryloyloxy group, a hydroxy(poly)alkyleneoxy group, an amino group, a cyano group, a nitro group and a halogen atom, wherein $R^{13}$ and $R^{14}$ have 1 to 12 carbon atoms when $R^{13}$ and $R^{14}$ has a carbon atom, and these groups may have a substituent.

Each of $R^{15}$ and $R^{16}$ is any one independently selected from the group consisting of: a linear, branched or cyclic alkyl group which may have a substituent, the alkyl group having 1 to 12 carbon atoms; a linear, branched or cyclic alkenyl group which may have a substituent, the alkenyl group having 1 to 12 carbon atoms; an aryl group which may have a substituent, the aryl group having 6 to 14 carbon atoms; and a heteroaryl group which may have a substituent, the heteroaryl group having 4 to 12 carbon atoms.

$R^{15}$ and $R^{16}$ may be bonded each other directly with a single bond or through any one selected from the group consisting of an oxygen atom, a sulfur atom and an alkylene group to form a ring structure.

At least one methylene group in $R^{15}$ and $R^{16}$ may be substituted with a divalent hetero atom-containing group.

A quaternary carbon atom directly bonded to two of Y and two aryl groups directly bonded to the quaternary carbon atom form a 5-membered ring structure with a direct bond between the two aryl groups directly bonded to the quaternary carbon atom or a 6-membered ring structure with a bond through one atom. $L^3$ is any one selected from the group consisting of a direct bond, a methylene group, a sulfur atom, a nitrogen atom-containing group, and an oxygen atom.

$L^2$ is any one selected from the group consisting of: a direct bond; a branched or cyclic alkylene group having 1 to 12 carbon atoms; an alkenylene group having 1 to 12 carbon atoms; an arylene group having 6 to 14 carbon atoms; a heteroarylene group having 4 to 12 carbon atoms; and a group in which these groups are bonded through an oxygen atom, a sulfur atom or a nitrogen atom-containing group.

Y is an oxygen atom or a sulfur atom.

Each of h and i is independently an integer of 1 to 3.

j is an integer of 0 to 4 when h is 1, 0 to 6 when h is 2, and 0 to 8 when h is 3.

k is an integer of 0 to 5 when i is 1, 0 to 7 when h is 2, and 0 to 9 when h is 3.

$X^-$ is a monovalent counter anion.

In the general formula (2), each of $R^{13}$ to $R^{16}$, $L^2$, $L^3$, Y, h to k and $X^-$ is independently selected from a same option as each of $R^{13}$ to $R^{16}$, $L^2$, $L^3$, Y, h to k and $X^-$ of the formula (1).

$R^{17}$ is any one selected from the group consisting of an aryl group which may have a substituent and a heteroaryl group which may have a substituent.

$R^{17}$ and an aryl group bonded to an iodonium group may be bonded each other to form a ring structure with an iodine atom bonded to $R^{17}$ and the aryl group bonded to the iodonium group.

In the general formula (11), each of $R^{11}$ to $R^{16}$, $L^2$, Y, h to k and $X^-$ is independently selected from a same option as each of $R^{11}$ to $R^{16}$, $L^2$, Y, h to k and $X^-$ in the formula (1).

Each of $L^4$ and $L^5$ is any one independently selected from the group consisting of a direct bond, an alkenylene group having 2 carbon atoms, an alkynylene group having 2 carbon atoms and a carbonyl group.

In the general formula (12), each of $R^{13}$ to $R^{17}$, $L^2$, Y, h to k and $X^-$ is independently selected from a same option as each of $R^{13}$ to $R^{17}$, $L^2$, Y, h to k and $X^-$ in the formula (2).

Each of $L^4$ and $L^5$ is any one independently selected from the group consisting of a direct bond, an alkenylene group having 2 carbon atoms, an alkynylene group having 2 carbon atoms and a carbonyl group.

Furthermore, an embodiment of the present invention is a sulfonium salt represented by a following general formula (6). In the following, a monocation is described, but a polycation may be used.

[Chem. 2]

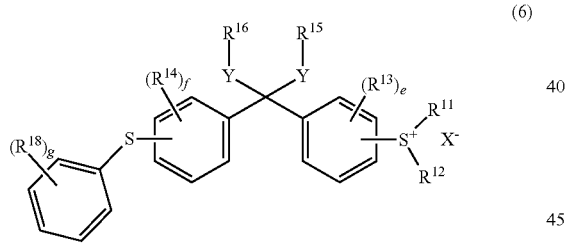

(6)

In the general formula (6), each of $R^{11}$ to $R^{16}$, $X^-$ and Y is independently selected from a same option as each of $R^{11}$ to $R^{16}$, $X^-$ and Y of the general formula (1).

$R^{18}$ is any one selected from the group consisting of an alkyl group, a hydroxy group, a mercapto group, an alkoxy group, an alkylcarbonyl group, an arylcarbonyl group, an alkoxycarbonyl group, an aryloxycarbonyl group, an arylsulfanylcarbonyl group, an arylsulfanyl group, an alkylsulfanyl group, an aryl group, a heteroaryl group, an aryloxy group, an alkylsulfinyl group, an arylsulfinyl group, an alkylsulfonyl group, an arylsulfonyl group, an arylsulfonyl group, a (meth)acryloyloxy group, a hydroxy(poly) alkyleneoxy group, an amino group, a cyano group, a nitro group and a halogen atom, wherein $R^{18}$ preferably has 1 to 12 carbon atoms when $R^{18}$ has a carbon atom, and these groups may have a substituent.

e is an integer of 0 to 4, f is an integer of 0 to 4, and g is an integer of 0 to 5.

Another embodiment of the present invention is a photoacid generator (A) containing at least an onium salt represented by any one selected from the general formula (1), the general formula (2), the general formula (11) and the general formula (12). The photoacid generator (A) generates an acid by exposure.

An embodiment of the present invention for solving the above-problems is a composition containing the photoacid generator and an acid reactive compound.

Preferably, the composition further contains an acid-diffusion controller.

Preferably, the acid reactive compound is a resin (B) whose solubility in a developing solution changes by an acid, wherein the resin (B) has at least one of units represented by following formulas (3a) to (3d). The onium salt contained in the photoacid generator (A) is described as a monocation above, but it may also be a polycation.

[Chem. 3]

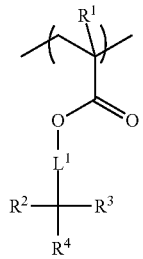

(3a)

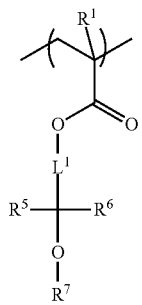

(3b)

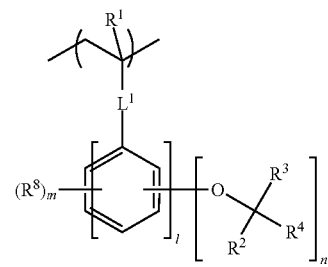

(3c)

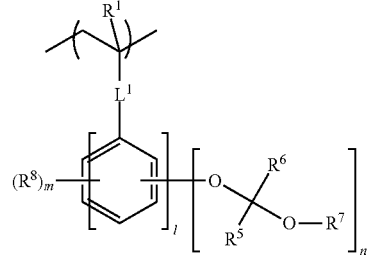

(3d)

In the formulas (3a) to (3d), $R^1$ is any one selected from the group consisting of a hydrogen atom, an alkyl group and a halogenated alkyl group.

Each of $R^2$ and $R^3$ is independently a linear, branched or cyclic alkyl group.

$R^4$ is a linear, branched or cyclic alkyl group which may have a substituent.

Two or more of $R^2$, $R^3$ and $R^4$ may be bonded each other directly with a single bond or through any one selected from the group consisting of a methylene group to form a ring structure.

Each of $R^5$ and $R^6$ is any one independently selected from the group consisting of a hydrogen atom, and a linear, branched or cyclic alkyl group.

$R^7$ is a linear, branched or cyclic alkyl group which may have a substituent.

Two or more of $R^5$, $R^6$ and $R^7$ may be bonded each other directly with a single bond or through any one selected from the group consisting of a methylene group to form a ring structure.

$L^1$ is any one selected from the group consisting of: a direct bond; a carbonyloxy group; a carbonylamino group; a linear, branched or cyclic alkylenecarbonyloxy group which may have a substituent; and a linear, branched or cyclic alkylenecarbonylamino group which may have a substituent.

Each of $R^8$ is any one independently selected from the group consisting of an alkyl group, a hydroxy group, an alkoxy group, an alkylcarbonyl group, an alkylsulfanyl group, an alkylsulfinyl group, an alkylsulfonyl group, an amino group, a cyano group, a nitro group and a halogen atom.

l is an integer of 1 to 2.

m is an integer of 0 to 4 when l is 1, and an integer of 0 to 6 when l is 2.

n is an integer of 1 to 5 when l is 1, and an integer of 1 to 7 when l is 2.

m+n is 1 to 5 when l is 1, and 1 to 7 when l is 2.

Furthermore, another embodiment of the present invention is a method of manufacturing a device, including:

formimg a resist film by applying the composition to a substrate;

irradiating the resist film with a first active energy ray;

irradiating a resist film after iraddiating with the first active energy ray, with a second active energy ray; and obtaining a pattern by developing a resist film after irradiating with the second active energy ray.

Advantageous Effects of Invention

Some embodiments of the present invention provide a composition containing an onium salt, as an acid generator, having high sensitivity and excellent pattern characteristics such as LWR and the like, and the composition is preferably used as a resist composition for a lithography process using a first active energy ray such as a particle beam, an electromagnetic wave or the like, and a second active energy ray such as an ultraviolet ray, a visible light or the like. In addition, some embodiments of the present invention provide a resist composition which is highly sensitive to the first active energy ray such as the particle beam or the electromagnetic wave, particularly the electron beam, the extreme ultraviolet or the like, and a method of manufacturing a device using the same.

Description of Embodiments

Hereinafter, the present invention will be specifically described, but the present invention is not limited thereto.

<1>Onium Salt and Photoacid Generator

An onium salt according to an embodiment of the present invention is represented by any one selected from the general formula (1), the general formula (2), the general formula (11) and the general formula (12). The photoacid generator, hereinafter also referred to as "photoacid generator (A)", contains at least one of the onium salt. The onium salt is a sulfonium salt or an iodonium salt.

Since the onium salt according to an embodiment of the present invention has a specific structure such as an acetal, a thioacetal or the like, the onium salt does not have significant absorption in the second active energy ray such as an ultraviolet ray, a visible light or the like. On the other hand, without impairing a function as a photoacid generator, the acetal or the thioacetal of the onium salt is deprotected to be converted into a ketone derivative with an acid generated by the first active energy ray such as a particle beam, an electromagnetic wave or the like. The ketone derivative has absorption in the first active energy ray and the second active energy ray. Since the ketone derivative is generated in an exposed portion irradiated with the first active energy ray in the resist film, further, an acid generation amount in the exposed portion irradiated with the first active energy ray can be increased by irradiating with the second active energy ray.

In the general formula (1), each of $R^{11}$ and $R^{12}$ is preferably any one independently selected from the group consisting of: a linear, branched or cyclic alkyl group which may have a substituent, the alkyl group having 1 to 12 carbon atoms; a linear, branched or cyclic alkenyl group which may have a substituent, the alkenyl group having 1 to 12 carbon atoms; an aryl group which may have a substituent, the aryl group having 6 to 14 carbon atoms; and a heteroaryl group which may have a substituent, the heteroaryl group having 4 to 12 carbon atoms.

Specific examples of the linear, branched or cyclic alkyl group having 1 to 12 carbon atoms for each of $R^{11}$ and $R^{12}$ include alkyl groups such as a methyl group, an ethyl group, an n-propyl group, an n-butyl group, an isopropyl group, a t-butyl group, a cyclopropyl group, a cyclobutyl group, a cyclopentyl group, a cyclohexyl group, an adamantan-1-yl group, an adamantan-2-yl group, a norbornan-1-yl group, a norbornan-2-yl group and the like.

In the alkyl group of $R^{11}$ and $R^{12}$, its skelton may include, instead of at least one methylene group, any one divalent heteroatom-containing group selected from the group consisting of —O—, —CO—, —COO—, —OCO—, —O—CO—O—, —NHCO—, —CONH—, —NH—CO—O—, —O—CO—NH—, —NH—, —N(R)—, —N(Ar)—, —S—, —SO— and —SO$_2$—. However, the sulfur atom (S$^+$) of the sulfonium group is preferably not bonded directly to the hetero atom-containing group but is bonded to the divalent hydrocarbon group. R and Ar will be described later.

Examples of the alkenyl group of $R^{11}$ and $R^{12}$ include groups in which at least one carbon-carbon single bond of the alkyl group is replaced with a carbon-carbon double bond.

Specific examples of the aryl group of $R^{11}$ and $R^{12}$ which may have a substituent, the aryl group having 6 to 14 carbon atoms, include: a monocyclic aromatic hydrocarbon group; a condensed polycyclic aromatic hydrocarbon group in which at least two of the monocyclic aromatic hydrocarbons are condensed; and the like. These aryl groups may have a substituent.

Examples of the monocyclic aromatic hydrocarbon group include groups having a skeleton such as benzene.

Examples of the condensed polycyclic aromatic hydrocarbon group include groups having a skeleton such as indene, naphthalene, azulene, anthracene, phenanthrene and the like.

Examples of the heteroaryl group of $R^{11}$ and $R^{12}$ which may have a substituent, the heteroaryl group having 4 to 12 carbon atoms, include groups having, in its skeleton, at least one selected from the group consisting of an oxygen atom, a nitrogen atom and a sulfur atom instead of at least one carbon atom of the aryl group.

Examples of the heteroaryl group include: a monocyclic aromatic heterocyclic group; and a condensed polycyclic aromatic heterocyclic group in which at least one of the monocyclic aromatic heterocyclic ring is condensed with the aromatic hydrocarbon group, an aliphatic heterocyclic group or the like. These aromatic heterocyclic groups may have a substituent.

Examples of the monocyclic aromatic heterocyclic group include groups having a skeleton such as furan, pyrrole, imidazole, pyran, pyridine, pyrimidine, pyrazine and the like.

Examples of the condensed polycyclic aromatic heterocyclic group include groups having a skeleton such as indole, purine, quinoline, isoquinoline, chromene, phenoxazine, xanthene, acridine, phenazine, carbazole and the like.

Examples of the substituent which each of $R^{11}$ and $R^{12}$ may have, hereinafter also referred to as "first substituent", include a hydroxy group, a cyano group, a mercapto group, a carboxy group, a carbonyl group, an alkoxy group (—OR), an acyl group (—COR), an alkoxycarbonyl group (—COOR), an aryl group (—Ar), an aryloxy group (—OAr), an amino group, an alkylamino group (—NHR), a dialkylamino group (—N(R)$_2$), an arylamino group (—NHAr), a diarylamino group (—N(Ar)$_2$), an N-alkyl-N-arylamino group (—NRAr), a phosphino group, a silyl group, a halogen atom, a trialkylsilyl group (—Si—(R)$_3$), a silyl group in which at least one alkyl group of the trialkylsilyl group is substituted with Ar, an alkylsulfanyl group (—SR), an arylsulfanyl group (—SAr); and the like, but it is not limited thereto. R and Ar will be described later.

Furthermore, the first substituent may be a group in which the above group has a polymerizable group such as a (meth)acryloyl group.

Any two or more of $R^{11}$, $R^{12}$ and an aryl group bonded to a sulfonium group may be bonded each other directly with a single bond or through any one selected from the group consisting of an oxygen atom, a sulfur atom, a nitrogen atom-containing group and a methylene group to form a ring structure with a sulfur atom (S$^+$) of a sulfonium group bonded to $R^{11}$, $R^{12}$ and the aryl group bonded to the sulfonium group. The sulfur atom (S$^+$) of the sulfonium group is preferably not bonded directly to the hetero atom-containing group but is bonded to the divalent hydrocarbon group.

Examples of "the nitrogen atom-containing group" include a divalent group containing a nitrogen atom such as an aminodiyl group (—NH—), an alkylaminodiyl group (—NR—), an arylaminodiyl group (—NAr—) and the like. R and Ar will be described later.

In the formula (1), the aryl group bonded to the sulfonium group is a moiety indicated by the arrow below.

[Chem. 4]

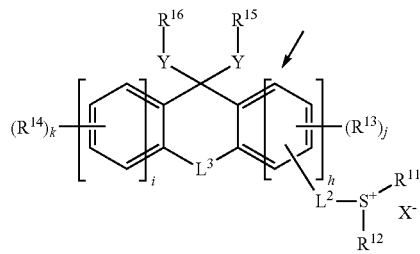

R in the first substituent or the like is preferably an alkyl group having 1 or more carbon atoms. In addition, R is more preferably an alkyl group having 20 or less carbon atoms. Specific examples of the alkyl group having 1 or more carbon atoms include: a linear alkyl group such as a methyl group, an ethyl group, an n-propyl group, an n-butyl group, an n-pentyl group, an n-hexyl group, an n-octyl group, an n-decyl group and the like; a branched alkyl group such as an isopropyl group, an isobutyl group, a tert-butyl group, an isopentyl group, a tert-pentyl group, a 2-ethylhexyl group and the like; an alicyclic alkyl group such as a cyclopropyl group, a cyclobutyl group, a cyclopentyl group, a cyclohexyl group, an adamantan-1-yl group, an adamantan-2-yl group, a norbornan-1-yl group, a norbornan-2-yl group and the like; a silyl group-substituted alkyl group in which one hydrogen of these groups is substituted with a trialkylsilyl group such as a trimethylsilyl group, a triethylsilyl group, a dimethylethylsilyl group or the like; an alkyl group in which at least one hydrogen of these groups is substituted with a cyano group, a fluoro group or the like; and the like.

Ar in the first substituent or the like is preferably an aryl group or a heteroaryl group. The heteroaryl group is an aryl group having at least one hetero atom in the ring structure. Specific examples of Ar preferably include groups having 20 or less carbon atoms such as a phenyl group, a biphenyl group, a terphenyl group, a quaterphenyl group, a naphthyl group, a anthryl group, a phenanthrenyl group, a pentalenyl group, an indenyl group, an indacenyl group, an acenaphthyl group, a fluorenyl group, a heptarenyl group, a naphthacenyl group, a pyrenyl group, a chrysenyl group, a tetracenyl group, a furanyl group, a thienyl group, a pyranyl group, a sulfanyl pyranyl group, a pyrrolyl group, an imidazoyl group, an oxazolyl group, a thiazolyl group, a pyrazoyl group, a pyridyl group, an isobenzofuranyl group, a benzofuranyl group, an isochromenyl group, a chromenyl group, an indolyl group, an isoindolyl group, a benzimidazoyl group, a xanthenyl group, an aquadinyl group, a carbazoyl group and the like.

When $R^{11}$ and $R^{12}$ have the first substituent and the onium salt is a low molecular weight compound, a number of carbon atoms of $R^{11}$ and $R^{12}$, including a number of carbon atoms of the first substituent, is preferably 1 to 20.

The onium salt according to an embodiment of the present invention may be: a polymer component bonded to a part of a polymer as a unit of a resin, that is, as a unit containing an onium salt structure; or a polymer component contained as a polymer unit. When the onium salt is the polymer component, the first substituent may be a main chain of the polymer. When the first substituent of $R^{11}$ and $R^{12}$ is the main chain of the polymer, the number of carbon atoms of $R^{11}$ and $R^{12}$ excludes a number of carbon atoms of the polymer main chain. When the onium salt according to an embodiment of the present invention is the polymer component, a weight average molecular weight of the whole polymer component is preferably controlled to be 2000 to 200000.

In the present invention, the low molecular weight compound is a compound having a weight average molecular weight of less than 2000, and the polymer component is a component having a weight average molecular weight of 2000 or more.

From a viewpoint of improvement of stability, $R^{11}$ and $R^{12}$ are preferably the aryl group.

Each of $R^{13}$ and $R^{14}$ is independently an alkyl group, a hydroxy group, a mercapto group, an alkoxy group, an alkylcarbonyl group, an arylcarbonyl group, an alkoxycarbonyl group, an aryloxycarbonyl group, an arylsulfanylcarbonyl group, an arylsulfanyl group, an alkylsulfanyl group, an aryl group, a heteroaryl group, an aryloxy group, an alkylsulfinyl group, an arylsulfinyl group, an alkylsulfonyl group, an arylsulfonyl group, an arylsulfonyl group, a (meth)acryloyloxy group, a hydroxy(poly)alkyleneoxy group, an amino group, a cyano group, a nitro group and a halogen atom, wherein $R^{13}$ and $R^{14}$ preferably have 1 to 12 carbon atoms when $R^{13}$ and $R^{14}$ have a carbon atom, and these groups may have a substituent, hereinafter also referred to as "second substituent".

The alkyl group of $R^{13}$ and $R^{14}$ may be a linear, branched or cyclic, and specific examples thereof include the same alkyl group as R of the first substituent. Examples of the aryl group and heteroaryl group of $R^{13}$ and $R^{14}$ include the same aryl group and heteroaryl group as Ar of the first substituent of $R^{11}$ and $R^{12}$. Examples of the alkoxy group of $R^{13}$ and $R^{14}$ include the same alkoxy group (—OR) as the first substituent.

Examples of the hydroxy(poly)alkyleneoxy group of $R^{13}$ and $R^{14}$ include a polyethyleneoxy group, a polypropyleneoxy group and the like.

Examples of the halogen atom for $R^{13}$ and $R^{14}$ include a fluorine atom, a chlorine atom, an iodine atom and the like.

The alkyl group of $R^{13}$ and $R^{14}$ may have, instead of at least one methylene group, the same group as the hetero atom-containing group of $R^{11}$ and $R^{12}$ in its skeleton. However, the alkyl group of $R^{13}$ and $R^{14}$ preferably does not have a continuous bonding of heteroatoms such as —O—O—, —S—S—, —O—S— and the like.

Examples of the second substituent which $R^{13}$ and $R^{14}$ may have include the same substituent as the first substituent.

When $R^{13}$ and $R^{14}$ have the second substituent and the onium salt is a low molecular weight compound, a number of carbon atoms of $R^{13}$ and $R^{14}$, including a number of carbon atoms of the second substituent, is preferably 1 to 12.

When the second substituent of $R^{13}$ and $R^{14}$ is a polymer main chain, the number of carbon atoms of $R^{13}$ and $R^{14}$ excludes a number of the polymer main chain.

$R^{14}$ is preferably the alkyl group. In addition, examples of $R^{14}$ also preferably include an electron donating group such as an aryl group, an alkoxy group, an alkylsulfanyl group, an aryloxy group, an arylsulfanyl group, an amino group, an alkylamino group and the like, wherein $R^{14}$ is in the position of ortho or para to the quaternary carbon bonded to an arylene having Y and $R^{14}$. These are preferable from a viewpoint of improving an absorbance at 365 nm.

$R^{15}$ and $R^{16}$ are preferably selected from the group consisting of: a linear, branched or cyclic alkyl group which may have a substituent, the alkyl group having 1 to 12 carbon atoms; a linear, branched or cyclic alkenyl group which may have a substituent, the alkenyl group having 1 to 12 carbon atoms; an aryl group which may have a substituent, the aryl group having 6 to 14 carbon atoms; and a heteroaryl group which may have a substituent, the heteroaryl group having 4 to 12 carbon atoms. These are selected from a same option as each of $R^{11}$ and $R^{12}$ above.

Examples of the substituent of $R^{15}$ and $R^{16}$, hereinafter also referred to as "third substituent", include the same substituent as the first substituent.

$R^{15}$ and $R^{16}$ may be bonded each other directly with a single bond or through any one selected from the group consisting of an oxygen atom, a sulfur atom and an alkylene group to form a ring structure.

From a viewpoint of synthesis, $R^{15}$ and $R^{16}$ are preferably same.

A quaternary carbon atom directly bonded to two of Y and two aryl groups directly bonded to the quaternary carbon atom, indicated as $Ar^a$ and $Ar^b$ by arrows in the following formula, form a 5-membered ring structure with a direct bond between the two aryl groups directly bonded to the quaternary carbon atom, or a 6-membered ring structure with a bond through one atom.

$L^3$ is any one selected from the group consisting of a direct bond, a methylene group, a sulfur atom, a nitrogen atom-containing group and an oxygen atom. Examples of the nitrogen atom-containing group of $L^3$ include the same groups as the divalent nitrogen atom-containing group.

[Chem. 5]

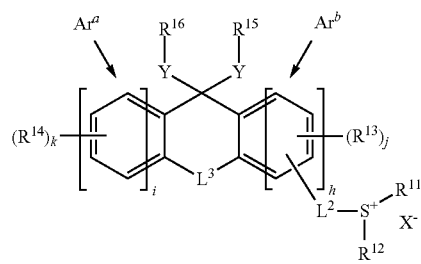

Here, when the 5-membered ring structure is formed with a direct bond between the aryl groups, the onium salt has a structure represented by the following formula.

[Chem. 6]

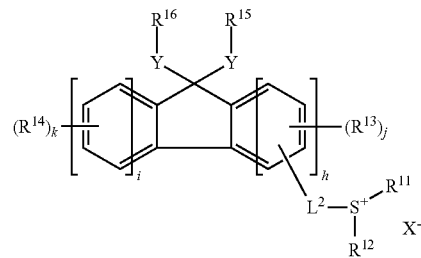

When the 6-membered ring structure with a bond through one atom, for example, the onium salt may have a structure represented by the following formula.

[Chem. 7]

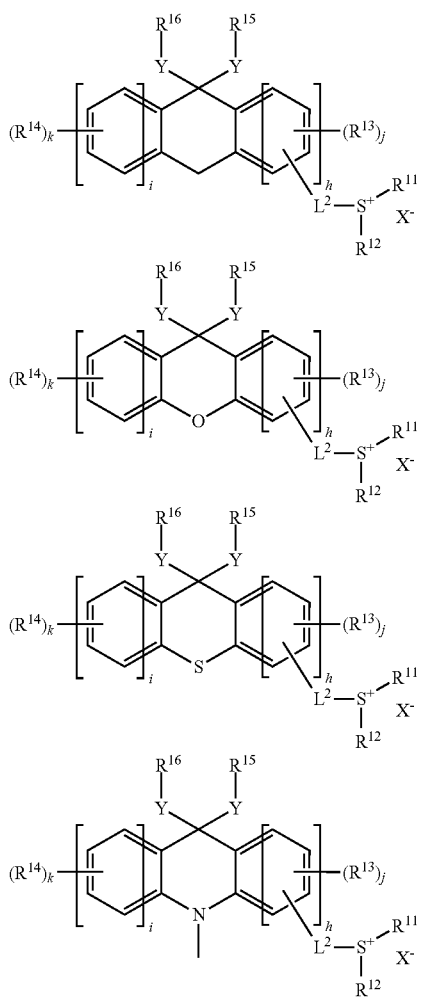

$L^2$ is preferably any one selected from the group consisting of: a linear, branched or cyclic alkylene group having 1 to 12 carbon atoms; an alkenylene group having 1 to 12 carbon atoms; an arylene group having 6 to 12 carbon atoms; a heteroarylene group having 4 to 12 carbon atoms; and a group in which these groups are bonded through an oxygen atom, a sulfur atom or a nitrogen atom-containing group. Examples of each of the alkylene group, the alkenylene group, arylene group and the heteroarylene group of $L^2$ include groups in which each of the alkyl group, the alkenyl group, the aryl group, and the heteroaryl group of $R^{11}$ become divalent. Examples of the nitrogen atom-containing group of $L^2$ include the same nitrogen atom-containing group as $R^{11}$.

In the above general formula (1), from a viewpoint of ease of synthesis, each of k and j is preferably 0 to 3, more preferably 0 to 2, independently.

Each of $R^{13}$ to $R^{16}$, $X^-$, Y, $L^2$, $L^3$ and h to k is any one independently selected from a same option as $R^{13}$ to $R^{16}$, $X^-$, Y, $L^2$, $L^3$ and h to k of the formula (1).

$R^{17}$ is preferably any one selected from the group consisting of: an aryl group which may have a substituent, the aryl group having 6 to 12 carbon atoms; and a heteroaryl group which may have a substituent, the heteroaryl group having 4 to 12 carbon atoms. $R^{17}$ and an aryl group bonded to an iodonium group may be bonded each other to form a ring structure with an iodine atom bonded to $R^{17}$ and the aryl group bonded the iodonium group. The aryl group and the heteroaryl group of $R^{17}$ are selected from a same option as each of the aryl and heteroaryl groups of $R^{11}$ above. Examples of the substituent of $R^{17}$ include the same substituent as the first substituent.

In the general formula (2), the aryl group bonded to the iodonium group is a moiety indicated by the arrow below.

[Chem. 8]

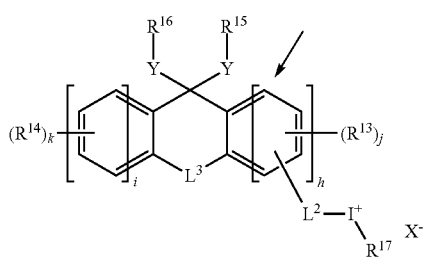

A quaternary carbon atom directly bonded to two of Y and two aryl groups directly bonded to the quaternary carbon atom form a 5-membered ring structure with a direct bond between the two aryl groups directly bonded to the quaternary carbon atom, or a 6-membered ring structure with a bond through $L^3$.

Each of $R^{11}$ to $R^{16}$, $L^2$, Y, h to k and $X^-$ is any one independently selected from a same option as each of $R^{11}$ to $R^{16}$, $L^2$, Y, h to k and $X^-$ in the formula (1).

Each of $L^4$ and $L^5$ is any one independently selected from the group consisting of a direct bond, an alkenylene group having 2 carbon atoms, an alkynylene group having 2 carbon atoms and a carbonyl group. That is, a quaternary carbon atom directly bonded to two of Y and two aryl groups may be bonded directly, or bonded through the alkenylene group having 2 carbon atoms or the alkynylene group having 2 carbon atoms, but the onium salt has a structure having at least one bond through the alkenylene group having 2 carbon atoms or the alkynylene group having 2 carbon atoms.

In the general formula (11), the aryl group bonded to the sulfonium group is a moiety indicated by the arrow below.

[Chem. 9]

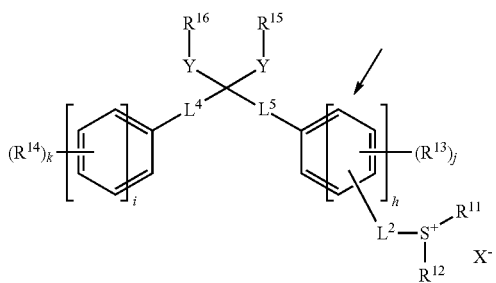

In the general formula (12), each of $R^{13}$ to $R^{17}$, $L^2$, Y, h to k and $X^-$ is independently selected from a same option as each of $R^{13}$ to $R^{17}$, $L^2$, Y, h to k and $X^-$ in the formula (2).

Each of $L^4$ and $L^5$ is any one independently selected from the group consisting of a direct bond, an alkenylene group having 2 carbon atoms, an alkynylene group having 2 carbon atoms and a carbonyl group. That is, a quaternary carbon atom directly bonded to two of Y and the two aryl groups may be bonded directly, or bonded through the alkenylene group having 2 carbon atoms or the alkynylene group having 2 carbon atoms, but the onium salt has a structure having at least one bond through the alkenylene group having 2 carbon atoms or the alkynylene group having 2 carbon atoms.

In the general formula (12), the aryl group bonded to the iodonium group is a moiety indicated by the arrow below.

[Chem. 10]

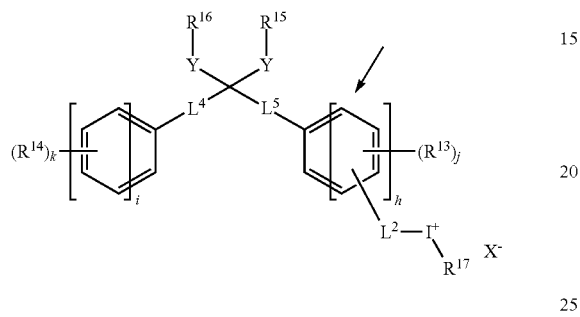

In the general formula (1), (2), (11) or (12), Y is an oxygen atom or a sulfur atom.

Each of h and i is independently an integer of 1 to 3.

j is an integer of 0 to 4 when h is 1, 0 to 6 when h is 2, and 0 to 8 when h is 3.

k is an integer of 0 to 5 when i is 1, 0 to 7 when h is 2, and 0 to 9 when h is 3.

For example, when i and/or h is 2 in the formula (1) or (2), the onium salt has a naphthalene ring. The naphthalene ring may be bonded to the quaternary carbon bonded to Y at any position of 1- to 8-position.

For example, when i and/or h is 3 in the above formula (1), (2), (11) or (12), the onium salt has at least one of an anthracene ring, a phenanthrene ring and a naphthacene ring. Also in this case, the phenanthrene ring and the naphthacene ring may be bonded to the quaternary carbon bonded to Y at any position of 1- to 10-position.

In some embodiments of the present invention, examples of the onium salt include those having a sulfonium cation and an iodonium cation described below. However, some aspects of the present invention are not limited thereto.

[Chem. 11]

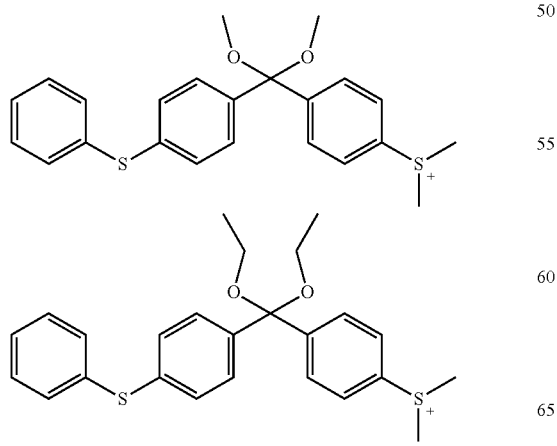

-continued

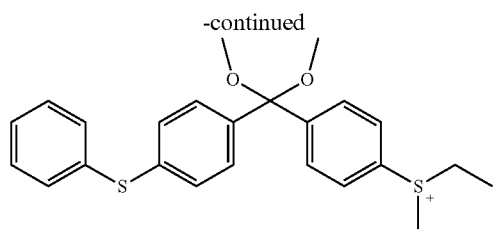

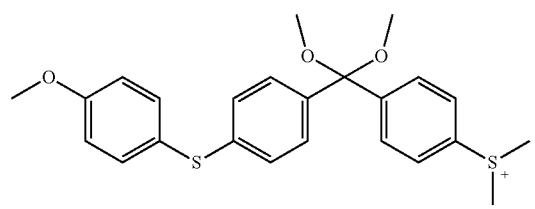

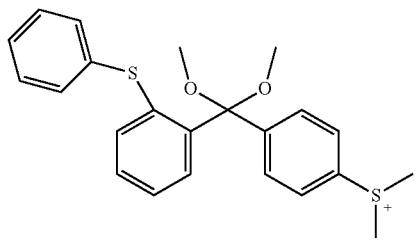

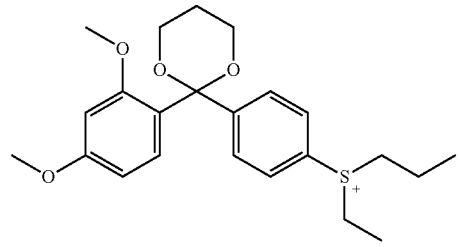

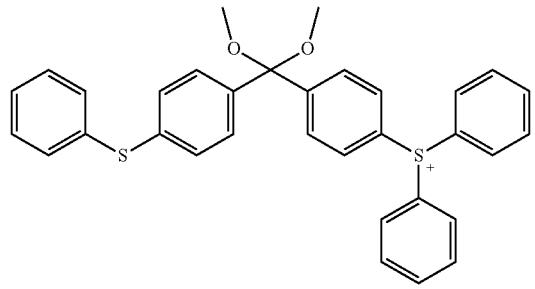

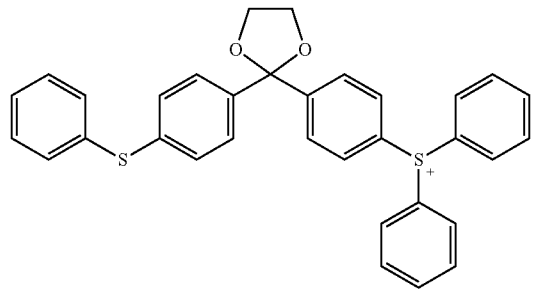

17
-continued
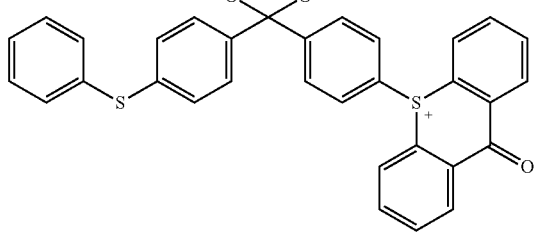
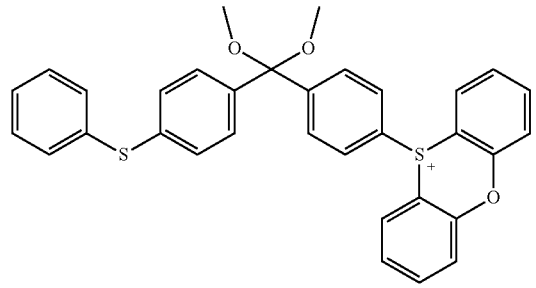
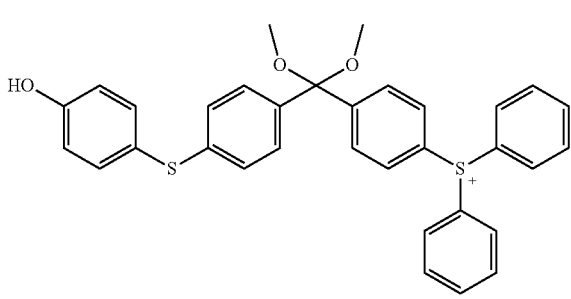
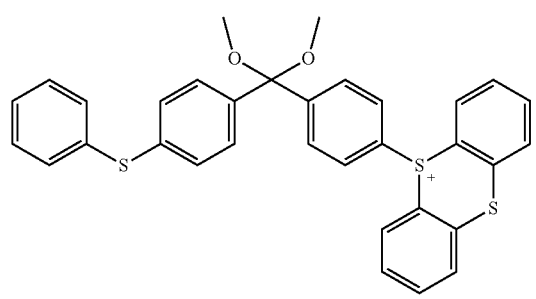
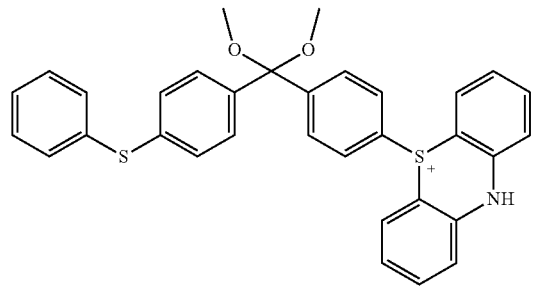
18
-continued
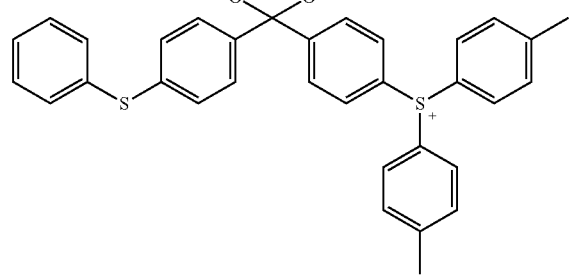
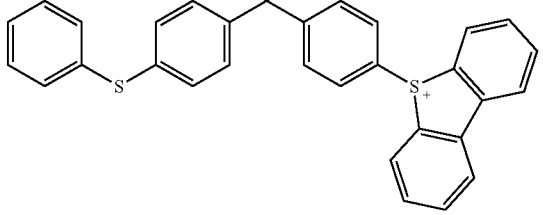
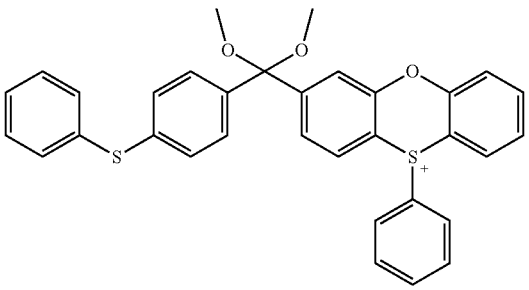
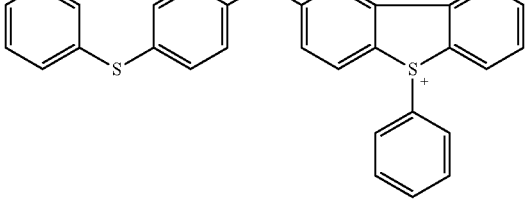
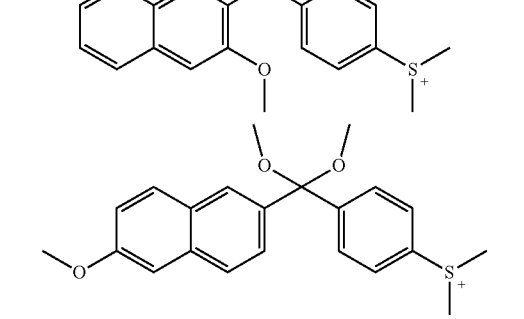
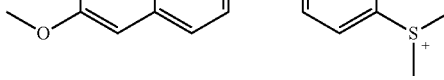

[Chem. 12]
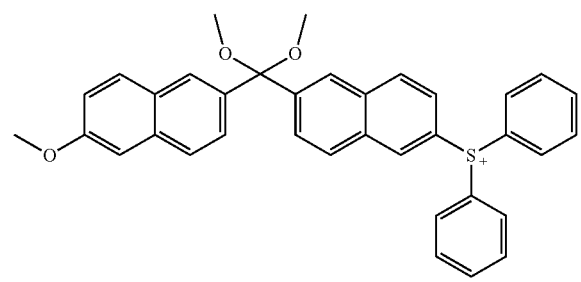
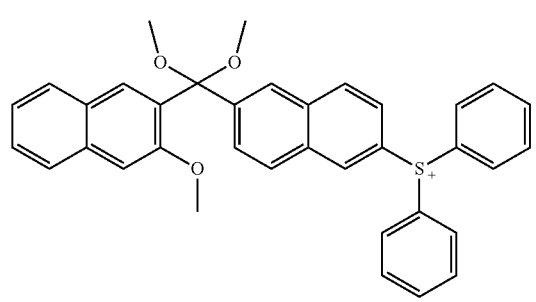
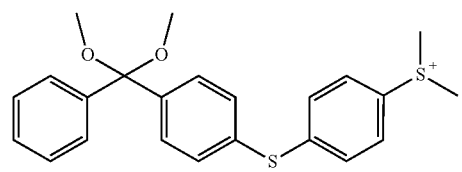
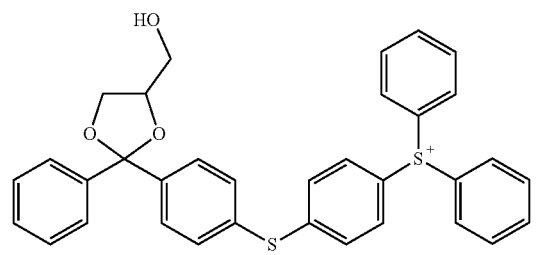
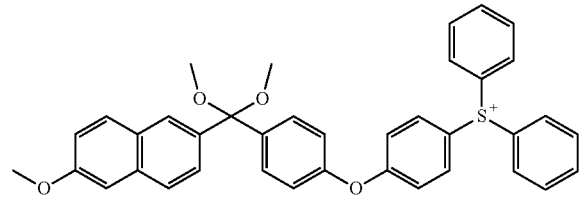
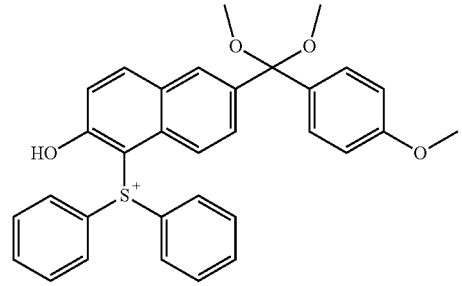
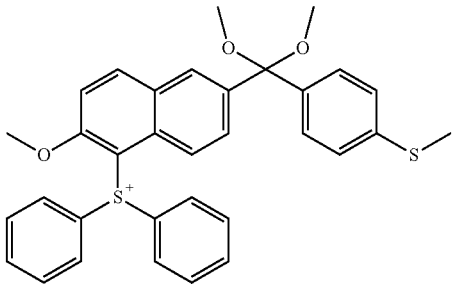
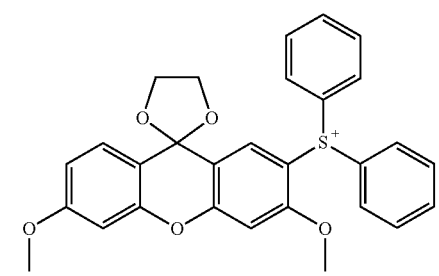
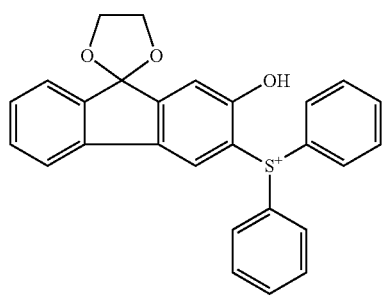
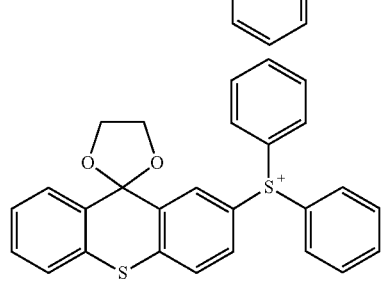
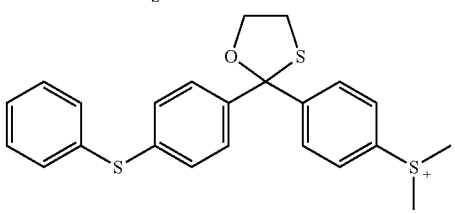
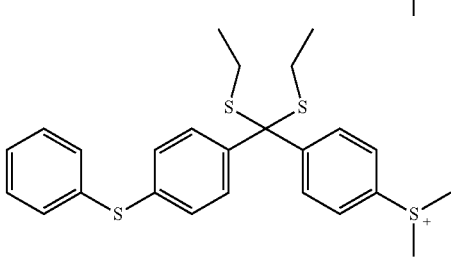

-continued
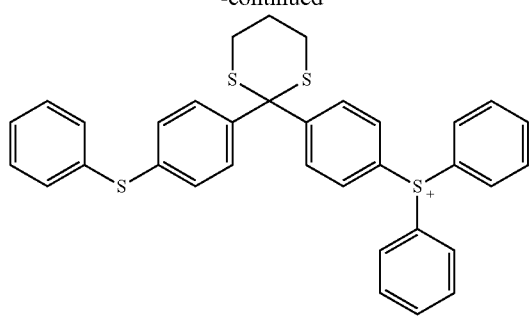
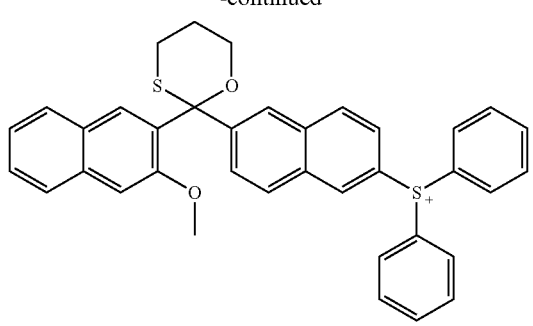
[Chem. 13]
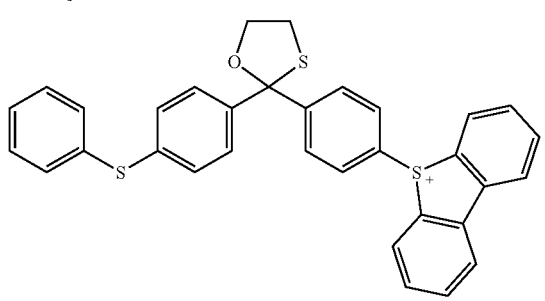
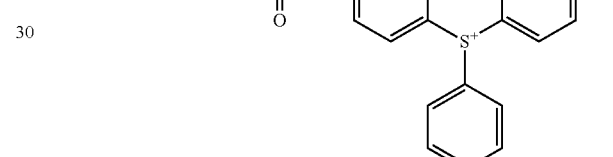
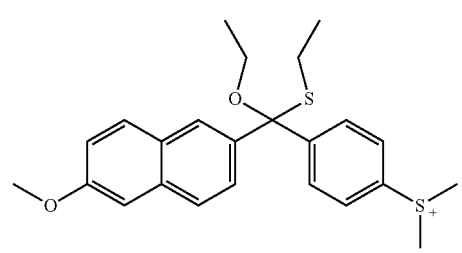
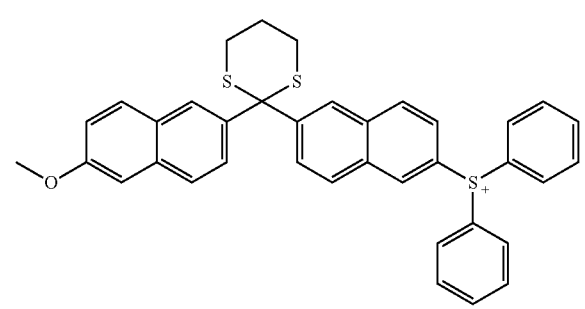
[Chem. 14]
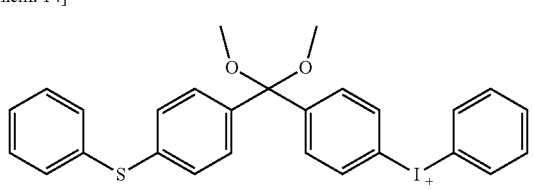

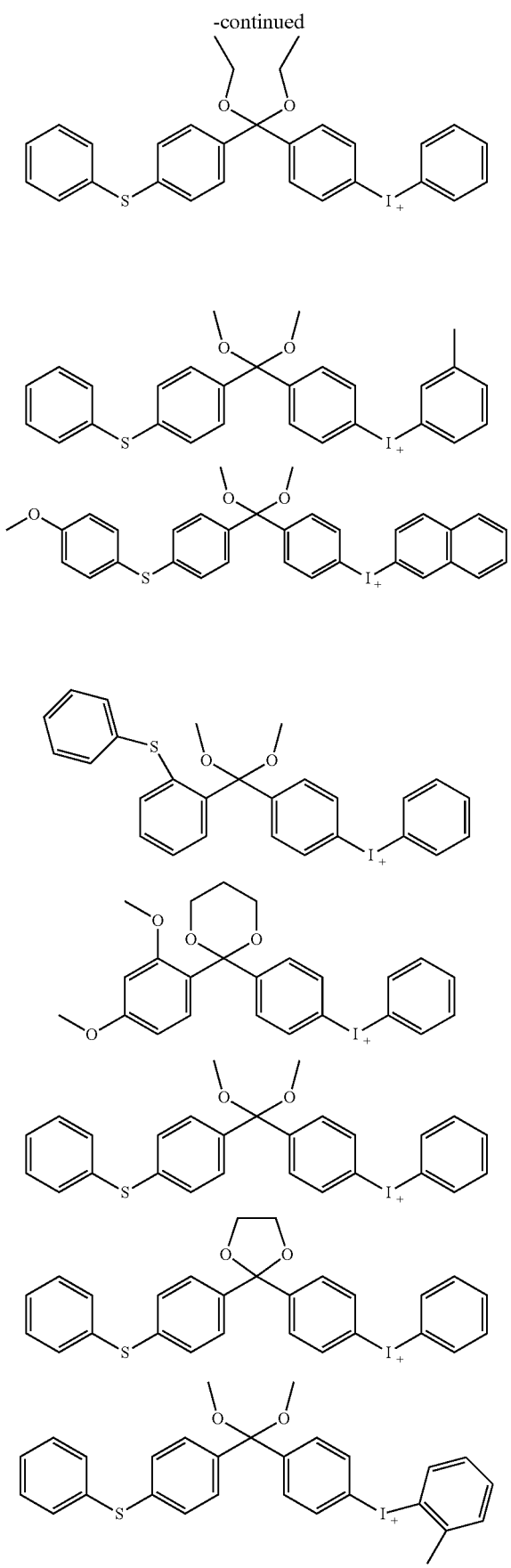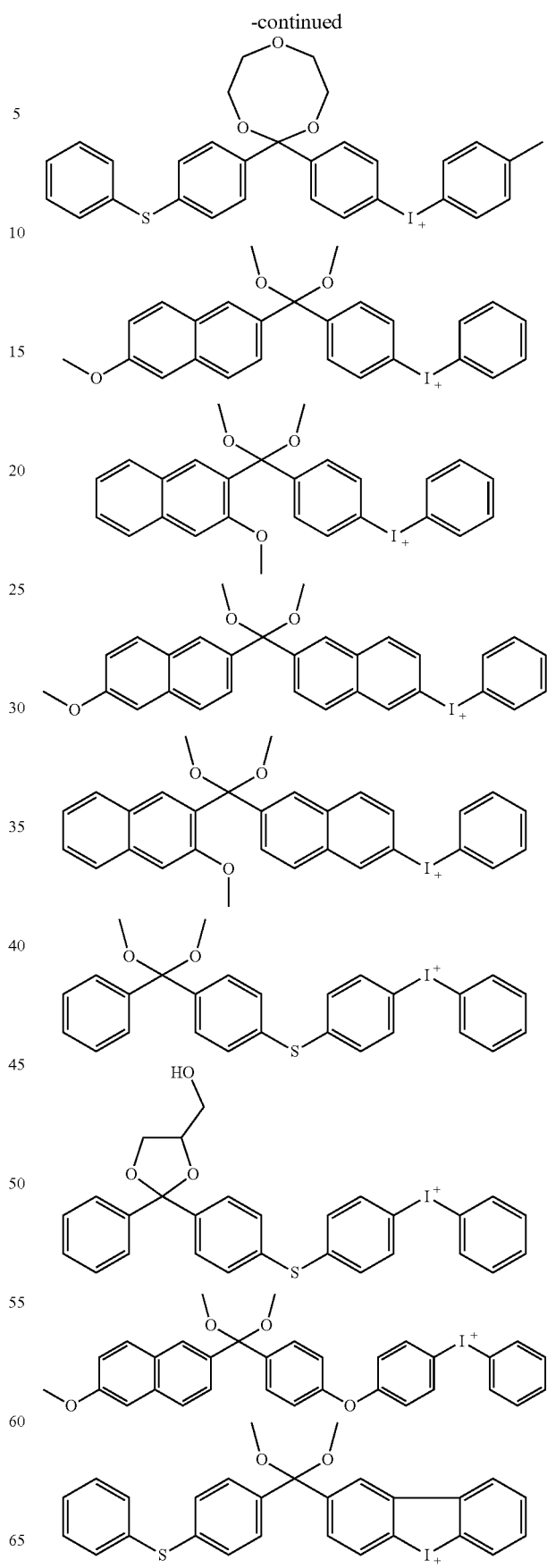

-continued

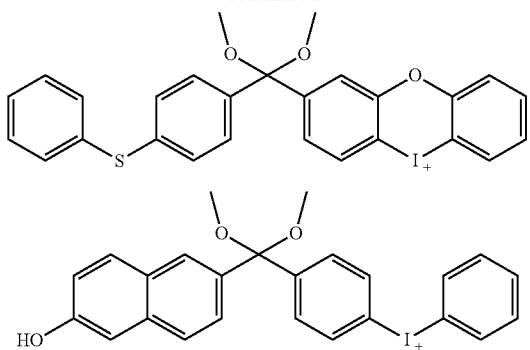

[Chem. 15]

-continued

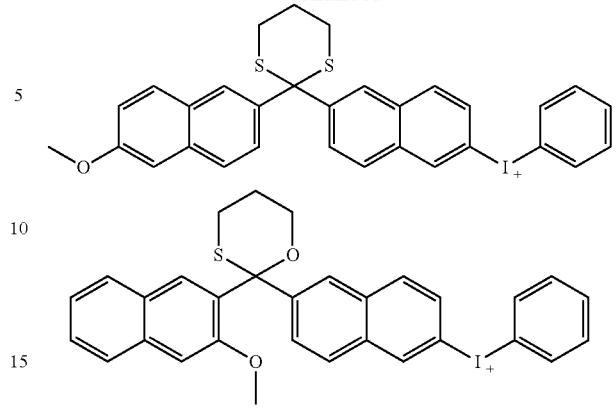

An embodiment of the present invention is preferably a sulfonium salt represented by a following formula (6).

[Chem. 16]

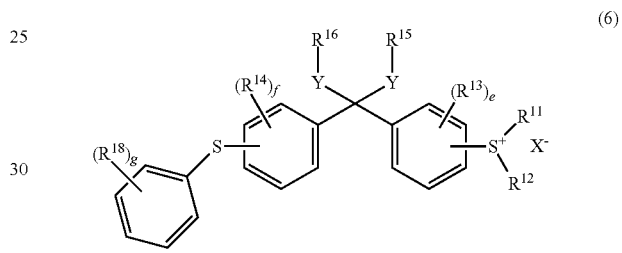

(6)

In the general formula (6), each of $R^{11}$ to $R^{16}$, $X^-$ and Y is independently selected from a same option as each of $R^{11}$ to $R^{16}$, $X^-$ and Y of the general formula (1).

$R^{18}$ is any one selected from the group consisting of an alkyl group, a hydroxy group, a mercapto group, an alkoxy group, an alkylcarbonyl group, an arylcarbonyl group, an alkoxycarbonyl group, an aryloxycarbonyl group, an arylsulfanylcarbonyl group, an arylsulfanyl group, an alkylsulfanyl group, an aryl group, a heteroaryl group, an aryloxy group, an alkylsulfinyl group, an arylsulfinyl group, an alkylsulfonyl group, an arylsulfonyl group, an arylsulfonyl group, a (meth)acryloyloxy group, a hydroxy(poly) alkyleneoxy group, an amino group, a cyano group, a nitro group and a halogen atom, wherein $R^{18}$ preferably has 1 to 12 carbon atoms when $R^{18}$ has a carbon atom, and these groups may have a substituent.

e is an integer of 0 to 4, f is an integer of 0 to 4, and g is an integer of 0 to 5.

$X^-$ is an anion. The anion is not particularly limited, and examples thereof include anions such as a sulfonate anion, a carboxylate anion, an imide anion, a methide anion, a carbanion, a borate anion, a halogen anion, a phosphate anion, an antimonate anion, an arsenate anion and the like.

More specifically, examples of the anion preferably include $ZA_a^-$, $(Rf)_b PF_{(6-b)}^-$, $R^{19}_c BA_{(4-c)}^-$, $R^{19}_c GaA_{(4-c)}^-$, $R^{20}SO_3^-$, $(R^{20}SO_2)_3C^-$ and $(R^{20}SO_2)_2N^-$. When the anion has two or more Rf, $R^{19}$ and $R^{20}$, each of the two of Rf, the two of $R^{19}$ and the two of $R^{20}$ may be bonded to each other to form a ring.

Z represents a phosphorus atom, a boron atom or an antimony atom. A represents a halogen atom, preferably a fluorine atom.

P represents a phosphorus atom, F represents a fluorine atom, B represents a boron atom, and Ga represents a gallium atom.

S represents a sulfur atom, O represents an oxygen atom, C represents a carbon atom, and N represents a nitrogen atom.

Rf is preferably an alkyl group in which 80 mol % or more of hydrogen atoms are substituted with a fluorine atom, and the alkyl group is preferably an alkyl group having 1 to 8 carbon atoms. Examples of an alkyl group to be Rf by fluorine substitution include: a linear alkyl group such as a methyl group, an ethyl group, a propyl group, a butyl group, a pentyl group, an octyl group and the like; a branched alkyl group such as an isopropyl group, an isobutyl group, a sec-butyl group, a tert-butyl group and the like; a cycloalkyl group such as a cyclopropyl group, a cyclobutyl group, a cyclopentyl group, a cyclohexyl group and the like; and the like. The proportion of hydrogen atoms of these alkyl groups substituted by the fluorine atom in Rf is preferably 80 mol % or more, more preferably 90 mol % or more, even more preferably 100%, based on a number of moles of hydrogen atoms that the original alkyl group has.

Particularly preferred examples of Rf include $CF_3^-$, $CF_3CF_2^-$, $(CF_3)_2CF^-$, $CF_3CF_2CF_2^-$, $CF_3CF_2CF_2CF_2^-$, $(CF_3)_2CFCF_2^-$, $CF_3CF_2(CF_3)CF^-$ and $(CF_3)_3C^-$. The b number of Rf are mutually independent, and therefore may be the same as or different from each other.

$R^{19}$ represents a phenyl group in which a part of hydrogen atoms is substituted with at least one halogen atom or an electron withdrawing group. Examples of the halogen atom include a fluorine atom, a chlorine atom, a bromine atom and the like. Examples of the electron withdrawing group include a trifluoromethyl group, a nitro group, a cyano group and the like. Among them, a phenyl group in which one hydrogen atom is substituted with a fluorine atom or a trifluoromethyl group is preferable. The c number of $R^{19}$ are mutually independent and may be the same as or different from each other.

$R^{20}$ represents an alkyl group having 1 to 20 carbon atoms and aryl group having 6 to 20 carbon atoms, the alkyl group and the aryl group in which a part or all of hydrogen atoms may be substituted with a fluorine atom. As for $R^{20}$, the alkyl group may be either linear, branched or cyclic, and the aryl group may be unsubstituted or may have a substituent.

a represents an integer of 4 to 6. b represents an integer of 1 to 5, preferably 2 to 4, and more preferably 2 or 3. c represents an integer of 1 to 4, and preferably 4.

Examples of the anion represented by $ZA_a^-$ include anions represented by $SbF_6^-$, $PF_6^-$, $BF_4^-$ and the like.

Examples of the anion represented by $(Rf)_6PF_{(6-b)}^-$ preferably include an anion represented by $(CF_3CF_2)_2PF_4^-$, $(CF_3CF_2)_3PF_3^-$, $((CF_3)_2CF)_2PF_4^-$, $((CF_3)_2CF)_3PF_3^-$, $(CF_3CF_2CF_2)_2PF4^-$, $(CF_3CF_2CF_2)_3PF_3^-$, $((CF_3)_2CFCF_2)_2PF_4^-$, $((CF_3)_2CFCF_2)_3PF_3^-$, $(CF_3CF_2CF_2CF_2)_2PF_4^-$, $(CF_3CF_2CF_2CF_2)_3PF_3^-$ and the like. Among them, anions represented by $(CF_3CF_2)_3PF_3^-$, $(CF_3CF_2CF_2)_3PF_3^-$, $((CF_3)_2CF)_3PF_3^-$, $((CF_3)_2CF)_2PF_4^-$, $((CF_3)_2CFCF_2)_3PF_3^-$ and $((CF_3)_2CFCF_2)_2PF_4^-$.

Examples of the anion represented by $R^{19}_cBA_{(4-c)}^-$ include $(C_6F_5)_4B^-$, $((CF_3)_2C_6H_3)_4B^{31}$, $(CF_3C_6H_4)_4B^-$, $(C_6F_5)_2BF_2^-$, $C_6F_5BF_3^-$, $(C_6H_3F_2)_4B^-$ and the like. Among them, anions represented by $(C_6F_5)_4B^-$ and $((CF_3)_2C_6H_3)_4B^-$ are preferable.

Examples of the anion represented by $R^{19}_cGaA_{(4-c)}^-$ include $(C_6F_5)_4Ga^-$, $((CF_3)_2C_6H_3)_4Ga^-$, $(CF_3C_6H_4)_4Ga^-$, $(C_6F_5)_2GaF_2^-$, $C_6F_5GaF_3^-$, $(C_6H_3F_2)_4Ga^-$ and the like. Among them, anions represented by $(C_6F_5)_4Ga^-$ and $((CF_3)_2C_6H_3)_4Ga^-$ are preferable.

Examples of the anion represented by $R^{20}SO_3^-$ include trifluoromethanesulfonate anion, pentafluoroethanesulfonate anion, heptafluoropropanesulfonate anion, nonafluorobutanesulfonate anion, pentafluorophenylsulfonate anion, p-toluenesulfonate anion, benzenesulfonate anion, camphorsulfonate anion, methanesulfonate anion, ethanesulfonate anion, propanesulfonate anion, butanesulfonate anion and the like. Among them, trifluoromethanesulfonate anion, nonafluorobutanesulfonate anion, methanesulfonate anion, butanesulfonate anion, benzenesulfonate anion and p-toluenesulfonate anion are preferable.

Examples of the anion represented by $(R^{20}SO_2)_3C^-$ include $(CF_3SO_2)_3C^-$, $(C_2F_5SO_2)_3C^-$, $(C_3F_7SO_2)_3C^-$, $(C_4F_9SO_2)_3C^-$ and the like.

Examples of the anion represented by $(R^{20}SO_2)_2N^-$ include $(CF_3SO_2)_2N^-$, $(C_2F_5SO_2)_2N^-$, $(C_3F_7SO_2)_2N^-$, $(C_4F_9SO_2)_2N^-$ and the like. A cyclic imide in which two moieties corresponding to $(R^{20}SO_2)$ are bonded to each other to form a ring structure may also be the anion represented by $(R^{20}SO_2)_2N^-$.

As a monovalent anion, in addition to the above anions, a perhalogenate ion ($ClO_4^-$, $BrO_4^-$ and the like), a halogenated sulfonate ion ($FSO_3^-$, $ClSO_3^-$ and the like), a sulfate ion ($CH_3SO_4^-$, $CF_3SO_4^-$, $HSO_4^-$ and the like), a carbonate ion ($HCO_3^-$, $CH_3CO_3^-$ and the like), an aluminate ion ($AlCl_4^-$, $AlF_4^-$ and the like), a hexafluorobismuthate ion ($BiF_6^-$), a carboxylate ion ($CH_3COO^-$, $CF_3COO^-$, $C_6H_5COO^-$, $CH_3C_6H_4COO^-$, $C_6F_5COO^{31}$, $CF_3C_6H_4COO^-$ and the like), an aryl borate ion ($B(C_6H_5)_4^-$, $CH_3CH_2CH_2CH_2B(C_6H_5)_3^-$ and the like), a thiocyanate ion ($SCN^-$), a nitrate ion ($NO_3^-$) and the like may be used.

These anions may have a substituent, and examples of the substituent include an alkyl group, a hydroxy group, a mercapto group, an alkoxy group, an alkylcarbonyl group, an arylcarbonyl group, an alkoxycarbonyl group, an aryloxycarbonyl group, an arylsulfanylcarbonyl group, an arylsulfanyl group, an alkylsulfanyl group, an aryl group, a heteroaryl group, an aryloxy group, an alkylsulfinyl group, an arylsulfinyl group, an alkylsulfonyl group, an arylsulfonyl group, a (meth)acryloyloxy group, a hydroxy(poly)alkyleneoxy group, an amino group, a cyano group, a nitro group, a halogen atom and the like.

Among these anions, a sulfonate anion and a carboxylate anion are preferable.

An onium salt according to an embodiment of the present invention, as an embodiment of the photoacid generator (A), may be an acid generator unit-containing resin in which an anion moiety is bonded to a part of a polymer. Examples of such an onium salt include a resin in which $X^-$ in the formulas (1), (2), (11) and (12) has a unit represented by a following general formula (5). The onium salt is preferably contained in the composition as a unit of the acid generator unit-containing resin, since LWR can be suppressed by suppressing diffusion of acid generated during exposure.

The unit represented by the general formula (5) may be contained in the resin (B), or may be contained in a resin different from the resin (B).

[Chem. 17]

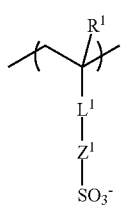

(5)

Each of $R^1$ and $L^1$ is independently selected from a same option as each of $R^1$ and $L^1$ in the formula (1).

$Z^1$ is any one selected from the group consisting of: a linear or branched alkyl group having 1 to 12 carbon atoms; a linear or branched alkenyl group having 1 to 12 carbon atoms; and an aryl group having 6 to 14 carbon atoms.

A part or all of hydrogen atoms of the alkyl group, the alkenyl group and the aryl group in $Z^1$ may be substituted with a fluorine atom. At least one methylene group in these groups may be substituted with a divalent hetero atom-containing group.

Examples of the anion moiety represented by the formula (5) are described below. However, the present invention is not limited thereto.

[Chem. 18]

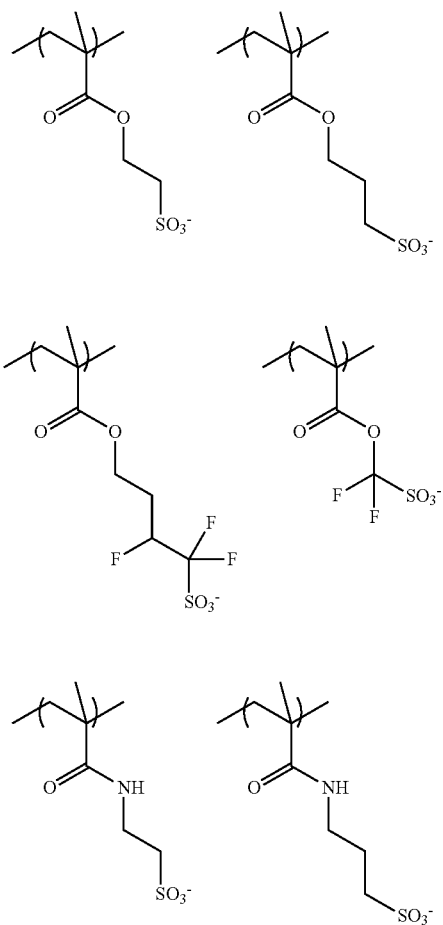

[Chem. 19]

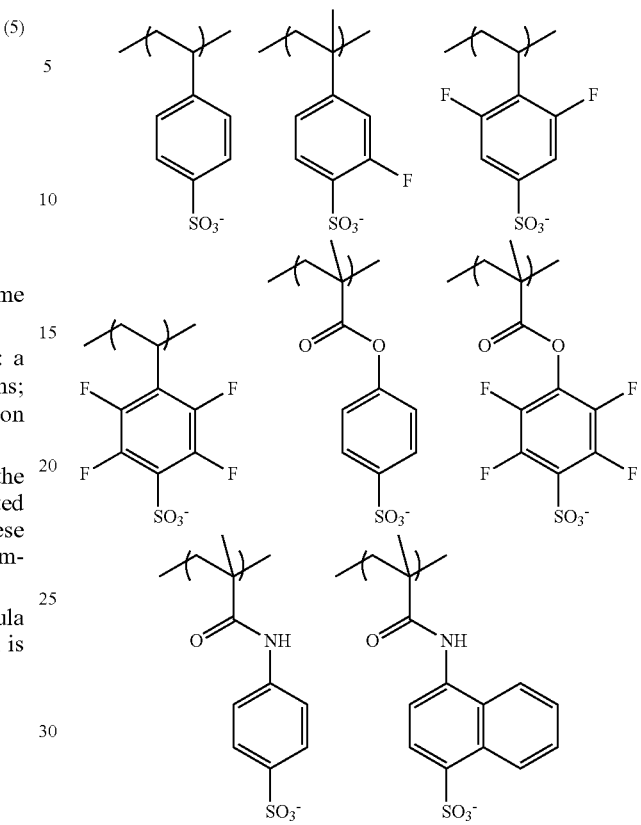

The onium salt according to some embodiments of the present invention has a molar absorption coefficient at 365 nm of preferably less than $1.0 \times 10^5$ cm$^2$/mol, and more preferably less than $1.0 \times 10^4$ cm$^2$/mol.

The ketone derivative converted from the acetal or the thioacetal of the onium salt by deprotection according to some embodiments of the present invention has a molar absorption coefficient at 365 nm of preferably $1.0 \times 10^5$ cm$^2$/mol or more, and more preferably $1.0 \times 10^6$ cm$^2$/mol or more.

The molar absorption coefficient at 365 nm of the ketone derivative is preferably 5 times or more, more preferably 10 times or more, and even more preferably 20 times or more than the molar absorption coefficient of the onium salt according to some embodiments of the present invention.

In order to obtain the above characteristics, the onium salt may be oniumu salts represented by the formula (1), (2), (11) or (12).

<2> Method for synthesizing the onium salt Among the onium salt according to an embodiment of the present invention, a method for synthesizing the sulfonium salt and the iodonium salt will be described. However the present invention is not limited thereto.

When the sulfonio group moiety of a desired sulfonium salt has an alkyl group, for example, the following method can be used. First, an alkylsulfanyl group-containing bromobenzene, h=1 in the following formula, and an aryl group may have $R^{13}$ group; and a benzoyl chloride which may have an $R^{14}$ group, i=1 in the following formula; are reacted with a Grignard reagent to obtain an alkylsulfanylbenzophenone derivative. Here, $R^{14}$ may be a fluoro group to obtain an alkylsulfanylbenzophenone derivative having any substituent by an aromatic nucleophilic substitution reaction. Subsequently, an alkylating agent ($R^{12}{}_2SO_4$) such as dimethylsulfuric acid or the like is added to obtain a sulfonium salt, and then salt exchange is carried out using a salt having a corresponding anion to obtain a dialkyl-arylsulfonium salt. Thereafter, the desired sulfonium salt is obtained by acetalizing the carbonyl group using an acid catalyst and an alcohol ($R^{15}OH$).

[Chem. 20]

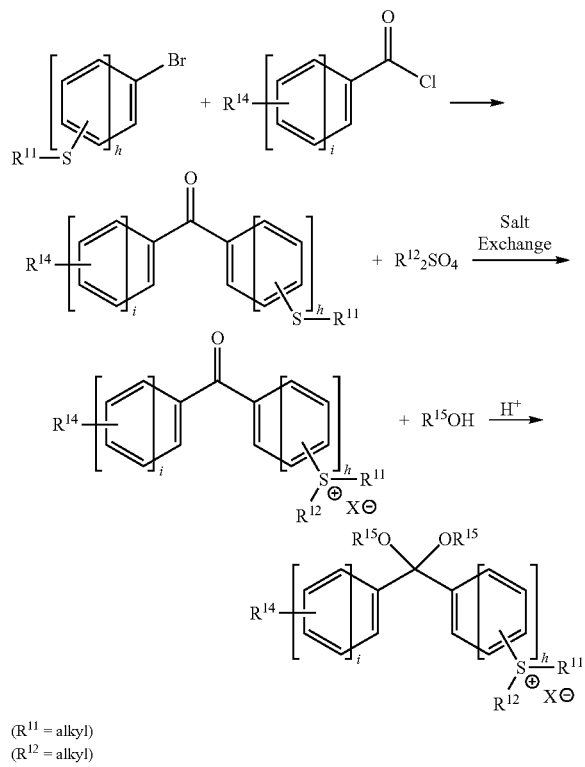

($R^{11}$ = alkyl)
($R^{12}$ = alkyl)

When the sulfonio group moiety of the desired sulfonium salt has an aryl group, for example, the following method can be used. First, a benzene which may have an $R^{14}$ group, i=1 in the following formula; and a bromobenzoyl chloride, h=1 in the following formula, and an aryl group may have $R^{13}$ group; are reacted by Friedel-Crafts reaction with a Lewis acid to obtain a bromobenzophenone derivative. Subsequently, the carbonyl group is acetalized with an acid catalyst and an alcohol ($R^{15}OH$). Then, the acetal and a sulfoxide compound having $R^{11}$ group and $R^{12}$ group are reacted with a Grignard reagent to obtain a sulfonium salt, and thereafter, salt exchange is carried out using a salt having a corresponding anion to obtain the desired sulfonium salt.

[Chem. 21]

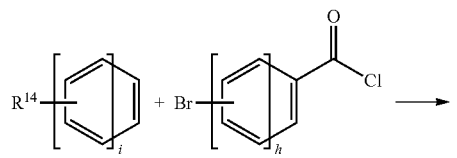

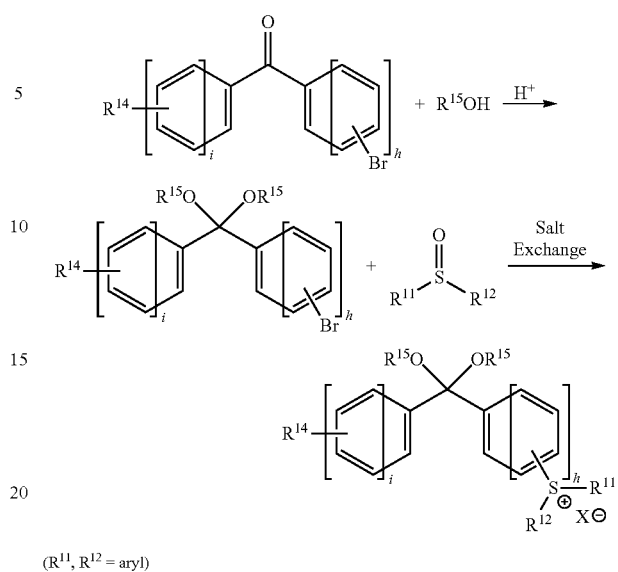

($R^{11}$, $R^{12}$ = aryl)

In the case of the iodonium salt, for example, the following method can be used. First, a benzene which may have an $R^{14}$ group, m=1 in the following formula; and a bromobenzoyl chloride, n=1 in the following formula, and an aryl group may have $R^{13}$ group; are reacted by Friedel-Crafts reaction with a Lewis acid to obtain an iodobenzophenone derivative. Subsequently, the iodobenzophenone derivative is reacted with an oxidizing agent such as metachloroperbenzoic acid (mCPBA) and the like in the presence of an acid such as trifluoromethanesulfonic acid and the like, and then reacted with an aromatic compound $R^{17}$ to obtain an iodonium salt. Thereafter, the desired iodonium salt is obtained by acetalizing the carbonyl group using an acid catalyst and an alcohol ($R^{15}OH$) and, if necessary, salt exchange is carried out using a salt having a corresponding anion.

[Chem. 22]

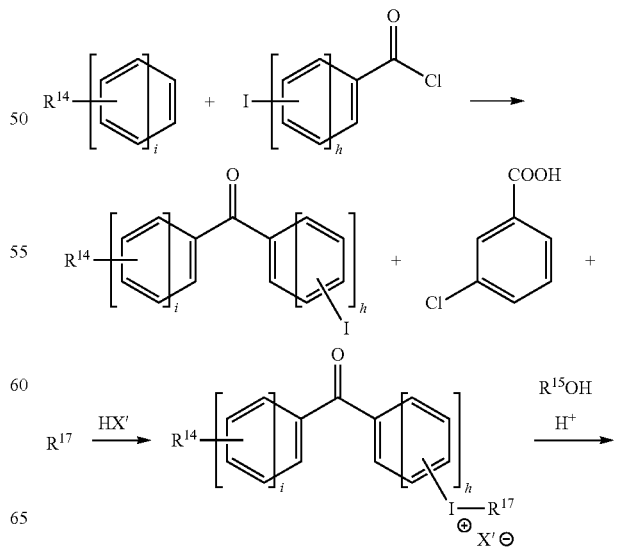

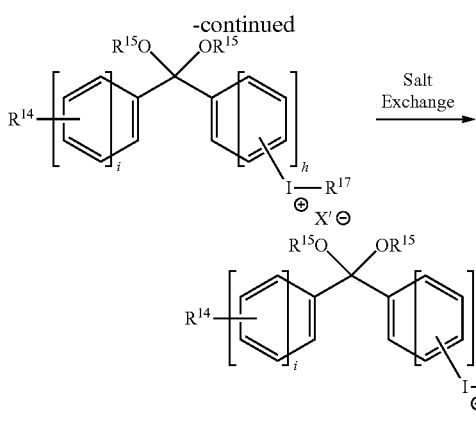

When the anion moiety of the onium salt is a polymer component bonded to a part of the polymer, for example, the following synthesis method can be used. First, salt exchange is carried out using a commercially available or, as required, synthesized sulfonate having polymerizable functional group and the sulfonium salt or iodonium salt to obtain an onium salt (polymerizable onium salt) having the polymerizable functional group in an anion moiety. Subsequently, by copolymerizing the obtained polymerizable onium salt with an acid dissociable compound or the like using a radical initiator, the desired polymer component can be obtained.

[Chem. 23]

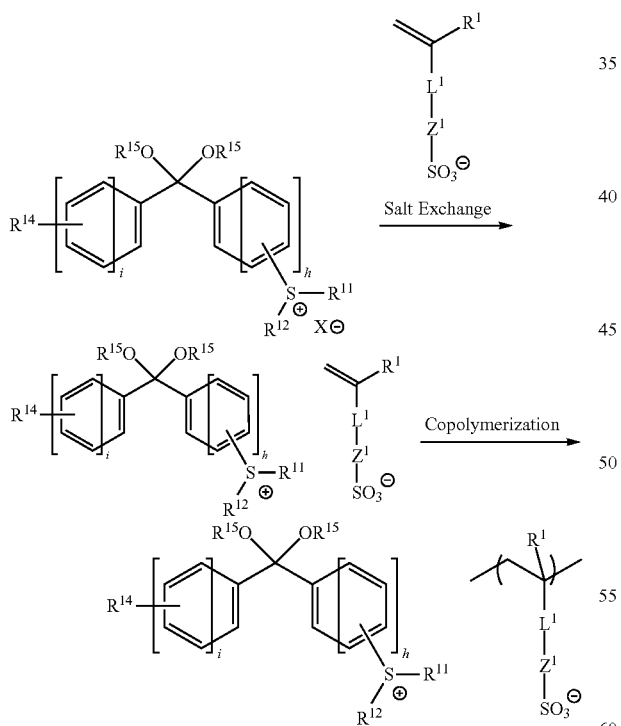

When the desired onium salt forms a cyclic structure through $L^3$, for example, the following synthesis method can be used. First, some of cyclic ketone derivatives (a) forming a cyclic structure through $L^3$ are commercially available, and others can be synthesized as required. The cyclic ketone derivative and a sulfoxide compound having $R^{11}$ group and $R^{12}$ group are reacted with a strong acid such as methanesulfonic acid or the like and a dehydrating agent to obtain a sulfonium salt, in the following formula, the sulfonium group is bonded to an aryl group substituted with $R^{13}$, but may be bonded to the aryl group substituted with $R^{14}$. Subsequently, the desired sulfonium salt can be obtained by acetalizing the carbonyl group using an acid catalyst and an alcohol ($R^{15}OH$).

[Chem. 24]

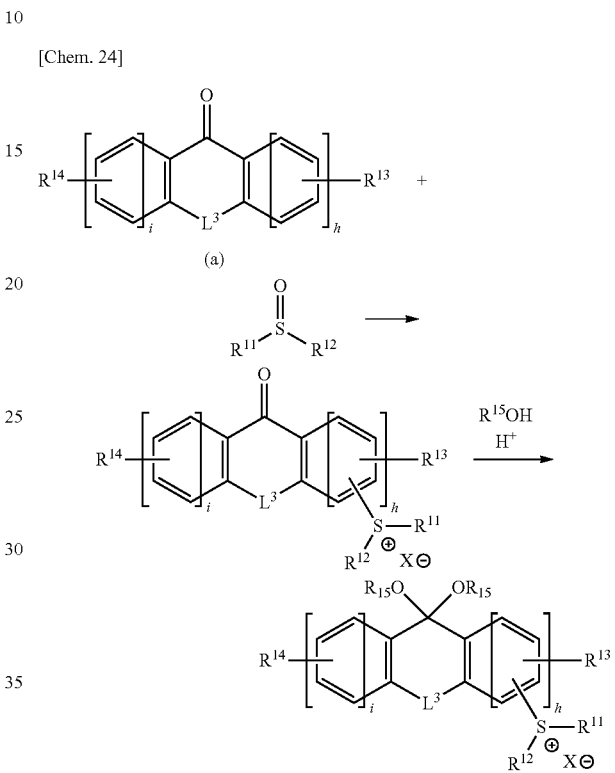

When the desired onium salt has $L^4$ or $L^5$ having an alkenylene group, for example, the following synthesis method can be used. An acetyl compound (b) having an $R^{13}$ group or $R^{14}$ group and an aldehyde compound (c) are reacted by an aldol reaction using sodium hydroxide to obtain an unsaturated ketone compound (d). Subsequently, the unsaturated ketone compound and a sulfoxide compound having $R^{11}$ group and $R^{12}$ group are reacted with a strong acid such as methanesulfonic acid or the like and a dehydrating agent to obtain a sulfonium salt, in the following formula, the sulfonium group is bonded to an aryl group substituted with $R^{13}$, but may be bonded to the aryl group substituted with $R^{14}$. Thereafter, the desired sulfonium salt can be obtained by acetalizing the carbonyl group using an acid catalyst and an alcohol ($R^{15}OH$).

[Chem. 25]

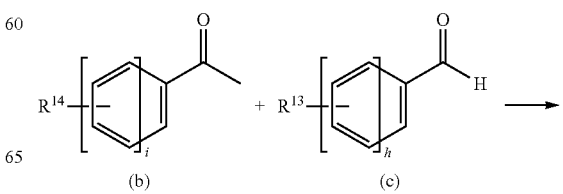

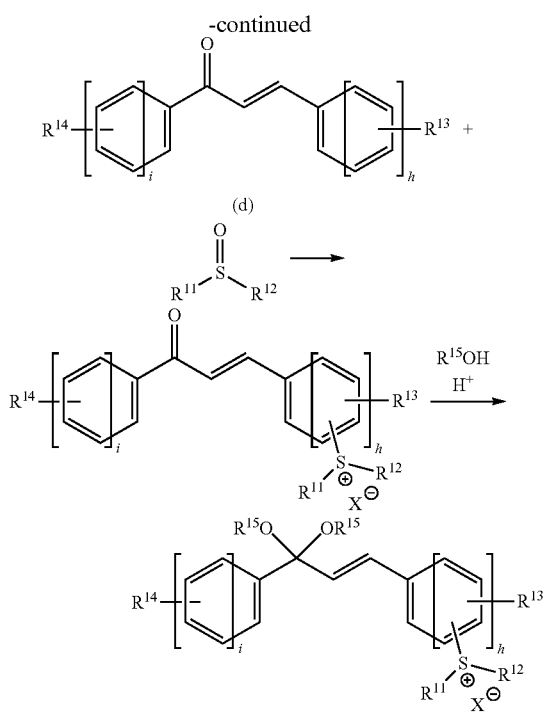

<3> Composition

An embodiment of the present invention relates to a composition containing the photoacid generator (A) and an acid reactive compound. Preferably, the composition further contains an acid-diffusion controller.

(Photoacid Generator)

A content of the photoacid generator in the composition according to an embodiment of the present invention is, with respect to 100 parts by mass of the resist composition component excluding the photoacid generator, preferably 0.1 to 50 parts by mass, more preferably 1 to 30 parts by mass, and even more preferably 3 to 15 parts by mass.

In calculating the content of the photoacid generator, an organic solvent is not included in 100 parts by mass of the resist composition component.

When the photoacid generator is contained in a resin as one unit, that is, when the photoacid generator is a polymer component, the content is based on a mass excluding the polymer main chain. In addition, when the photoacid generator is a polymer component and is contained, as a unit of the same polymer, together with at least one unit selected from the group consisting of: a unit represented by following general formulas (4a) to (4b), hereinafter also referred to as "unit C"; and a unit represented by general formulas (3a) to (3d), hereinafter also referred to as "unit B", the unit acting as the photoacid generator, hereinafter also referred to as "unit A", is preferably from 0.1 to 40 mol %, more preferably from 1 to 30 mol %, and even more preferably 3 to 20 mol % in all polymer units.

The photoacid generator may be used solely or in combination of two or more, and may be used in combination with other photoacid generators, regardless of the polymer component and the low molecular weight component.

Examples of photoacid generators other than the photoacid generator containing the onium salt include general-purpose ionic photoacid generators and nonionic photoacid generators. Examples of the ionic photoacid generators include onium salt compounds such as iodonium salts, sulfonium salts and the like other than those described above. Examples of the nonionic photoacid generator include N-sulfonyloxyimide compounds, oxime sulfonate compounds, organic halogen compounds, sulfonyldiazomethane compounds and the like.

When the composition contains the photoacid generator other than the photoacid generator containing the onium salt, the content is preferably 0.1 to 50 parts by mass with respect to 100 parts by mass of the resist composition component excluding the total photoacid generator.

(Acid Reactive Compound)

The acid reactive compound is preferably at least one selected from the group consisting of: a compound having a protecting group to be deprotected by an acid; a compound having a polymerizable group to be polymerized by an acid; and a crosslinking agent exerting a crosslinking action by an acid.

The compound having a protecting group to be deprotected by an acid is a compound whose solubility in a developing solution changes by forming a polar group due to deprotection of the protecting group by an acid. For example, in the case of water-based development using an alkaline developing solution or the like, the compound is insoluble in an alkaline developing solution, and by deprotection of the protecting group of the compound in the exposed portion by an acid generated from the photoacid generator with exposure, the compound becomes soluble in the alkaline developing solution.

According to an embodiment of the present invention, the acid reactive compound is particularly preferably a resin (B) whose solubility in a developing solution changes by an acid.

(Resin (B))

The resin (B) has at least one of the units B represented by the formulas (3a) to (3d) having a protective group to be deprotected by an acid.

The unit B has the protecting group to be deprotected by an acid, is a unit contained in the resin (B), and is a unit in which the protecting group is deprotected to generate a polar group and the solubility in the developing solution changes. For example, in the case of water-based development using an alkaline developing solution or the like, the compound is insoluble in an alkaline developing solution, and by deprotection of the protecting group of the unit B in an exposed portion by an acid generated from the photoacid generator with exposure, the compound becomes soluble in the alkaline developing solution.

In the present invention, it is not limited to the alkaline developing solution, and it may be an aqueous neutral developing solution or an organic solvent developing solution. Therefore, when the organic solvent developing solution is used, the compound having a protecting group to be deprotected by an acid is a compound whose solubility in the organic solvent developing solution becomes lower due to generating a polar group by deprotecting the protecting group of the compound in an exposed portion by the acid generated from the photoacid generator with exposure.

Examples of the polar group include a hydroxy group, a carboxy group, an amino group, a sulfo group and the like. Among them, a polar group having —OH in the structure is preferable, and the hydroxy group or the carboxy group is preferable.

Specific examples of the protecting group to be deprotected by an acid include: a group forming a tertiary alkyl ester group with a carboxy group; an alkoxyacetal group; a tetrahydropyranyl group; a siloxy group; a benzyloxy group; and the like. As a compound having the protecting group, a compound having a styrene skeleton, a methacrylate or acrylate skeleton to which these protecting groups are bonded is preferably used.

The resin (B) may be a low molecular weight compound having a protecting group, instead of a polymer component having a unit B having a protecting group to be deprotected by an acid.

The low molecular weight compound having a protective group has at least one of the units represented by the formulas (3a) to (3d), as the above resin (B).

In the formulas (3a) to (3d), $R^1$ is any one selected from the group consisting of a hydrogen atom, an alkyl group and a halogenated alkyl group.

Examples of the alkyl group include a methyl group, an ethyl group, an n-propyl group, an n-butyl group, an isopropyl group, a t-butyl group, a cyclopropyl group, a cyclobutyl group, a cyclopentyl group and a cyclohexyl group, and a part of hydrogen atoms in these groups may be substituted with a halogen atom. Among them, $R^1$ is preferably the hydrogen atom, the methyl group or a trifluoromethyl group.

In the general formulas (3a) to (3d), a moiety represented by a following formula (a-1) or (a-2) is the protecting group to be deprotected by an acid, hereinafter also referred to as "acid labile group", and the solubility in the developing solution changes due to generating a carboxylic acid or phenolic hydroxyl group by decomposition by an acid.

A broken line in the following formulas (a-1) and (a-2) represents a bonding site with $L^1$ or an oxygen atom in the formulas (3a) to (3d). $R^2$ to $R^7$ in the following formulas (a-1) and (a-2) are preferably selected from a same option as $R^2$ to $R^7$ in the general formulas (3a) to (3d).

[Chem. 26]

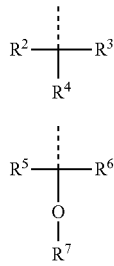

(a-1)

(a-2)

In the formula (a-1), each of $R^2$ and $R^3$ is independently a linear, branched or cyclic alkyl group. Examples of such alkyl group include a methyl group, an ethyl group, an n-propyl group, an n-butyl group, an isopropyl group, a t-butyl group, a cyclopropyl group, a cyclobutyl group, a cyclopentyl group, a cyclohexyl group, an adamantan-1-yl group, an adamantan-2-yl group, a norbornan-1-yl group, a norbornan-2-yl group and the like.

$R^4$ is a linear, branched or cyclic alkyl group which may have a substituent, the alkyl group is selected from a same option as $R^2$, and a part of hydrogen atoms in these groups may be substituted with a hydroxyl group, an alkoxy group, an oxo group, an amino group, an alkylamino group and the like. $R^5$, $R^6$ and $R^7$ may be bonded each other directly with a single bond or through a methylene group to form a ring structure.

In the formula (a-2), each of $R^5$ and $R^6$ is independently a hydrogen atom, and a linear or cyclic alkyl group, and the alkyl group is selected from a same option as each of the alkyl group of $R^2$.

$R^7$ is a linear, branched or cyclic alkyl group which may have a substituent, the alkyl group is selected from a same option as each of the alkyl group of $R^2$, and a part of hydrogen atoms in these groups may be substituted with a hydroxyl group, an alkoxy group, an oxo group, an amino group, an alkylamino group and the like. $R^5$, $R^6$ and $R^7$ may be bonded each other directly with a single bond or through a methylene group to form a ring structure.

Specific examples of the formulas (a-1) and (a-2) include the following structures. However, the present invention is not limited thereto.

[Chem. 27]

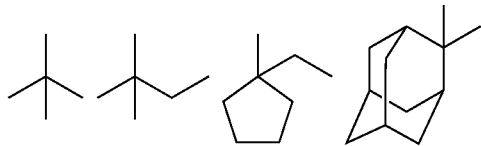

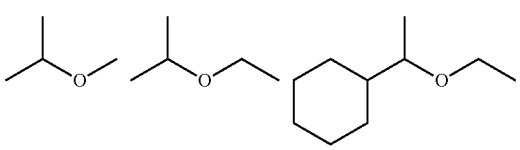

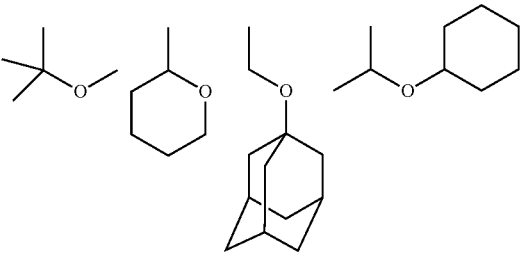

$R^8$ in the general formulas (3c) to (3d) is any one selected from the group consisting of an alkyl group, a hydroxy group, an alkoxy group, an alkylcarbonyl group, an alkylsulfanyl group, an alkylsulfinyl group, an alkylsulfonyl group, an amino group, a cyano group, a nitro group and a halogen atom. These are selected from a same option as $R^{13}$.

$L^1$ in the general formulas (3a) to (3d) is any one selected from the group consisting of: a direct bond, a carbonyloxy group; a carbonylamino group; a linear, branched or cyclic alkylenecarbonyloxy group which may have a substituent; and a linear, branched or cyclic alkylenecarbonylamino group which may have a substituent, and the carbonyloxy group or the carbonylamino group is bonded to the acid labile group.

In the general formulas (3a) to (3d), l is an integer of 1 to 2; m is an integer of 0 to 4 when l is 1, and an integer of 0 to 6 when l is 2; n is an integer of 1 to 5 when l is 1, and an integer of 1 to 7 when l is 2; and m+n is 1 to 5 when l is 1, and 1 to 7 when l is 2.

Specific examples of the unit B represented by the general formulas (3a) to (3d) include the followings. However, the present invention is not limited thereto.

[Chem. 28]

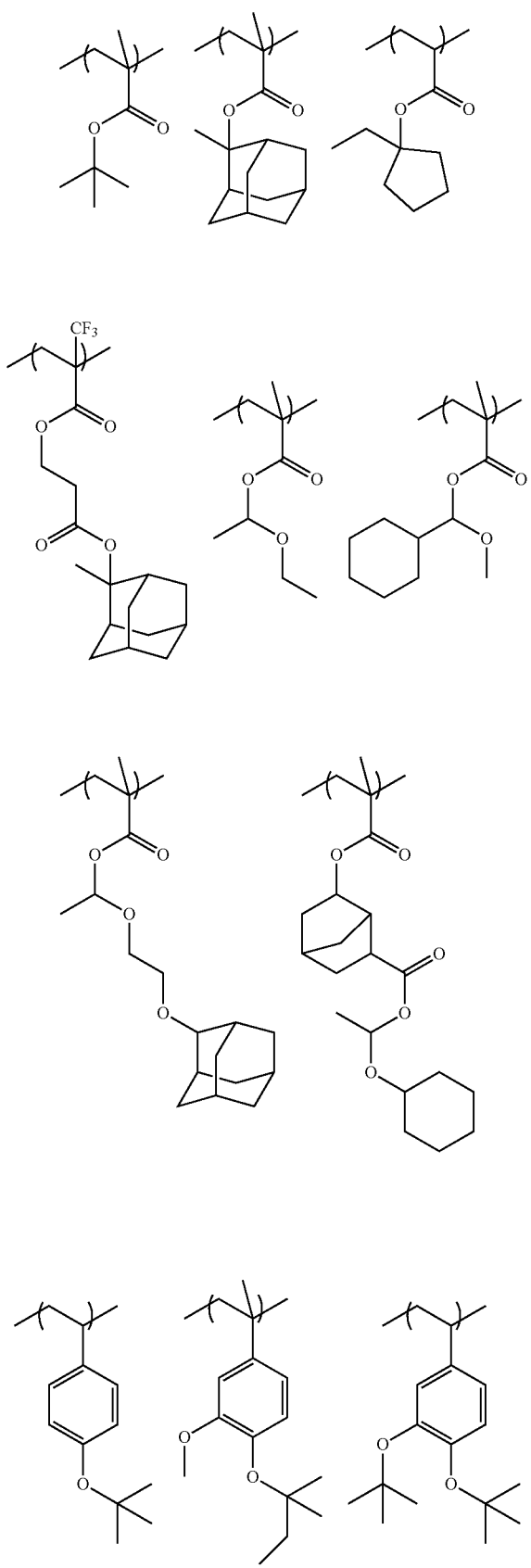
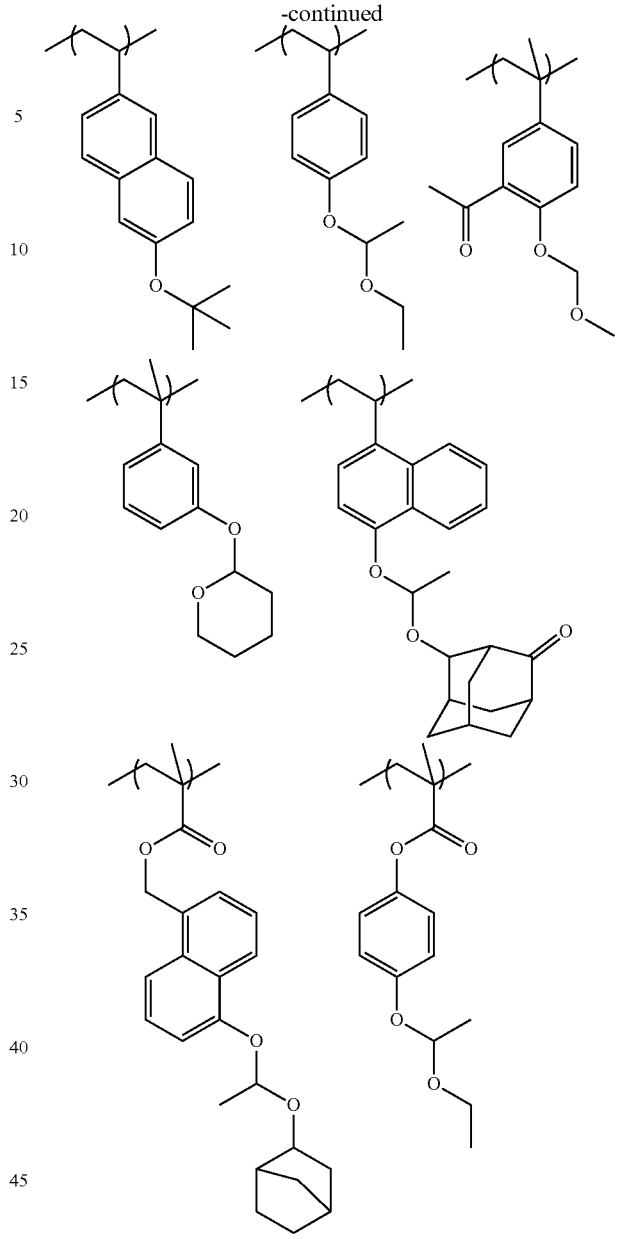

Instead of or in addition to the resin (B), the compound having a polymerizable group to be polymerized by an acid and/or the crosslinking agent exerting a crosslinking action by an acid may be contained in the composition. The compound having a polymerizable group to be polymerized by an acid is a compound whose solubility in a developing solution changes by polymerizing by an acid. For example, in the case of water-based development, a compound soluble in an aqueous developing solution is affected and the solubility of the compound in the aqueous developing solution decreases after polymerization. Specific examples thereof include compounds having an epoxy group, a vinyloxy group, an oxetanyl group and the like.

The compound having a polymerizable group to be polymerized by an acid may be a polymerizable low molecular compound or a polymer component having a unit having a polymerizable group. The crosslinking agent exerting a crosslinking action by an acid is a crosslinking agent whose solubility in the developing solution changes by crosslinking by an acid. For example, in the case of water-based development, a compound soluble in the aqueous developing solution is affected and the solubility of the compound in the aqueous developing solution decreases after polymerization or crosslinking. Specific examples thereof include crosslinking agents having a crosslinkable group such as an epoxy group, a vinyloxy group, a 1-alkoxyamino group, an oxetanyl group and the like. When the compound is a crosslinking agent having a crosslinking action, as a compound to be crosslinked with, that is, a compound which reacts with a crosslinking agent and changes solubility in the developing solution, a compound having a phenolic hydroxyl group and the like may be used.

The compound exerting a crosslinking action by an acid may be a crosslinkable low molecular weight compound or a polymer component having a unit having a crosslinkable group.

The resin (B) may contain, in addition to at least one of the units B represented by the formulas (3a) to (3d), other units normally used in the resist composition in the polymer component. Examples of other units include: a unit having at least one skeleton selected from the group consisting of a lactone skeleton, a sultone skeleton, a sulfolane skeleton, a lactam skeleton and the like; a unit having at least one structure selected from the group consisting of an ether structure, an ester structure, an acetal structure, a structure having a hydroxy group and the like; a unit containing a hydroxyaryl group; and the like. Further, the resin (B) may contain the unit A.

The resin (B) may be contained in the composition as a homopolymer containing the unit B or as a copolymer containing the unit B, the unit A and at least one unit C selected from the group consisting of units represented by general formulas (4a) to (4b). When the resin (B) is the copolymer, a content of the unit B in the resin (B) is preferably 3 to 50 mol %, more preferably from 5 to 35 mol %, and even more preferably from 7 to 30 mol %.

(Resin (C))

In an embodiment of the present invention, it is preferably that the composition contains a resin (C) having one or more units C represented by the following formulas (4a) to (4b), or the resin (B) further contains the unit C.

[Chem. 29]

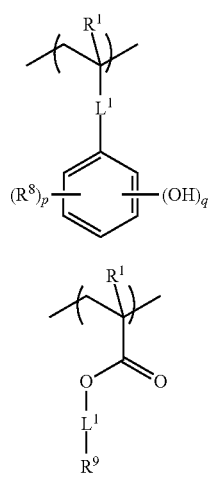

(4a)

(4b)

In the general formulas (4a) and (4b), each of $R^1$, $R^8$ and $L^1$ is independently selected from a same option as each of $R^1$, $R^8$ and $L^1$ of the formulas (3a) to (3d).

$R^9$ is a cyclic group having at least one selected from the group consisting of —C(O)—O—, —SO$_2$— and —O—SO$_2$—.

p is an integer of 0 to 4, and q is an integer of 1 to 5.

Examples of the cyclic group include groups having a lactone skeleton, a sultone skeleton, a sulfolane skeleton or the like.

The unit C represented by the formulas (4a) to (4b) may be contained in the copolymer containing at least one of the unit A and/or the formulas (3a) to (3d) as the unit B, or may be contained as a unit of other polymers.

A unit represented by the formula (4a) is a hydroxyaryl group-containing unit, hereinafter also referred to as "unit C1", and a unit represented by the formula (4b) is a unit having a lactone skeleton, a sultone skeleton or a sulfolane skeleton, hereinafter also referred to as "unit C2".

A polymer having the hydroxyaryl group-containing unit C1 is preferably used since it can be a hydrogen source in decomposition of the photoacid generator, the acid generation efficiency can be improved, and high sensitivity can be obtained. Since the polymer having the hydroxyaryl group-containing unit C1 has a low ionization potential, when an electron beam or extreme ultraviolet (EUV) is used for a first active energy ray described later, a secondary electron is easily generated, so that the acid generation efficiency can be improved and high sensitivity can be obtained.

Examples of the hydroxyaryl group-containing unit C1 include the followings. However, the present invention is not limited thereto.

[Chem. 30]

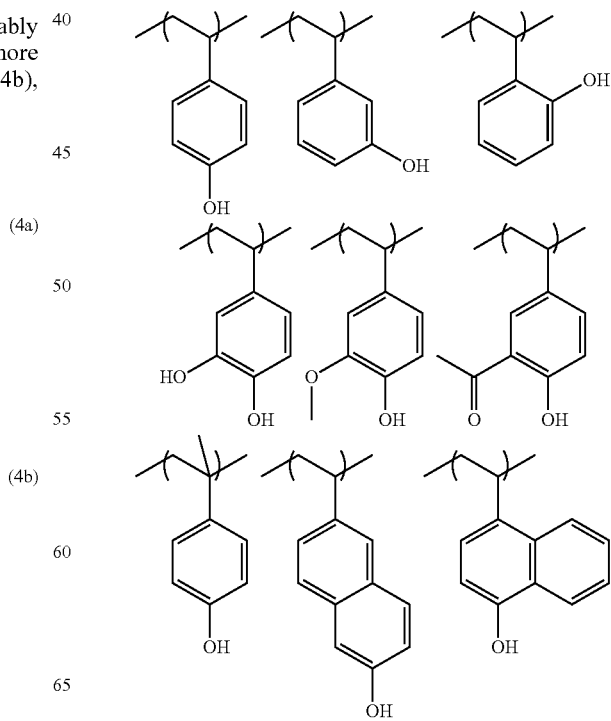

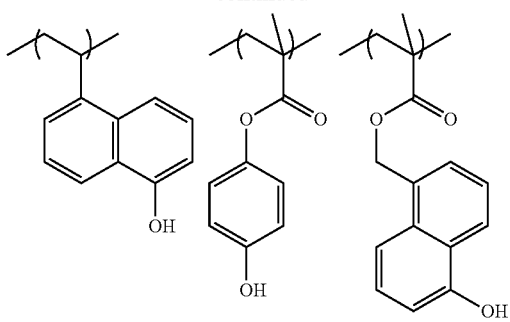

When the hydroxyaryl group-containing unit C1 is included as a unit of the same polymer together with at least one selected from the group consisting of the unit A and the unit B, a content of the hydroxyaryl group-containing unit C1 in all polymer units is, for a positive resist composition of the water-based development, preferably 3 to 90 mol %, more preferably 5 to 80 mol %, and even more preferably 7 to 70 mol %. For a negative resist composition of the water-based development, the content is preferably 60 to 99 mol %, more preferably 70 to 98 mol %, and even more preferably 75 to 98 mol %.

Examples of the unit C2 having a lactone skeleton, a sultone skeleton or a sulfolane skeleton include the followings. However, the present invention is not limited thereto.

[Chem. 31]

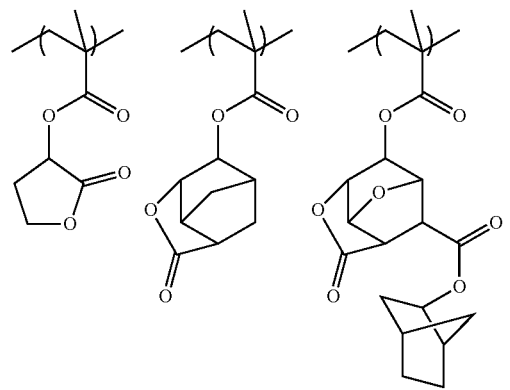

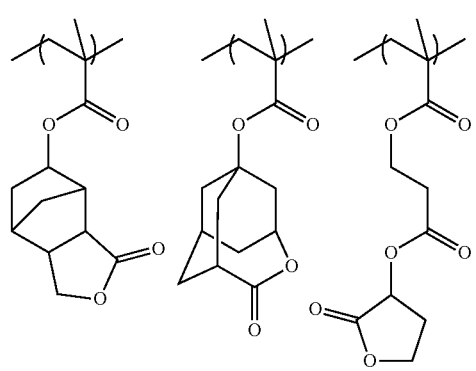

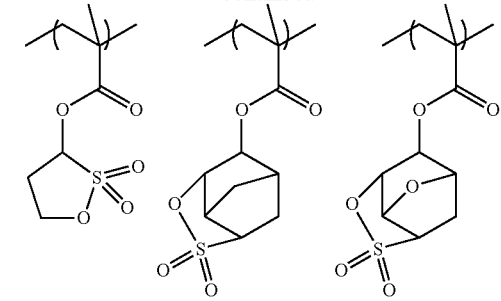

When a sultone skeleton-containing unit or a sulfolane skeleton-containing unit is used as the unit C2, an acid is generated by ionization by irradiation with the electron beam or the extreme ultraviolet (EUV) as the first active energy ray to contribute to the deprotection reaction of the acetal of the onium salt in some embodiments of the present invention, and more ketone derivatives having absorption for the second active energy ray can be produced. It also contributes to a polarity conversion by a reaction with the resin (B) containing the unit B, so that the solubility of the resin in the developing solution further changes. That is, high sensitivity can be obtained.

When, the lactone skeleton-containing unit, the sultone skeleton-containing unit, or the sulfolane skeleton-containing unit is contained as the unit C2 in the same polymer together with at least one selected from the group consisting of the unit A and the unit B, the content of the unit C2 in all polymer units is preferably 3 to 70 mol %, more preferably 5 to 50 mol %, and even more preferably 7 to 40 mol %.

In the composition according to an embodiment of the present invention, in addition to the unit A, the unit B and the unit C, another compound may be contained in the resin (B) and/or the resin (C) as a unit of the same polymer. The other compound are not particularly limited as long as it is a compound generally used as a resin composition such as ArF lithography, KrF lithography, electron beam lithography, EUV lithography or the like.

(Low Molecular Weight Compound Containing Sulfone or Sulfonate Ester, or Polymer)

The composition according to an embodiment of the present invention may contain a low molecular weight compound containing a sulfone or a sulfonate ester, or a polymer.

The sulfone or the sulfonate ester is not particularly limited but is preferably one having a linear, branched or cyclic alkyl, or an aryl group. More preferably, a part or all of hydrogen atoms of the alkyl group or the aryl group are substituted with a fluorine atom. Since the compound is contained, the acid is generated by ionization by irradiation with the electron beam or the extreme ultraviolet, so that the sensitivity of the resist can be enhanced.

A content of the compound containing the sulfone or the sulfonate ester is preferably 0.1 to 50 parts by mass with respect to 100 parts by mass of the resist composition component excluding the total amount of the photoacid generator.

Specific examples of the compound containing the sulfone or the sulfonate ester include dimethylsulfone, isopropylmethylsulfone, methylphenylsulfone, diphenylsulfone, phenyltrifluoromethylsulfone, bis(4-fluorophenyl)sulfone, bis(phenylsulfonyl)methane, methyl methanesulfonate, isopropyl methanesulfonate, ethyl trifluoromethanesulfonate, methyl benzenesulfonate, 1,3-propane sultone, 1-propene 1,3-sultone, 1,4-butane sultone, 1,2-bis(tosyloxy)ethane, 1,8-naphthosultone and the like. Each of them may be used solely or in combination of two or more.

(Fluorine-Containing Water Repellent Polymer)

The composition according to an embodiment of the present invention may contain a fluorine-containing water repellent polymer.

The fluorine-containing water repellent polymer is not particularly limited, but one usually used in an immersion exposure process, and a proportion of the fluorine atom content is preferably larger than that of the above polymer. In the case of forming a resist film using a composition containing the fluorine-containing water repellent polymer, the fluorine-containing water repellent polymer is localized to the surface of the resist film due to the water repellency of the fluorine-containing water repellent polymer.

As the fluorine proportion of the fluorine-containing water repellent polymer, hydrogen atoms in a hydrocarbon group in the fluorine-containing water repellent polymer are fluorinated preferably 25% or more, and more preferably 50% or more.

A content of the fluorine-containing water repellent polymer in the composition is, with respect to 100 parts by mass of the polymer according to an embodiment of the present invention, not the fluorine-containing water repellent polymer, preferably 0.5 to 10 parts by mass from a viewpoint of improving the hydrophobicity of the resist film. The fluorine-containing water repellent polymer may be used solely or in combination of two or more.

(Photosensitizer and its Precursor)

The composition according to an embodiment of the present invention may contain a photosensitizer and its precursor. Hereinafter, the photosensitizer and its precursor are referred to as "sensitizer compound" collectively.

The sensitizer compound is not particularly limited as long as it does not reduce the effect of the onium salt according to some embodiments of the present invention, and examples of the sensitizer compound include a thioxanthone derivative and an acetalized compound thereof, a benzophenone derivative and an acetalized compound thereof, a naphthalene derivative, an anthracene derivative, an alkyl alcohol, an aryl alcohols and the like.

In addition, as the sensitizer compound, for example, a photosensitizer precursor represented by the following general formula (7) may be contained. By containing the photosensitizer precursor, a photosensitizer is generated from the photosensitizer precursor by irradiation with the first active energy ray, and then irradiated with the second active energy, so that it is possible to utilize the sensitization reaction occurring between the photosensitizer and the onium salt according to some embodiments of the present invention, and possible to enhance the sensitivity of the resist.

[Chem. 32]

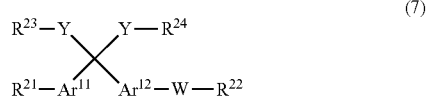

(7)

In the formula (7), each of $Ar^{11}$ and $Ar^{12}$ is independently a phenylene group which may have a substituent; $R^{21}$ is any one selected from the group consisting of an alkylsulfanyl group, an arylsulfanyl group and an alkylsulfanylphenyl group which may have a substituent; W is any one selected from the group consisting of a sulfur atom, an oxygen atom and a direct bond; $R^{22}$ is an alkyl group or an aryl group which may have a substituent; each of Y is independently an oxygen atom or a sulfur atom; each of $R^{23}$ and $R^{24}$ is any one independently selected from the group consisting of a linear, branched or cyclic alkyl group, alkenyl group, alkynyl group and aralkyl group which may have a substituent; and $R^{23}$ and $R^{24}$ may be bonded each other to form a ring structure with two of Y in the formula.

Each of $Ar^{11}$ and $Ar^{12}$ in the above formula (7) is a phenylene group, and may have a substituent other than $R^{21}$ or -W-$R^{22}$, hereinafter, substituents of $Ar^{11}$ and $Ar^{12}$ are referred to as "fourth substituent". Note that $Ar^{11}$ and $Ar^{12}$ are preferably not bonded indirectly to form a ring from a viewpoint of synthesis.

An example of the fourth substituent is an electron donating group. Specific examples of the electron-donating group include an alkyl group, an alkenyl group, an alkoxy group, an alkoxyphenyl group, an alkylsulfanyl group, an arylsulfanyl group, an alkylsulfanylphenyl group and the like. Another example of the fourth substituent is a long-chain alkoxy group having a polyethylene glycol chain ($-(CO_2H_4)_n^-$). When the fourth substituent is bonded to the para position of $Ar^{11}$ or $Ar^{12}$, $Ar^{11}$ or $Ar^{12}$ may have an OH group as the fourth substituent.

In the present invention, a substitution position such as "para position" of $Ar^{11}$ or $Ar^{12}$ indicates a position with respect to a group to which a quaternary carbon bonded to two of Y, $Ar^{11}$ and $Ar^{12}$ in the formula (7) is bonded. The substitution position such as "para position" is the position with respect to the group to which the quaternary carbon is bonded, not only according to the fourth substituent but also another group.

The alkyl group and alkenyl group as the fourth substituent are selected from a same option as the alkyl group and alkenyl group of $R^{11}$ in the formula (1). The alkoxy group as the fourth substituent is selected from a same option as the alkoxy group (—OR) in the first substituent.

Examples of the alkylsulfanyl group, arylsulfanyl group and alkylsulfanylphenyl group as the fourth substituent include a same option as the alkylsulfanyl group, arylsulfanyl group and alkylsulfanylphenyl group of $R^{21}$ described later.

Any one methylene group of the alkyl group in the fourth substituent may be substituted with —C(=O)— group or —O—C(=O)— group. However, in the fourth substituent, the —C(=O)— group and the —O—C(=O)— group are preferably not directly bonded to $Ar^{11}$ and $Ar^{12}$. Further, the fourth substituent preferably does not have a continuous bonding of heteroatoms such as —O—O—, —S—S— and —S—O—.

When the fourth substituent is the alkoxy group, the alkoxyphenyl group, the alkylsulfanyl group, the arylsulfanyl group or the alkylsulfanylphenyl group, the fourth substituent is preferably bonded to the ortho position and/or the para position of the phenylene group which is $Ar^{11}$ and $Ar^{12}$. In that case, a number of the substituent is preferably 3 or less.

$R^{21}$ in the formula (7) is any one selected from the group consisting of an alkylsulfanyl group which may have a substituent, an arylsulfanyl group which may have a substituent and an alkylsulfanylphenyl group which may have a substituent.

Specifically, the alkylsulfanyl group of $R^{21}$ is preferably an alkylsulfanyl group having 1 to 20 carbon atoms such as a methylsulfanyl group, an ethylsulfanyl group, an n-propylsulfanyl group, an n-butylsulfanyl group and the like, and more preferably an alkylsulfanyl group having 1 to 12 carbon atoms.

Specific examples of the arylsulfanyl group of $R^{21}$ include a phenylsulfanyl group, a naphthylsulfanyl group and the like.

Specific examples of the alkylsulfanylphenyl group of $R^{21}$ include preferably a phenyl group to which an alkylsulfanyl group having 1 to 20 carbon atoms is bonded, such as a methylsulfanylphenyl group, an ethylsulfanylphenyl group, a propylsulfanylphenyl group, a butylsulfanylphenyl group and the like, and more preferably a phenyl group to which an alkylsulfanyl group having 1 to 12 carbon atoms is bonded. A substitution position of the alkylsulfanyl group bonded to the phenylene group in $R^{21}$ is not particularly limited, but the para position is preferable from a viewpoint of increasing the electron donating property and the molar absorption coefficient at 365 nm. $R^{21}$ is preferably bonded to the ortho or para position of the phenylene group which is $Ar^{11}$.

$R^{22}$ in the formula (7) is an alkyl group or an aryl group which may have a substituent, and selected from a same options as each of those in the above $R^{11}$.

$R^{21}$ and $R^{22}$ in the formula (7) may have a substituent, and the substituent, hereinafter the substituent of $R^{21}$ and $R^{22}$ is referred to as "fifth substituent", is not particularly limited, but an electron withdrawing group and the like can be used in addition to the fourth substituent. Examples of the electron withdrawing group include a nitro group, a sulfonyl group and the like. A polymer synthesized by polymerizing $R^{21}$ or $R^{22}$ into which a polymerizable group is introduced may be used as a polymer to which a sensitizing function is imparted. The fifth substituent may have a polymer main chain. Examples of the polymerizable group include a (meth)acryloyloxy group, an epoxy group, a vinyl group and the like.

When W in the formula (7) is an oxygen atom or a sulfur atom, W is preferably at the ortho position or para position of $Ar^{12}$. When W is a direct bond, W is preferably at the ortho position or para position of $Ar^{12}$.

A total number of carbon atoms of $R^{21}$ in the formula (7) is not particularly limited, but it is preferably 1 to 20 when $R^{21}$ has a substituent. A total number of carbon atoms of $R^{22}$ in the formula (7) is not particularly limited, but it is preferably 1 to 20 when $R^{22}$ has a substituent. When the photosensitizer precursor is a polymer, a total number of carbon atoms of $R^{21}$ and $R^{22}$ is preferably 1 to 20, excluding a portion containing the polymer main chain to be the fifth substituent.

Each of Y is independently an oxygen atom or a sulfur atom.

Each of $R^{23}$ and $R^{24}$ is any one independently selected from the group consisting of a linear, branched or cyclic alkyl group, alkenyl group, alkynyl group and aralkyl group which may have a substituent. The alkyl group and alkenyl group of $R^{23}$ and $R^{24}$ are selected from a same option as the alkyl group and alkenyl group of $R^{11}$ in the formula (1).

The alkynyl group of $R^{23}$ and $R^{24}$ is selected from those in which a part of the alkyl groups of $R^{23}$ and $R^{24}$ are replaced with a triple bond. The aralkyl group of $R^{23}$ and $R^{24}$ is selected from those in which a part of the hydrogen of the alkyl group of $R^{23}$ and $R^{24}$ is substituted with an aryl group such as a phenyl group, a naphthyl group or the like.

$R^{23}$ and $R^{24}$ in the formula (7) may have a substituent, and the substituent, hereinafter the substituent of $R^{23}$ and $R^{24}$ is referred to as "the sixth substituent", is not particularly limited, and examples thereof include an aryl group such as a phenyl group, a naphthyl group and the like in addition to the fifth substituent.

A total carbon number of $R^{23}$ and $R^{24}$ in the formula (7) is not particularly limited, and the photosensitizer precursor may be a constituent component of a polymer, but it is preferably 1 to 20 when $R^{23}$ or $R^{24}$ has a substituent.

$R^{23}$ and $R^{24}$ may be bonded each other to form a ring structure with two of Y in the formula. That is, the photosensitizer precursor according to an embodiment of the present invention is represented by a following formula (8). In the following formula (8), —$R^{25}$—$R^{26}$— is preferably —$(CH_2)_n$—, and n is an integer of 2 or more. n is not limited as long as n is 2 or more, but n is preferably 8 or less from a viewpoint of ease of synthesis. $R^{25}$ and $R^{26}$ correspond to those in which $R^{23}$ and $R^{24}$ in the formula (7) are bonded each other to form a ring.

[Chem. 33]

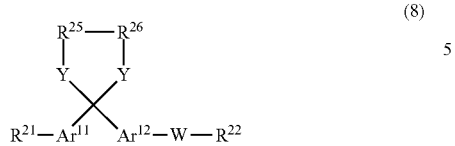

In the formula (8), $R^{25}$ and $R^{26}$ may have the same sixth substituent as $R^{23}$ and $R^{24}$. A polymer synthesized by polymerizing $R^{23}$ or $R^{24}$ into which a polymerizable group is introduced may be used as a polymer to which a sensitizing function is imparted.

A total carbon number of $R^{23}$ and $R^{24}$ is preferably 1 to 20. When the photosensitizer precursor is a polymer, the total number of carbon atoms of $R^{23}$ and $R^{24}$ is preferably 1 to 20, excluding the portion containing the polymer main chain to be the sixth substituent.

A photosensitizer precursor after acid treatment, that is, the photosensitizer having a carbonyl group formed when the photosensitizer precursor is deprotected with an acid preferably has a molar absorption coefficient at 365 nm of $1.0 \times 10^5$ cm$^2$/mol or more. A higher molar absorption coefficient at 365 nm is preferred, but $1.0 \times 10^{10}$ cm$^2$/mol or less is a realistic value. In order to obtain the molar absorption coefficient within the above-mentioned range, for example, one or more of an alkylsulfanyl group, an arylsulfanyl group, an alkylsulfanylphenyl group, or two or more of an alkoxy group or an aryloxy group are contained in the photosensitizer precursor.

In the present invention, a molar absorption coefficient is a value measured at 365 nm with UV-VIS absorption photometer using chloroform as a solvent.

From viewpoints of ease of synthesis and light absorption property, the photosensitizer precursor according to an embodiment of the present invention preferably has 4 or less of groups selected from the group consisting of an alkylsulfanyl group, an arylsulfanyl group, an alkoxyphenyl group, an alkylsulfanylphenyl group, an alkoxy group and an aryloxy group other than —Y—$R^{23}$ and —Y—$R^{24}$, or —Y—$R^{25}$—$R^{26}$—Y—.

Examples of the photosensitizer precursor represented by the formula (7) or (8) include following photosensitizer precursors. In the following examples, parenthesized parts represent polymer units. The photosensitizer precursor in some embodiments of the present invention is not limited thereto.

[Chem. 34]

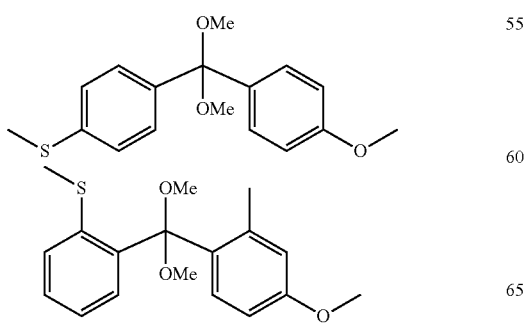

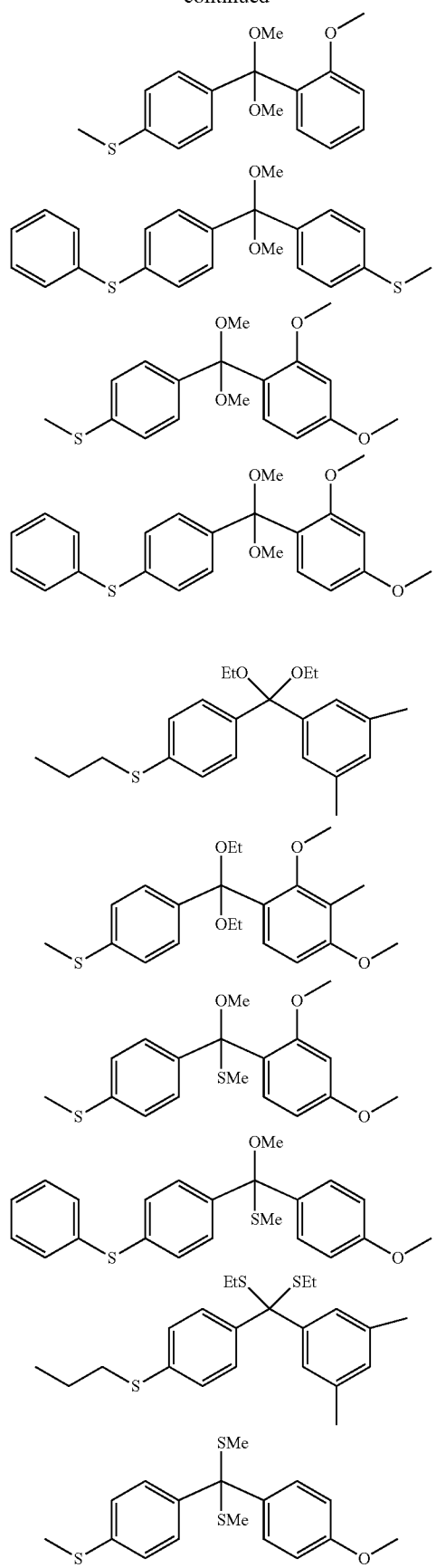

-continued
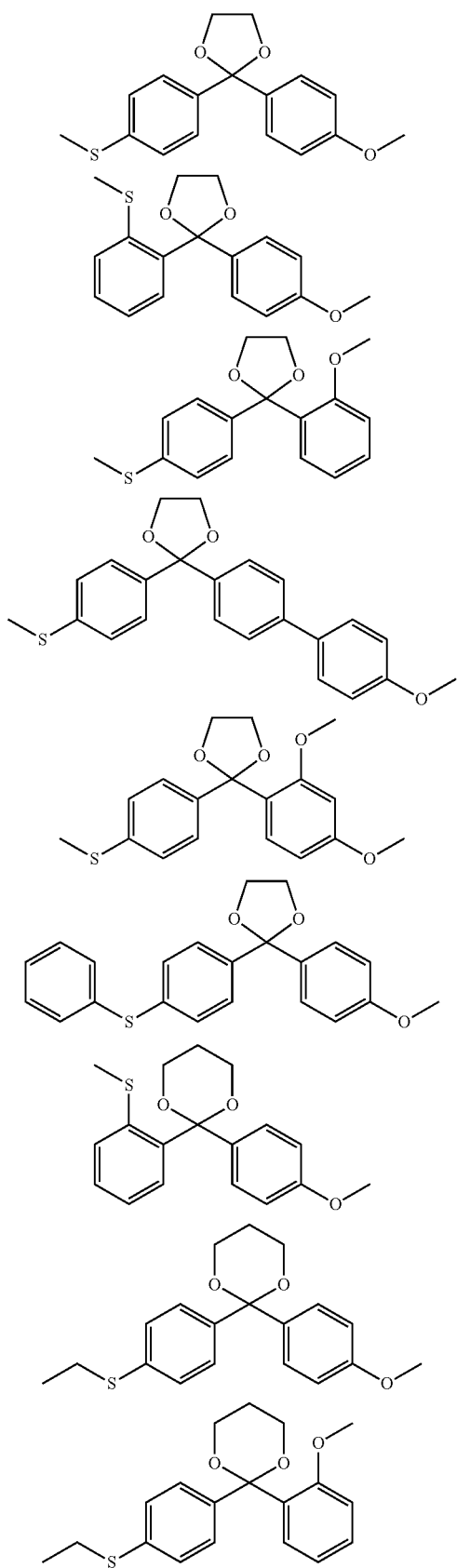
-continued
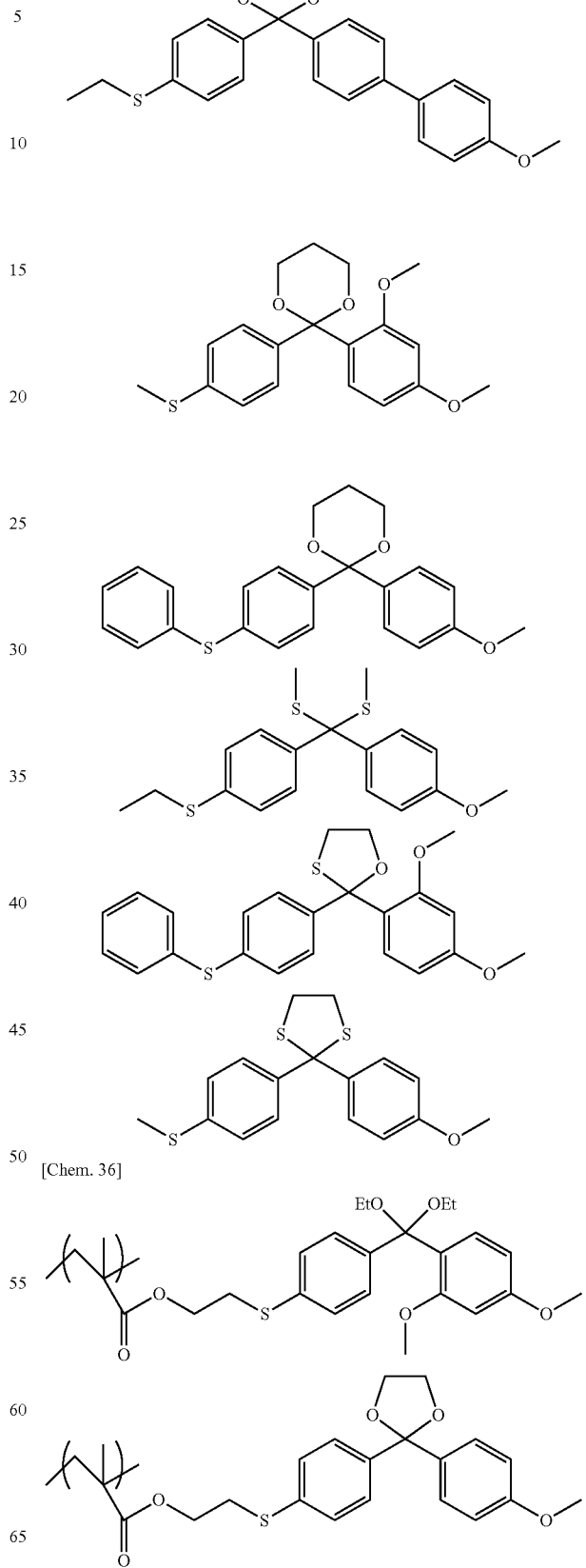

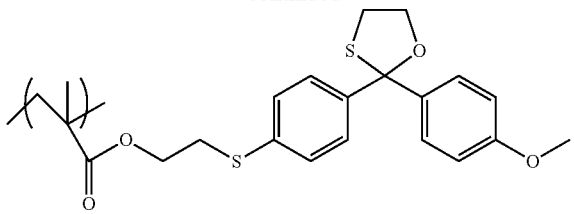

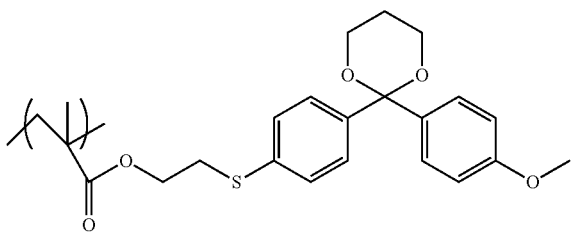

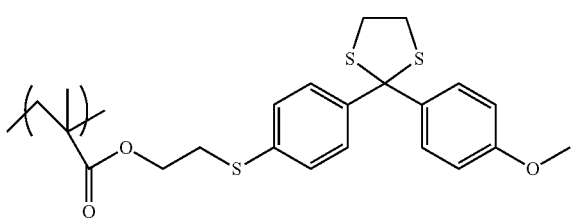

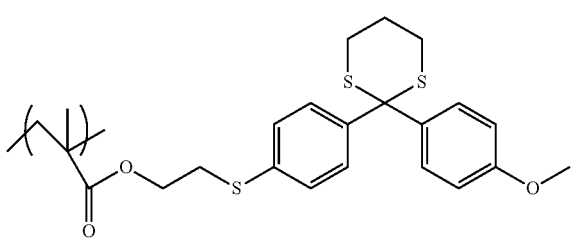

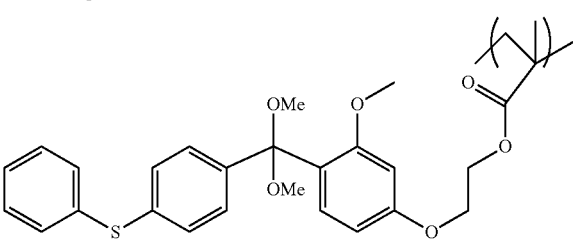

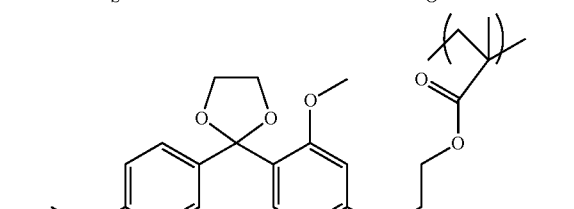

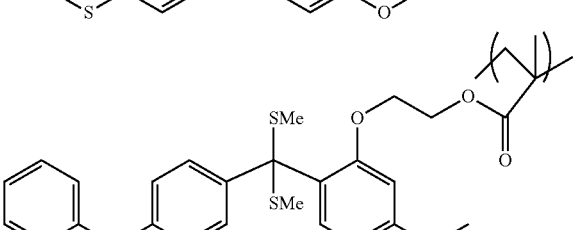

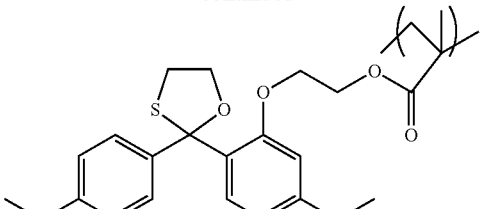

A method of synthesizing a photosensitizer precursor according to an embodiment of the present invention will be described. However, the present invention is not limited thereto.

When the photosensitizer precursor according to an embodiment of the present invention has a structure represented by a following formula (9), it can be synthesized, for example, by a following method. First, a reagent having —W—$R^{22}$ group and a halogenated benzene having $R^{21}$ group are reacted by Grignard reaction to obtain a benzophenone derivative, the reagent being one selected from the group consisting of: an alkoxybenzoyl chloride; an alkylbenzoyl chloride; a thioalkoxybenzoyl chloride; a thioalkylbenzoyl chloride; and those in which an alkyl group is an aryl group. Subsequently, the benzophenone derivative, an alcohol and optionally an orthoester such as a trialkyl orthoformate ($R^{23}$, $R^{24}$=alkyl group) as a dehydrating agent are reacted at 0° C. to reflux temperature for 1 to 120 hours to obtain a derivative represented by the following formula (9).

[Chem. 37]

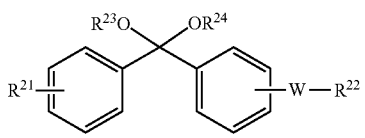

(9)

(Other Components)

In addition to the above components, the composition of an embodiment of the present invention may further contain, if necessary, an optional component such as an acid-diffusion controller, a surfactant, an organic carboxylic acid, an organic solvent, a dissolution inhibitor, a stabilizer, a dye, a polymer other than those described above and the like in combination.

The acid-diffusion controller controls a diffusion of the acid generated from the photoacid generator in the resist film, and has an effect of suppressing an undesirable chemical reaction in an unexposed portion. The storage stability of the resulting resist composition and the resolution as a resist is further improved, and the line width change of the resist pattern due to fluctuation of the time elapsed from exposure until development process can be suppressed. Therefore, the resist composition excellent in process stability can be obtained.

Examples of the acid-diffusion controller include a compound having one, two or three nitrogen atoms in the same molecule, an amide group-containing compound, a urea compound, a nitrogen-containing heterocyclic compound and the like. As the acid-diffusion controller, a photodegradable base to be sensitized by exposure and generates a weak acid may be used. Examples of the photodegradable base include an onium salt compound and an iodonium salt compound which decompose upon exposure to lose acid-diffusion controllability.

Specific examples of the acid-diffusion controller include the compounds described in Japanese Patent No.3577743, JP2001-215689, JP2001-166476, JP2008-102383, JP2010-243773, JP2011-37835 and JP2012-173505.

A content of the acid-diffusion controller is preferably 0.01 to 10 parts by mass, more preferably 0.03 to 5 parts by mass, and even more preferably 0.05 to 3 parts by mass, with respect to 100 parts by mass of the resist composition component.

The surfactant is preferably used for improving coatability. Examples of the surfactant include nonionic surfactants such as polyoxyethylene alkyl ethers, polyoxyethylene alkylallyl ethers, polyoxyethylene polyoxypropylene block copolymers, sorbitan fatty acid esters, polyoxyethylene sorbitan fatty acid ester and the like; fluorine-based surfactants; organosiloxane polymers; and the like.

A content of the surfactant is preferably 0.0001 to 2 parts by mass, and more preferably 0.0005 to 1% by mass with respect to 100 parts by mass of the resist composition component.

Examples of the organic carboxylic acid include an aliphatic carboxylic acid, an alicyclic carboxylic acid, an unsaturated aliphatic carboxylic acid, an oxycarboxylic acid, an alkoxycarboxylic acid, a ketocarboxylic acid, a benzoic acid derivative, phthalic acid, terephthalic acid, isophthalic acid, 2-naphthoic acid, 1-hydroxy-2-naphthoic acid, 2-hydroxy-3-naphthoic acid and the like. When the electron beam exposure is performed under vacuum, there is a risk of being volatilized from the surface of the resist film and contaminating an inside of the writing chamber. Therefore, the organic carboxylic acid is preferably the aromatic organic carboxylic acid, particulary benzoic acid, 1-hydroxy-2-naphthoic acid and 2-hydroxy-3-naphthoic acid.

A content of the organic carboxylic acid is preferably 0.01 to 10 parts by mass, more preferably 0.01 to 5 parts by mass, even more preferably 0.01 to 3 parts by mass with respect to 100 parts by mass of the resist composition component.

Examples of the organic solvent preferably include ethylene glycol monoethyl ether acetate, cyclohexanone, 2-heptanone, propylene glycol monomethyl ether (PGME), propylene glycol monomethyl ether acetate (PGMEA), propylene glycol monomethyl ether propionate, propylene glycol monoethyl ether acetate, methyl 3-methoxypropionate, ethyl 3-ethoxypropionate, methyl β-methoxyisobutyrate, ethyl butyrate, propyl butyrate, methyl isobutyl ketone, ethyl acetate, isoamyl acetate, ethyl lactate, toluene, xylene, cyclohexyl acetate, diacetone alcohol, N-methyl pyrrolidone, N,N-dimethylformamide, γ-butyrolactone, N,N-dimethylacetamide, propylene carbonate, ethylene carbonate and the like. These organic solvents are used solely or in combination.

The resist composition component is preferably dissolved in the organic solvent and dissolved at a solid concentration of 1 to 40% by mass, more preferably 1 to 30% by mass, and even more preferably 3 to 20% by mass. By setting the range of the solid concentration as described above, the above-mentioned film thickness can be achieved.

When the resist composition according to an embodiment of the present invention contains a polymer, a weight average molecular weight of the polymer is preferably 2000 to 200000, more preferably 2000 to 50000, and even more preferably 2000 to 15000. From a viewpoint of sensitivity, a dispersity (molecular weight distribution) (Mw/Mn) of the polymer is preferably 1.0 to 1.7, and more preferably 1.0 to 1.2. The weight average molecular weight and the dispersity of the polymer are defined as polystyrene equivalent values by GPC measurement.

The composition according to an embodiment of the present invention is obtained by mixing each component of the composition, and the mixing method is not particularly limited.

<4>Method of Manufacturing Device

An embodiment of the present invention is a method of manufacturing a device, including: formimg a resist film by, for example, applying the composition to a substrate; irradiating the resist film with a first active energy ray; irradiating a resist film after irradiating the first active energy ray, with a second active energy ray; and obtaining a pattern by developing a resist film after irradiating with the second active energy ray.

An embodiment of the present invention may be a method of manufacturing a substrate having a pattern before obtaining a singulated chip, including: formimg a resist film with the composition; irradiating with a first active energy ray; irradiating with a second active energy ray; and forming a pattern.

An embodiment of the present invention may be a method of manufacturing a device, including: forming a coating film on a substrate with the composition; and obtaining an interlayer insulating film by exposure of the coating film with a first active energy ray and a second active energy ray.

The first active energy ray and the second active energy ray are not particularly limited as long as the onium salts according to some embodiments of the present invention do not have significant absorption in the second active energy ray, but a wavelength of the first active energy ray is preferably shorter than that of the second active energy ray, or an energy of a photon or particle beam of the first active energy ray is preferably higher than that of the second active energy ray. Although each active energy ray is exemplified below, it is not limited to followings as long as the wavelength of the first active energy ray is shorter than the second active energy ray, or the energy of the photon or particle beam of the first active energy ray is higher than that of the second active energy ray.

The first active energy ray is not particularly limited as long as it can generate an active species such as an acid and the like in the resist film after irradiating the resist film. Preferred examples of the first active energy ray include KrF excimer laser, ArF excimer laser, electron beam or extreme ultraviolet (EUV) and the like.

The second active energy ray may be a light which can generate an active species such as an acid or the like by activation of the ketone derivative formed by deprotecting the acetal or thioacetal moiety of the onium salt according to some embodiments of the present invention. The activation of the ketone derivative is achieved by an acid generated in the resist film after irradiation with the first active energy ray.

For example, it means KrF excimer laser, UV, visible light and the like, and UV light within a range of 365 nm (i-line) to 436 nm (g-line) is preferable.

The substrate is not particularly limited, and a known substrate may be used. Examples of the substrate include: a substrate made of a metal such as silicon, silicon nitride, titanium, tantalum, palladium, copper, chromium or aluminum; a glass substrate; and the like.

In an embodiment of the present invention, an active energy ray used for exposure in a photolithography step used for obtaining an interlayer insulating film or the like for making LSI may be preferably UV, KrF excimer laser, ArF excimer laser, electron beam, extreme ultraviolet (EUV) or the like.

A dose of the first active energy ray varies depending on a kind and blending ratio of each component in the photo-curable composition, the film thickness of the coating film and the like, but is preferably 1 J/cm$^2$ or less, or 1000 µC/cm$^2$ or less.

In an embodiment of the present invention, the thickness of the resist film formed from the resist composition is preferably 10 to 200 nm. The resist composition is applied to a substrate by a suitable coating method such as spin coating, roll coating, flow coating, dip coating, spray coating, doctor coating or the like, and a thin film is formed by pre-baking at 60 to 150 ° C. for 1 to 20 minutes, and preferably at 80 to 120 ° C. for 1 to 10 minutes. The thickness of the coating film is 5 to 200 nm, and preferably 10 to 100 nm.

EXAMPLES

Hereinafter, the present invention will be described in more detail by examples, but the present invention is not limited by these examples at all.
<1>Synthesis of Sulfonium Salt
<Synthesis of Sulfonium Salt 1>

Synthesis Example 1

Synthesis of 4-fluoro-4'-methylsulfanylbenzophenone

4-Bromothioanisole (8.0 g) is dissolved in tetrahydrofuran (32 g), and a 1 mol/L THF solution (39 ml) of methylmagnesium bromide is added dropwise thereto at 5° C. or lower. After dropwise addition, a mixture is stirred at 35° C. for 30 minutes to obtain a THF solution of 4-methylsulfanylphenylmagnesium bromide. 4-Fluorobenzoyl chloride (7.0 g) is dissolved in THF (15 g), the THF solution of 4-methylsulfanylphenylmagnesium bromide is added dropwise thereto at 10° C. or lower, and a mixture is stirred at 25° C. for 1 hour. After stirring, 10% by mass of aqueous solution (50 g) of ammonium chloride is added thereto at 20° C. or lower, a mixture is further stirred for 10 minutes, and an organic layer is extracted with ethyl acetate (80 g). An extract is washed with water, and then ethyl acetate and tetrahydrofuran are evaporated to obtain a crude crystal. The crude crystal is recrystallized with ethanol (120 g) to obtain 4-fluoro-4'-methylsulfanylbenzophenone (6.1 g).

[Chem. 38]

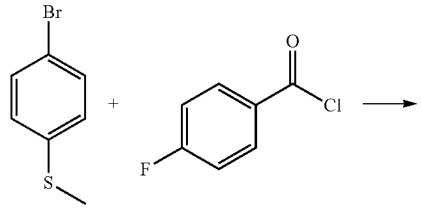

Synthesis Example 2

Synthesis of 4-methylsulfanyl-4'-phenylsulfanylbenzophenone

4-Fluoro-4'-methylsulfanylbenzophenone (6.0 g) obtained in Synthesis Example 1 is dissolved in DMF (30 g), thiophenol (3.2 g) and potassium carbonate (4.0 g) are added thereto, and a mixture is stirred at 70° C. for 4 hours. After stirring, pure water (90 g) is added thereto, a mixture is further stirred for 10 minutes, and an organic layer is extracted with toluene (60 g). An extract is washed three times with water, and then toluene is evaporated to obtain a crude crystal. The crude crystal is recrystallized with ethanol (40 g) to obtain 4-methylsulfanyl-4'-phenylsulfanylbenzophenone (5.6 g).

[Chem. 39]

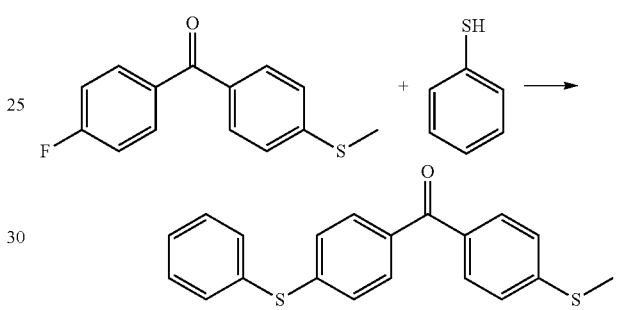

Synthesis Example 3

Synthesis of dimethyl-[4-(4-phenylsulfanyl) benzoylphenyl]sulfonium-nonafluorobutanesulfonate 4-Methylsulfanyl-4'-phenylsulfanylbenzophenone (3.0 g) obtained in Synthesis Example 2 is dissolved in acetonitrile (20 g), dimethyl sulfate (2.8 g) is added thereto, and a mixture is stirred at 70° C. for 4 hours. After stirring, pure water (60 g) is added thereto, a mixture is further stirred for 10 minutes, and washed with toluene (40 g). To an obtained aqueous layer, potassium nonafluorobutanesulfonate (3.0 g) and methylene chloride (30 g) are added, and a mixture is stirred for about 1 hour. A stirred mixture is phase-separated, washed three times with water, and then methylene chloride is evaporated to obtain a crude crystal. The crude crystal is purified by silica gel column chromatography (methylene chloride/methanol=90/10 (volume ratio)) to obtain dimethyl-[4-(4-phenylsulfanyl) benzoylphenyl]sulfonium-nonafluorobutanesulfonate (4.9 g).

[Chem. 40]

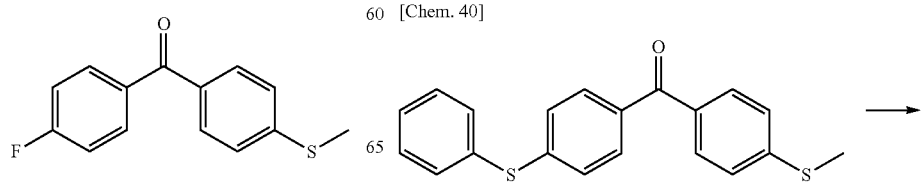

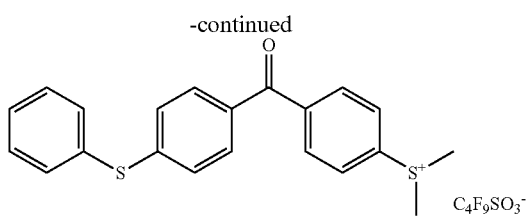

Synthesis Example 4

Synthesis of {4-[dimethoxy-(4-phenylsulfanylphenyl)methyl]phenyl}dimethylsulfonium-nonafluorobutanesulfonate (Sulfonium Salt 1)

Dimethyl-[4-(4-phenylsulfanyl) benzoylphenyl]sulfonium-nonafluorobutanesulfonate (1.0 g) obtained in Synthesis Example 3 is dissolved in methanol (2.5 g), trimethyl orthoformate (1.0 g) and concentrated sulfuric acid (4.0 mg) are added thereto, and a mixture is stirred at 60° C. for 2 hours. After stirring, a reaction solution is added to a mixed solution of methylene chloride (30 g) and 3% by mass of aqueous solution (10 g) of sodium hydrogen carbonate, a mixture is stirred for 10 minutes, and an organic layer is recovered. The obtained organic layer is washed three times with water, and then methylene chloride is evaporated to obtain {4-[dimethoxy-(4-phenylsulfanylphenyl)methyl]phenyl}dimethylsulfonium-nonafluorobutanesulfonate (1.0 g).

[Chem. 41]

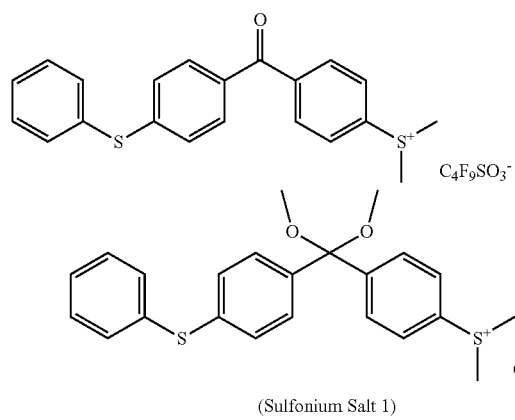

<Synthesis of Sulfonium Salt 2>

Synthesis Example 5

Synthesis of {4-[diethoxy-(4-phenylsulfanylphenyl)methyl]phenyl}dimethylsulfonium-nonafluorobutanesulfonate (Sulfonium Salt 2)

{4-[Diethoxy-(4-phenylsulfanylphenyl)methyl]phenyl}dimethylsulfonium-nonafluorobutanesulfonate (1.2 g) is obtained in the same procedure as Synthesis Example 4 except that ethanol is used instead of methanol and triethyl orthoformate is used instead of trimethyl orthoformate.

[Chem. 42]

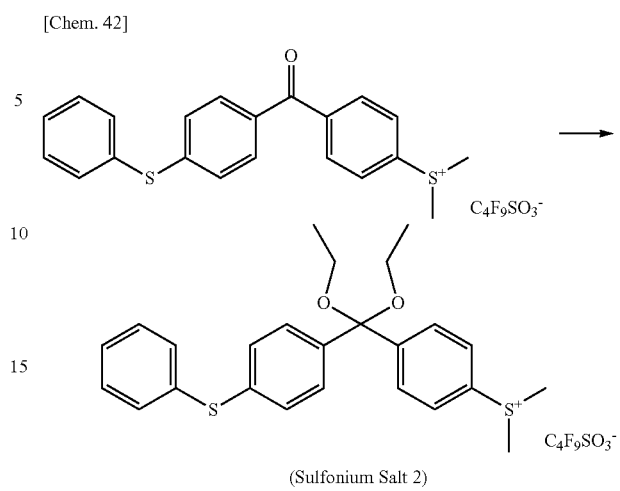

<Synthesis of Sulfonium Salt 3>

Synthesis Example 6

Synthesis of ethyl-[4-(4-phenylsulfanylbenzoyl) phenyl]methylsulfonium-4-(3-hydroxyadamantylcarbonyloxy)-1,1,2-trifluorobutanesulfonate Ethyl-[4-(4-phenylsulfanylbenzoyl) phenyl]methylsulfonium-4-(3-hydroxyadamantylcarbonyloxy)-1,1,2-trifluorobutanesulfonate (5.1 g) is obtained in the same procedure as Synthesis Example 3 except that diethyl sulfate is used instead of dimethyl sulfate and sodium 4-(3-hydroxyadamantylcarbonyloxy)-1,1,2-trifluorobutanesulfonate is used instead of potassium nonafluorobutanesulfonate. A molar absorption coefficient at 365 nm of the obtained compound is $1.0 \times 10^6$ cm$^2$/mol or greater.

[Chem. 43]

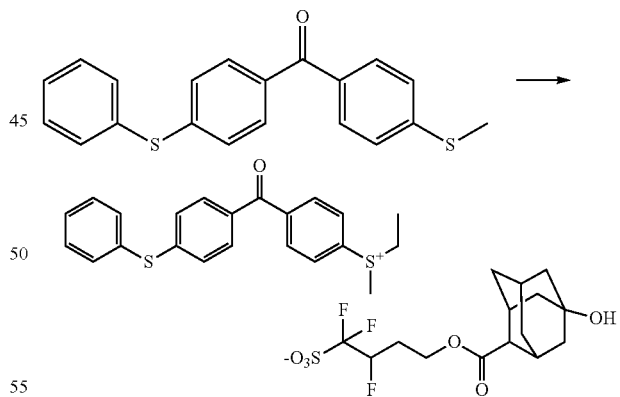

Synthesis Example 7

Synthesis of {4-[dimethoxy-(4-phenylsulfanylphenyl)methyl]phenyl}ethylmethylsulfnoium-4-(3-hydroxyadamantylcarbonyloxy)-1,1,2-trifluorobutanesulfonate (Sulfonium Salt 3)

{4-[Dimethoxy-(4-phenylsulfanylphenyl)methyl]phenyl}ethylmethylsulfonium-4-(3-hydroxyadamantylcarbonyloxy)-1,1,2-trifluorobutanesulfonate (1.1 g) is obtained in the same procedure as Synthesis Example 4 except that ethyl-[4-(4-phenylsulfanylbenzoyl) phenyl]methylsulfonium-4-(3-hydroxyadamantylcarbonyloxy)-1,1,2-trifluorobutanesulfonate is used instead of {4-[dimethoxy-(4-phenylsulfanylphenyl)methyl]phenyl}dimethylsulfonium-nonafluorobutanesulfonate. A molar absorption coefficient at 365 nm of the obtained compound is 1.0×10⁵ cm²/mol or smaller, which is one-tenth or smaller in comparison with that of ethylmethyl-[4-(4-phenylsulfanyl-benzoyl) phenyl]sulfonium-4-(3-hydroxyadamantylcarbonyloxy)-1,1,2-trifluorobutanesulfonate obtained in Synthesis Example 6.

Synthesis Example 9

Synthesis of {4-[4-(4-methoxyphenylsulfanyl)benzoyl]phenyl}-dimethyl-sulfonium-camphorsulfonate Dimethyl-{4-[4-(4-methoxyphenylsulfanyl) benzoyl] phenyl}sulfonium-camphorsulfonate (4.3 g) is obtained in the same procedure as Synthesis Example 3 except that 4-methylsulfanyl-4'-(4-methoxyphenylsulfanyl)benzophenone is used instead of 4-methylsulfanyl-4'-phenylsulfanyl-benzophenone and sodium (±)-10-camphorsulfonate is used

[Chem. 44]

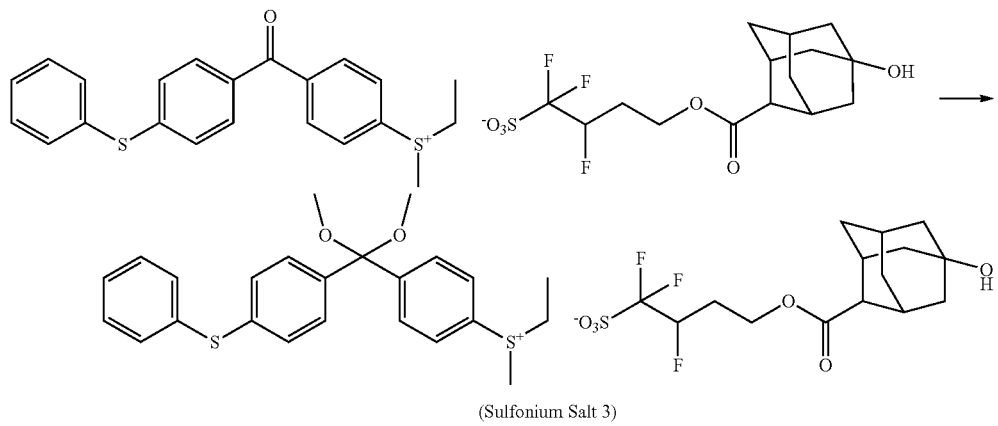

(Sulfonium Salt 3)

<Synthesis of Sulfonium Salt 4>

Synthesis Example 8

Synthesis of 4-methylsulfanyl-4'-(4-methoxyphenylsulfanyl)benzophenone

4-Methylsulfanyl-4'-(4-methoxyphenylsulfanyl)benzophenone (4.6 g) is obtained in the same procedure as Synthesis Example 2 except that 4-methoxythiophenol is used instead of thiophenol.

[Chem. 45]

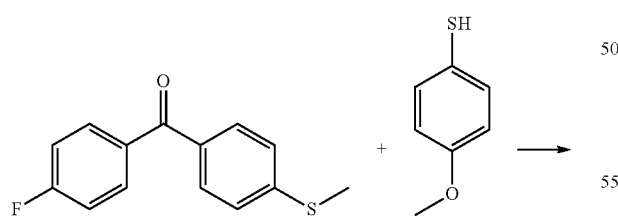

instead of potassium nonafluorobutanesulfonate. A molar absorption coefficient at 365 nm of the obtained compound is 3.0×10⁶ cm²/mol or greater.

[Chem. 46]

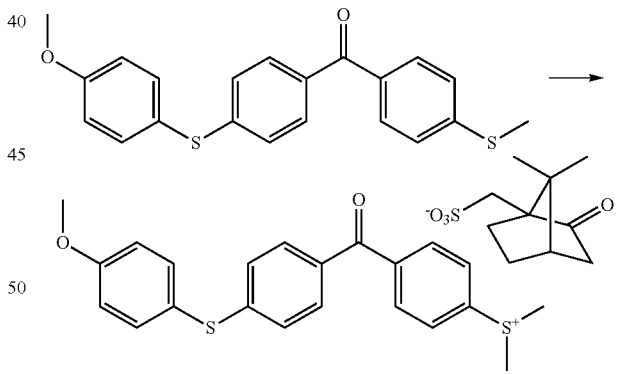

Synthesis Example 10

Synthesis of {4-{dimethoxy-[4-(4-methoxyphenylsulfanyl)phenyl]methyl}phenyl}dimethylsulfonium-camphorsulfonate (Sulfonium Salt 4)

Dimethyl-{4-[4-(4-methoxyphenylsulfanyl) benzoyl] phenyl}sulfonium-camphorsulfonate (1.0 g) is dissolved in methanol (2.5 g), trimethyl orthoformate (1.0 g) and (+/−)-10-camphorsulfonic acid (50 mg) are added thereto, and a mixture is stirred at 60° C. for 6 hours. After stirring, a reaction solution is added to a mixed solution of methylene chloride (30 g) and 3% by mass of aqueous solution (10 g) of sodium hydrogen carbonate, a mixture is stirred for 10 minutes, and an organic layer is recovered. The obtained organic layer is washed three times with water, and then methylene chloride is evaporate to obtain {4-{dimethoxy-[4-(4-methoxyphenylsulfanyl)phenyl]methyl}phenyl}dimethylsulfonium-camphorsulfonate (1.0 g). A molar absorption coefficient at 365 nm of the obtained compound is $1.0 \times 10^5$ cm$^2$/mol or smaller, which is one-tenth or smaller in comparison with that of dimethyl-{4-[4-(4-methoxyphenylsulfanyl)benzoyl]phenyl}-sulfonium-camphorsulfonate obtained in Synthesis Example 9.

[Chem. 47]

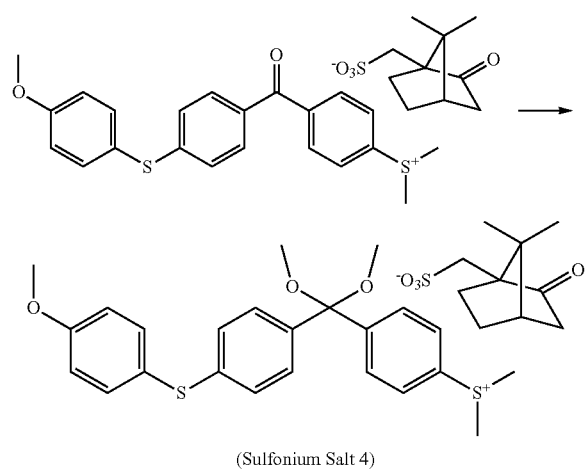

(Sulfonium Salt 4)

<Synthesis of Sulfonium Salt 5>

Synthesis Example 11

Synthesis of 2-phenylsulfanylbenzoic acid

2-Mercaptobenzoic acid (9.2 g) is dissolved in DMF (60 g), bromobenzene (9.4 g), potassium carbonate (10 g) and copper (I) chloride (6.0 g) are added thereto, and a mixture is stirred at 90° C. for 6 hours. After stirring, pure water (180 g) is added thereto, a mixture is further stirred for 10 minutes, and an organic layer is extracted with methylene chloride (120 g). An extract is washed three times with water, and then methylene chloride is evaporated to obtain a crude crystal. The crude crystal is recrystallized with ethanol (80 g) to obtain 2-phenylsulfanylbenzoic acid (10.6 g).

[Chem. 48]

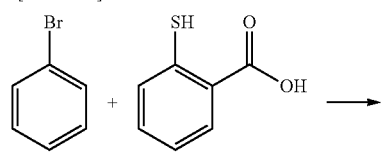

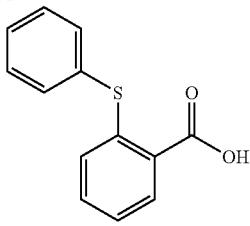

Synthesis Example 12

Synthesis of 2-phenylsulfanylbenzoyl chloride

Thionyl chloride (60 g) is added to 2-phenylsulfanylbenzoic acid (10.0 g) obtained in Synthesis Example 11, and a mixture is stirred at 60° C. for 4 hours. After stirring, thionyl chloride is evaporated under reduced pressure to obtain 2-phenylsulfanylbenzoyl chloride (10.8 g).

[Chem. 49]

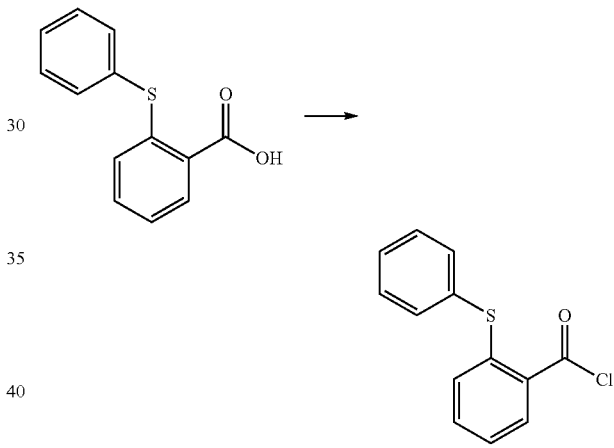

Synthesis Example 13

Synthesis of 4-methylsulfanyl-2'-phenylsulfanylbenzophenone

4-Methylsulfanyl-2'-phenylsulfanylbenzophenone (6.5 g) is obtained in the same procedure as Synthesis Example 1 except that 2-phenylsulfanylbenzoyl chloride is used instead of 4-fluorobenzoyl chloride.

[Chem. 50]

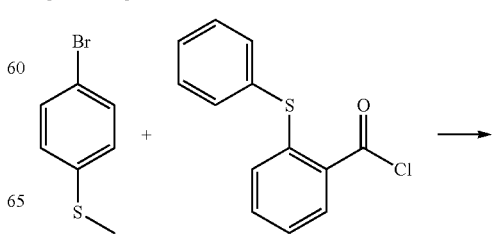

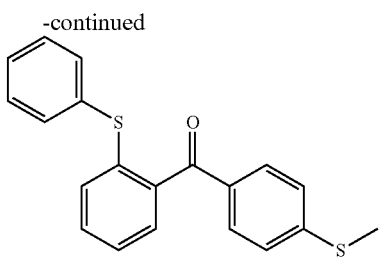

Synthesis Example 14

Synthesis of dimethyl-[4-(2-phenylsulfanylbenzoyl) phenyl]sulfonium-methylsulfate 4-Methylsulfanyl-2'-phenylsulfanylbenophenone (3.0 g) is dissolved in acetonitrile (10 g), dimethyl sulfate (2.8 g) is added thereto, and a mixture is stirred at 70° C. for 4 hours. After stirring, a reaction solution is added dropwise to ethyl acetate (40 g) to precipitate a solid. The solid is filtered, washed with ethyl acetate (10 g), and then dried to obtain dimethyl-[4-(2-phenylsulfanylbenzoyl) phenyl]sulfonium-methylsulfate (4.1 g). A molar absorption coefficient at 365 nm of the obtained compound is $5.0 \times 10^5$ cm$^2$/mol or greater.

[Chem. 51]

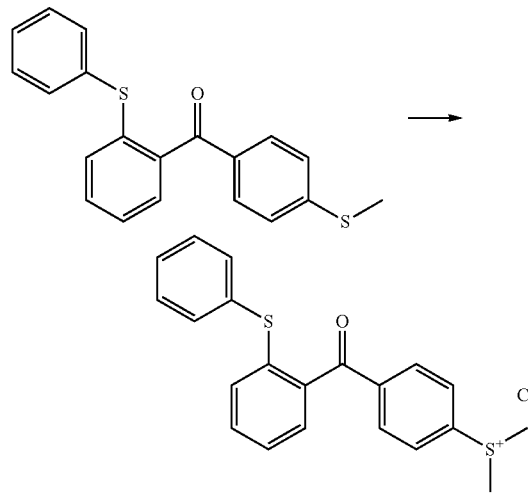

Synthesis Example 15

Synthesis of {4-[dimethoxy-(2-phenylsulfanylphenyl)methyl]phenyl}dimethylsulfonium-benzoate (Sulfonium Salt 5)

Dimethyl-[4-(2-phenylsulfanyl-benzoyl) phenyl]sulfonium-methylsulfate (3.0 g) obtained in Synthesis Example 14 is dissolved in methanol (7.5 g), trimethyl orthoformate (3.0 g) and concentrated sulfuric acid (12.0 mg) are added thereto, and a mixture is stirred at 60° C. for 2 hours. After stirring, a reaction solution is added dropwise to 3% by mass of aqueous solution (30 g) of sodium hydrogen carbonate. Then, methylene chloride (30 g) and sodium benzoate (3.0 g) are added thereto, and a mixture is further stirred for 3 hours. After stirring, phase separation is performed to recover an organic layer, the organic layer is washed three times with water, and then methylene chloride is evaporated to obtain a crude crystal. The crude crystal is purified by silica gel column chromatography (methylene chloride/methanol=90/10 (volume ratio), addition of 0.1% by mass triethylamine) to obtain {4-[dimethoxy-(2-phenylsulfanylphenyl)methyl]phenyl}dimethylsulfonium-benzoate (1.2 g). A molar absorption coefficient at 365 nm of the obtained compound is $1.0 \times 10^5$ cm$^2$/mol or smaller, which is one-fifth or smaller in comparison with that of dimethyl-[4-(2-phenylsulfanyl-benzoyl) phenyl]sulfonium-methylsulfate obtained in Synthesis Example 14.

[Chem. 52]

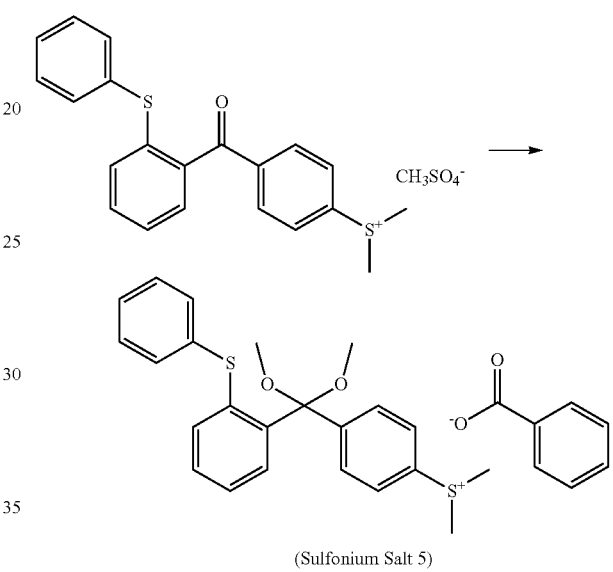

(Sulfonium Salt 5)

<Synthesis of Sulfonium Salt 6>

Synthesis Example 16

Synthesis of 2,4-dimethoxy-4'-fluorobenzophenone

Aluminum chloride (3.0 g) is added to methylene chloride (28 g), and set to 0° C. 2,4-Dimethoxybenzene (3.0 g) is added thereto, and then 4-fluorobenzoyl chloride (3.4 g) is dissolved in methylene chloride (6.8 g) to add dropwise thereto over 30 minutes. After dropwise addition, a mixture is stirred at 25° C. for 1 hour, pure water (60 g) is added thereto, a mixture is further stirred for 5 minutes, and extracted twice with toluene (20 g). A mixture is phase-separated to obtain an organic layer, and a solvent is evaporated. An obtained residue is purified by recrystallization with ethanol (30 g) to obtain 2,4-dimethoxy-4'-fluorobenzophenone (5.2 g).

[Chem. 53]

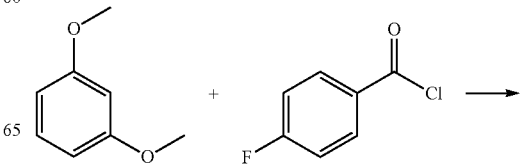

-continued

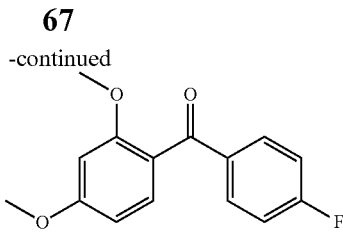

Synthesis Example 17

Synthesis of 2,4-dimethoxy-4'-(n-propylsulfanyl)benzophenone 2,4-Dimethoxy-4'-fluorobenzophenone obtained (5.0 g) in Synthesis Example 16 is dissolved in DMF (30 g), 1-propanethiol (1.6 g) and potassium carbonate (3.2 g) are added thereto, and a mixture is stirred 70° C. for 4 hours. After stirring, pure water (90 g) is added thereto, a mixture is further stirred for 10 minutes, and an organic layer is extracted with toluene (60 g). An extract is washed three times with water, and then toluene is evaporated to obtain a crude product. The crude product is purified by silica gel column chromatography (hexane/ethyl acetate=75/25 (volume ratio)) to obtain 2,4-dimethoxy-4'-(n-propylsulfanyl)benzophenone (4.8 g).

[Chem. 54]

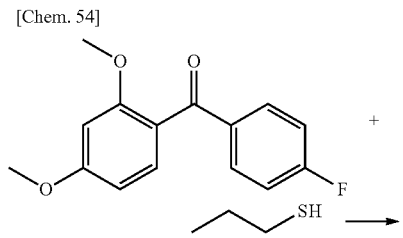

Synthesis Example 18

Synthesis of [4-(2,4-dimethoxybenzoyl) phenyl]ethyl-n-propylsulfonium-nonaflurobutanesulfonate

[4-(2, 4-Dimethoxybenzoyl)phenyl]ethyl-n-propylsulfonium-nonaflurobutanesulfonate (5.0 g) is obtained in the same procedure as Synthesis Example 3 except that 2,4-dimethoxy-4'-(n-propylsulfanyl)benzophenone is used instead of 4-methylsulfanyl-4'-phenylsulfanylbenzophenone and diethyl sulfate is used instead of dimethyl sulfate. A molar absorption coefficient at 365 nm of the obtained compound is $5.0 \times 10^5$ cm$^2$/mol or greater.

[Chem. 55]

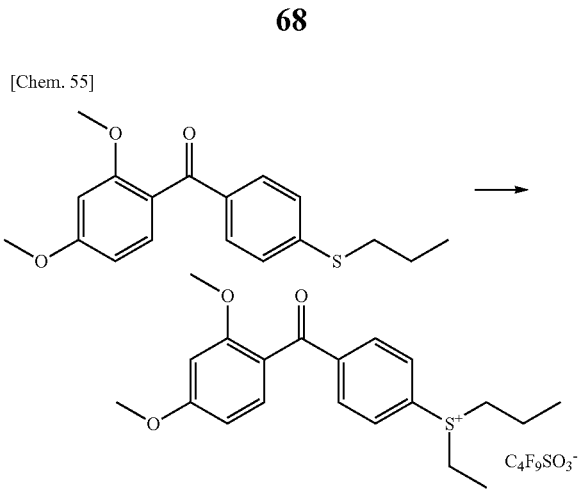

Synthesis Example 19

Synthesis of {4-[(2,4-dimethoxyphenyl)-dimethoxymethyl]phenyl}ethyl-n-propylsulfonium-nonafluorobutanesulfonate (Sulfonium Salt 6)

{4-[(2,4-Dimethoxyphenyl) dimethoxymethyl]phenyl}ethyl-n-propylsulfonium-nonafluorobutanesulfonate (5.1 g) is obtained in the same procedure as Synthesis Example 4 except that [4-(2,4-dimethoxybenzoyl)phenyl]ethyl-n-propylsulfonium-nonaflurobutanesulfonate is used instead of dimethyl-[4-(4-phenylsulfanylbenzoyl)phenyl]sulfonium-nonafluorobutanesulfonate. A molar absorption coefficient at 365 nm of the obtained compound is $1.0 \times 10^5$ cm$^2$/mol or smaller, which is one-fifth or smaller in comparison with that of {4-(2,4-dimethoxybenzoyl)phenyl}ethyl-n-propylsulfonium-nonafluorobutanesulfonate obtained in Synthesis Example 18.

[Chem. 56]

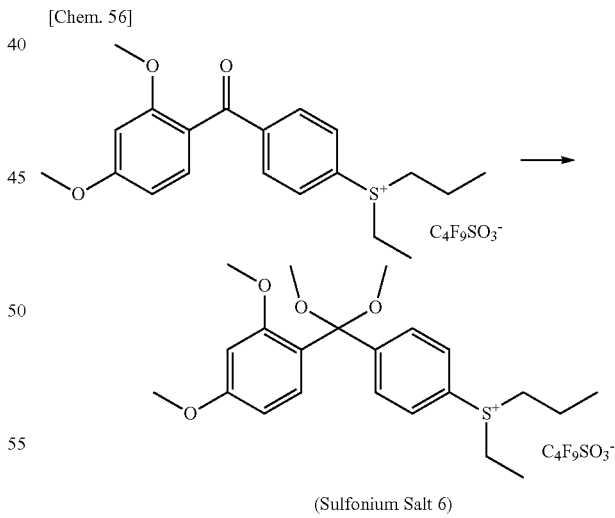

(Sulfonium Salt 6)

<Synthesis of Sulfonium Salt 7>

Synthesis Example 20

Synthesis of 4-bromo-4'-phenylsulfanylbenzophenone

Aluminum chloride (3.0 g) is dissolved in methylene chloride (28 g), and set to 0° C. Diphenyl sulfide (4.0 g) is added thereto, and then 4-bromobenzoyl chloride (3.4 g) is dissolved in methylene chloride (6.8 g) to add dropwise thereto over 30 minutes. After dropwise addition, a mixture is stirred at 25° C. for 1 hour, pure water (60 g) is added thereto, a mixture is further stirred for 5 minutes, and then washed twice with toluene (20 g). A mixture is phase-separated to obtain an organic layer, and a solvent is evaporated. An obtained residue is purified by recrystallization with isopropyl alcohol (30 g) to obtain 4-bromo-4'-phenylsulfanylbenzophenone (5.2 g).

[Chem. 57]

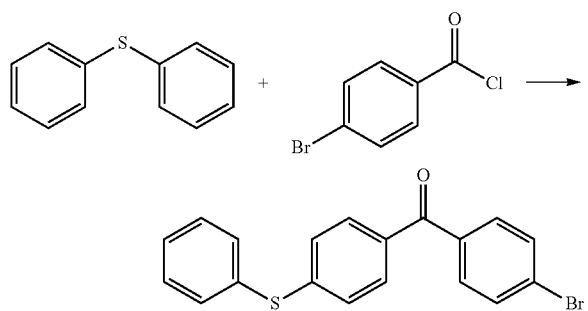

Synthesis Example 21

Synthesis of
4-bromo-4'-phenylsulfanylbenzophenone dimethyl acetal

4-Bromo-4'-phenylsulfanylbenzophenone (5.0 g) obtained in Synthesis Example 20 is dissolved in methanol (30 g), trimethyl orthoformate (5.0 g) and concentrated sulfuric acid (30 mg) are added thereto, and a mixture is stirred at 60° C. for 4 hours. After stirring, 3% by mass of aqueous solution (150 g) of sodium bicarbonate is added thereto, and a mixture is further stirred for 10 minutes to precipitate a solid. The precipitated solid is filtered, and re-dissolved in methylene chloride (30 g). A solution is washed three times with water, and then methylene chloride is evaporated to obtain 4-bromo-4'-phenylsulfanylbenzophenone dimethyl acetal (5.0 g).

[Chem. 58]

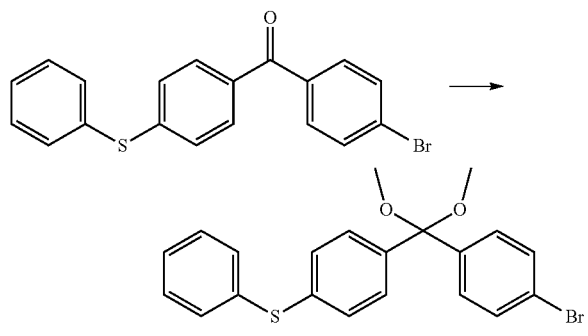

Synthesis Example 22

Synthesis of {4-[dimethoxy-(4-phenylsulfanylphenyl)methyl]phenyl}diphenylsulfonium-nonafluorobutanesulfonate (Sulfonium Salt 7)

To a flask dried in advance, tetrahydrofuran (2.0 g), magnesium (0.4 g) and 1,2-dibromoethane are added to activate magnesium. After check of the activation, a solution is heated to 50° C., and then 4-bromo-4'-phenylsulfanylbenzophenone dimethyl acetal (4.0 g) obtained in Synthesis Example 20 is dissolved in THF (6.0 g) to add dropwise thereto. After dropwise addition, a mixture is stirred at 50° C. for 5 hours to obtain a THF solution of 4-[dimethoxy-(4-phenylsulfanylphenyl)methyl]phenylmagnesium bromide. To a solution of diphenyl sulfoxide (1.9 g), trimethylsilyl chloride (1.8 g) and triethylamine (0.8 g) dissolved in methylene chloride (9.5 g), the THF solution of 4-[dimethoxy-(4-phenylsulfanylphenyl)methyl]phenylmagnesium bromide is added dropwise at 10° C. or lower, and then a mixture is stirred at 25° C. for 1 hour. After stirring, 10% by mass of aqueous solution (30 g) of ammonium chloride is added thereto at 5° C. or lower, a mixture is further stirred for 10 minutes, and washed twice with isopropyl ether (5.0 g). Thereafter, methylene chloride (40 g) and potassium nonafluorobutanesulfonate (3.1 g) are added thereto, and a mixture is stirred at 25° C. for about 2 hours. A stirred mixture is phase-separated, washed three times with water, and then methylene chloride is evaporated to obtain a crude crystal. The crude crystal is purified by silica gel column chromatography (methylene chloride/methanol=90/10 (volume ratio)) to obtain {4-[dimethoxy-(4-phenylsulfanylphenyl)methyl]phenyl}diphenylsulfonium-nonafluorobutanesulfonate (3.2 g). A molar absorption coefficient at 365 nm of the obtained compound is $1.0 \times 10^5$ cm$^2$/mol or smaller.

[Chem. 59]

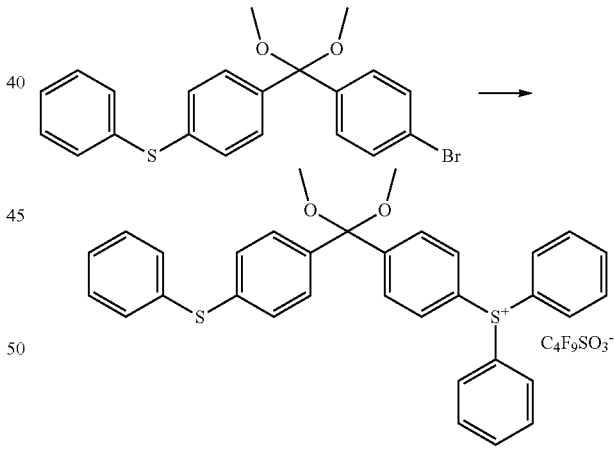

(Sulfonium Salt 7)

<Synthesis of Sulfonium Salt 8>

Synthesis Example 23

Synthesis of 2-(4-bromophenyl)-2-(4-phenylsulfanylphenyl)-[1,3]dioxolane 2-(4-Bromophenyl)-2-(4-phenylsulfanylphenyl)-[1,3]dioxolane (5.0 g) is obtained in the same procedure as Synthesis Example 21 except that ethylene glycol is used instead of methanol.

[Chem. 60]

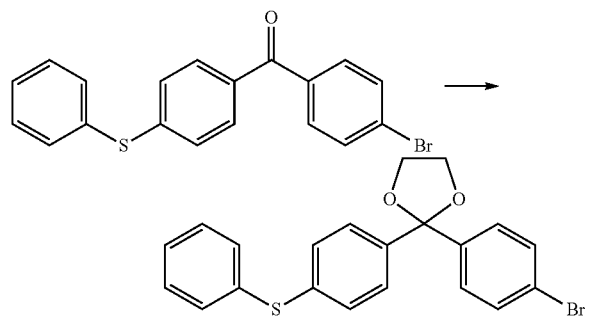

Synthesis Example 24

Synthesis of diphenyl-{4-[2-(4-phenylsulfanylphenyl)-[1,3]dioxolan-2-yl]phenyl}sulfonium-nonafluorobutanesulfonate (Sulfonium Salt 8)

Diphenyl-{4-[2-(4-phenylsulfanylphenyl)-[1,3]dioxolan-2-yl]phenyl}sulfonium-nonafluorobutanesulfonate (4.3 g) is obtained in the same procedure as Synthesis Example 22 except that 2-(4-bromophenyl)-2-(4-phenylsulfanylphenyl)-[1,3]dioxolane is used instead of 4-bromo-4'-phenylsulfanylbenzophenone dimethyl acetal. A molar absorption coefficient at 365 nm of the obtained compound is $1.0 \times 10^5$ cm$^2$/mol or smaller.

[Chem. 61]

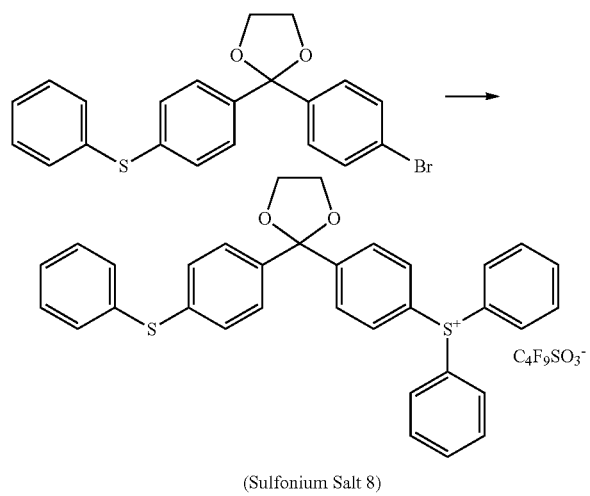

(Sulfonium Salt 8)

<Synthesis of Sulfonium Salt 9>

Synthesis Example 25

Synthesis of dibenzothiophene-5-oxide

Dibenzothiophene (15 g) is dissolved in formic acid (75 g), and 35% by mass of aqueous solution (8.7 g) of hydrogen peroxide is added dropwise with ice cooling. Then, a mixture is allow to reach room temperature, and stirred for 5 hours. After stirring, pure water (200 g) is added dropwise to a reaction mixture to precipitate a solid. The precipitated solid is filtered, washed three times with pure water (40 g), and then dried to obtain a crude crystal. The crude crystal is recrystallized with acetone (100 g) and ethanol (200 g) to obtain dibenzothiophene-5-oxide (12 g).

[Chem. 62]

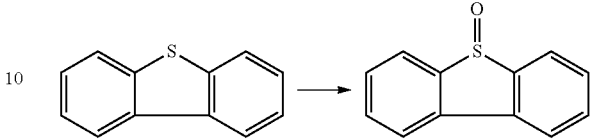

Synthesis Example 26

Synthesis of 5-{4-[dimethoxy-(4-phenylsulfanylphenyl) methyl]phenyl}dibenzothiophenium-nonafluorobutanesulfonate (Sulfonium Salt 9)

5-{4-[Dimethoxy-(4-phenylsulfanylphenyl)methyl] phenyl}dibenzothiophenium-nonafluorobutanesulfonate (4.0 g) is obtained in the same procedure as Synthesis Example 22 except that dibenzothiophene-5-oxide is used instead of diphenyl sulfoxide. A molar absorption coefficient at 365 nm of the obtained compound is $1.0 \times 10^5$ cm$^2$/mol or smaller.

[Chem. 63]

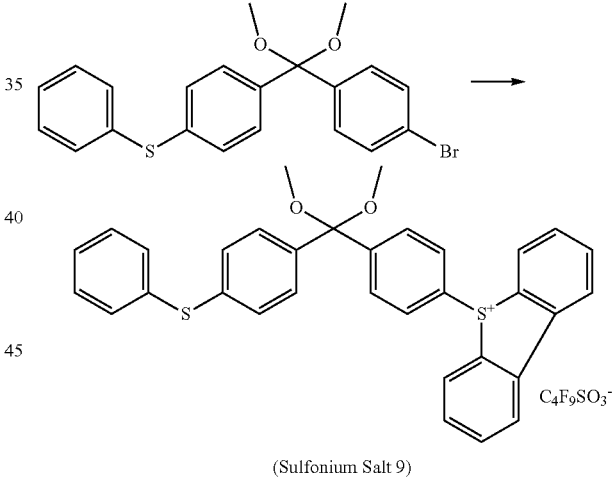

(Sulfonium Salt 9)

<Synthesis of Sulfonium Salt 10>

Synthesis Example 27

Synthesis of {4-[dimethoxy-(4-phenylsulfanylphenyl)methyl]phenyl}(di-p-tolyl)sulfonium-p-toluenesulfonate (Sulfonium Salt 10)

{4-[Dimethoxy-(4-phenylsulfanylphenyl)methyl]phenyl} (di-p-tolyl)sulfonium-p-toluenesulfonate (3.8 g) is obtained in the same procedure as Synthesis Example 22 except that p-tolyl sulfoxide is used instead of diphenyl sulfoxide and sodium p-toluenesulfonate is used instead of potassium nonafluorobutanesulfonate. A molar absorption coefficient at 365 nm of the obtained compound is $1.0 \times 10^5$ cm$^2$/mol or smaller.

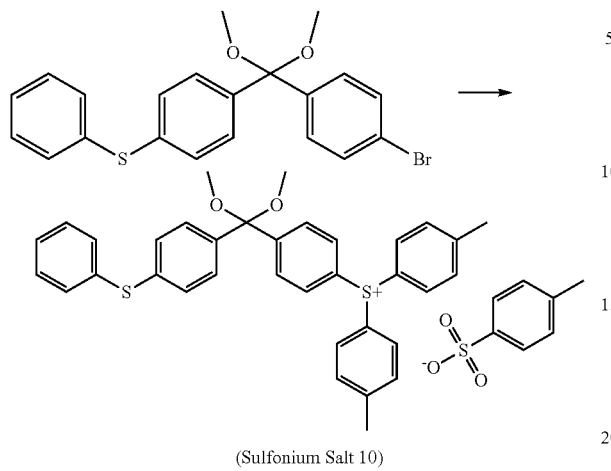

(Sulfonium Salt 10)

<Synthesis of Sulfonium Salt 11>

Synthesis Example 28

Synthesis of (6-methoxynaphthalen-2-yl)-(4-methylsulfanylphenyl)methanone (6-Methoxynaphthalen-2-yl)-(4-methylsulfanylphenyl)methanone (4.5 g) is obtained in the same procedure as Synthesis Example 1 except that 2-bromo-6-methoxynaphthalene is used instead of 4-bromoanisole and 4-(methylthio)benzoyl chloride is used instead of 4-fluorobenzoyl chloride.

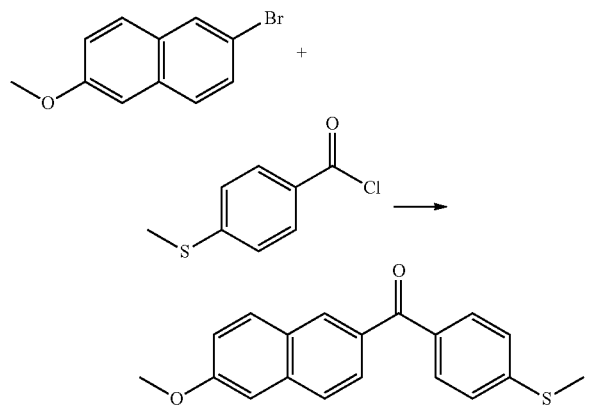

Synthesis Example 29

Synthesis of [4-(6-methoxynaphthalen-2-ylcarbonyl)phenyl]dimethylsulfonium-nonafluorobutanesulfonate (Sulfonium Salt 11)

[4-(6-Methoxynaphthalen-2-ylcarbonyl)phenyl]dimethylsulfonium-nonafluorobutanesulfonate (4.5 g) is obtained in the same procedure as Synthesis Example 3 except that (6-methoxynaphthalen-2-yl)-(4-methylsulfanylphenyl)methanone is used instead of 4-methylsulfanyl-4'-phenylsulfanylbenzophenone. A molar absorption coefficient at 365 nm of the obtained compound is $1.0 \times 10^6$ cm$^2$/mol or greater.

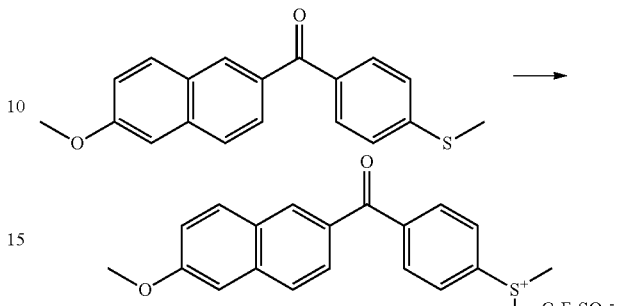

Synthesis Example 30

Synthesis of {4-[dimethoxy-(6-methoxynaphthalen-2-yl) methyl]phenyl}dimethylsulfonium-nonafluorobutanesulfonate (Sulfonium Salt 11)

{4-[Dimethoxy-(6-methoxynaphthalen-2-yl)methyl]phenyl}dimethylsulfonium-nonafluorobutanesulfonate (1.0 g) is obtained in the same procedure as Synthesis Example 4 except that {4-(6-methoxynaphthalen-2-ylcarbonyl)phenyl}dimethylsulfonium-nonafluorobutanesulfonate is used instead of dimethyl-[4-(4-phenylsulfanyl-benzoyl)phenyl]-sulfonium-nonafluorobutanesulfonate. A molar absorption coefficient at 365 nm of the obtained compound is $1.0 \times 10^5$ cm$^2$/mol or smaller, which is one-tenth or smaller in comparison with that of {4-(6-methoxynaphthalen-2-ylcarbonyl)phenyl}dimethylsulfonium-nonafluorobutanesulfonate obtained in Synthesis Example 29.

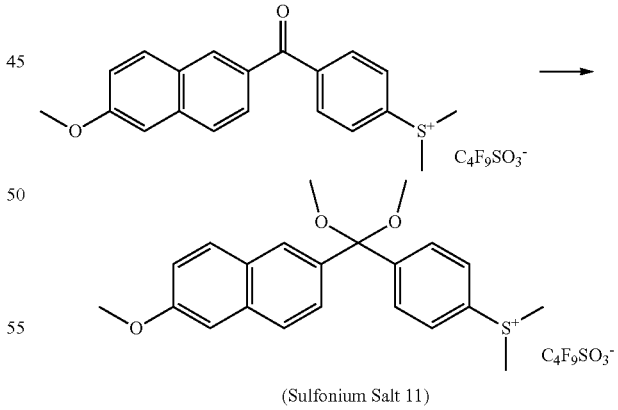

(Sulfonium Salt 11)

<Synthesis of Sulfonium Salt 12>

Synthesis Example 31

Synthesis of 6-bromonaphthoyl-2-chloride

6-Bromonaphthoyl-2-chloride (10.8 g) is obtained in the same procedure as Synthesis Example 12 except that 6-bromo-2-naphthalenecarboxylic acid is used instead of 2-phenylsulfanylbenzoic acid.

[Chem. 68]

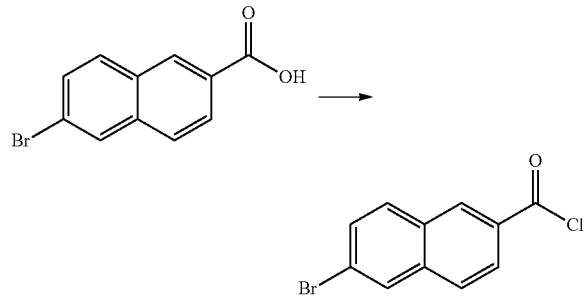

Synthesis Example 32

Synthesis of (6-bromonaphthalen-2-yl)-(4,7-dimethoxynaphthalen-1-yl)methanone (6-Bromonaphthalen-2-yl)-(4,7-dimethoxynaphthalen-1-yl)methanone (5.4 g) is obtained in the same procedure as Synthesis Example 20 except that 1,6-dimethoxynaphthalene is used instead of diphenyl sulfide and 6-bromonaphthoyl-2-chloride is used instead of 4-bromobenzoyl chloride.

[Chem. 69]

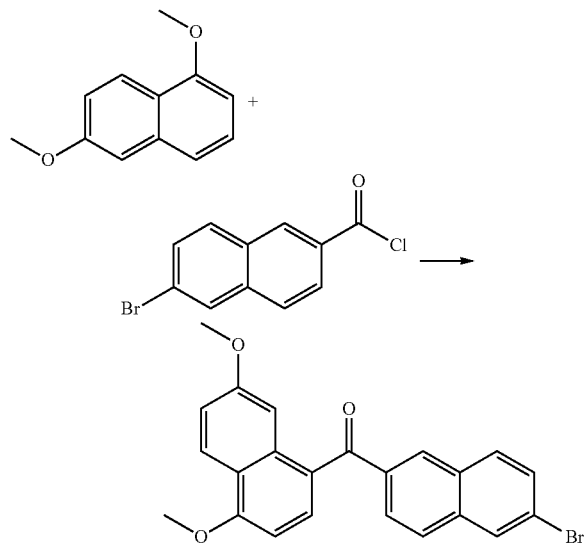

Synthesis Example 33

Synthesis of 4-[(6-bromonaphthalen-2-yl)dimethoxymethyl]-1,6-dimethoxynaphthalene 4-[(6-Bromonaphthalen-2-yl)dimethoxymethyl]-1,6-dimethoxynaphthalene (5.1 g) is obtained in the same procedure as Synthesis Example 21 except that (6-bromonaphthalen-2-yl)-(4,7-dimethoxynaphthalen-1-yl)methanone is used instead of 4-bromo-4'-phenylsulfanylbenzophenone.

[Chem. 70]

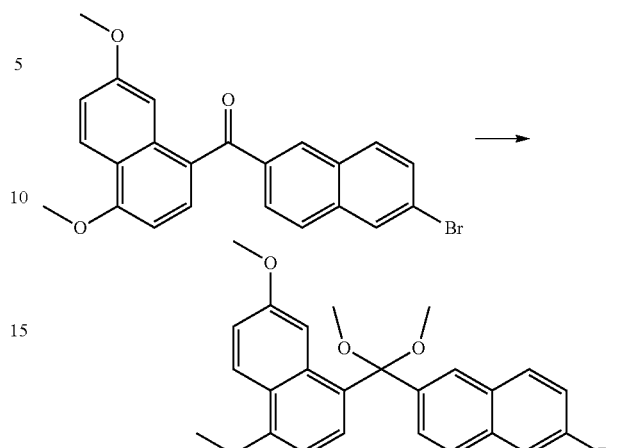

Synthesis Example 34

Synthesis of {6-[(4,7-dimethoxynaphthalen-1-yl)dimethoxymethyl]naphthalen-2-yl}diphenylsulfonium-nonafluorobutanesulfonate (Sulfonium Salt 12)

{6-[(4,7-Dimethoxynaphthalen-1-yl)dimethoxymethyl]naphthalen-2-yl}diphenylsulfonium-nonafluorobutanesulfonate (4.0 g) is obtained in the same procedure as Synthesis Example 22 except that 4-[(6-bromonaphthalen-2-yl)-dimethoxy-methyl]-1,6-dimethoxynaphthalene is used instead of 4-bromo-4'-phenylsulfanylbenzophenone dimethyl acetal. A molar absorption coefficient at 365 nm of the obtained compound is $1.0 \times 10^5$ cm$^2$/mol or smaller.

[Chem. 71]

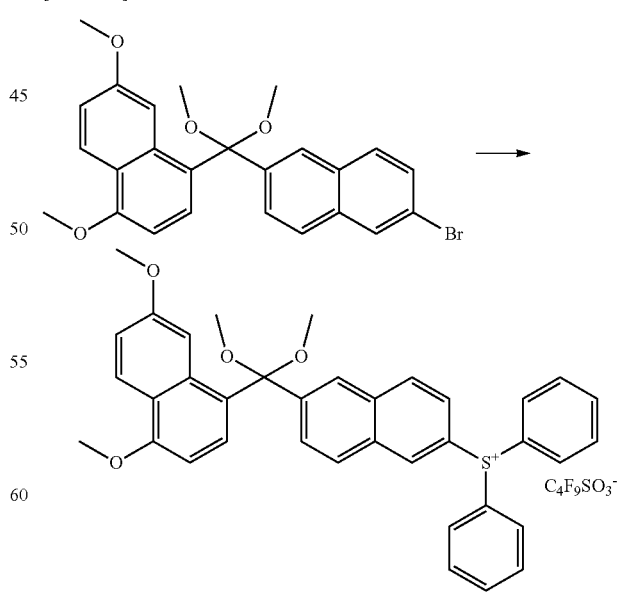

(Sulfonium Salt 12)

<Synthesis of Sulfonium Salt 13>

Synthesis Example 35

Synthesis of 4-(4-bromophenylsulfanyl)benzophenone 4-(4-Bromophenylsulfanyl)benzophenone (5.8 g) is obtained in the same procedure as Synthesis Example 2 except that 4-fluorobenzophenone is used instead of 4-fluoro-4'-methylsulfanylbenzophenone and 4-bromothiophenol is used instead of thiophenol.

[Chem. 72]

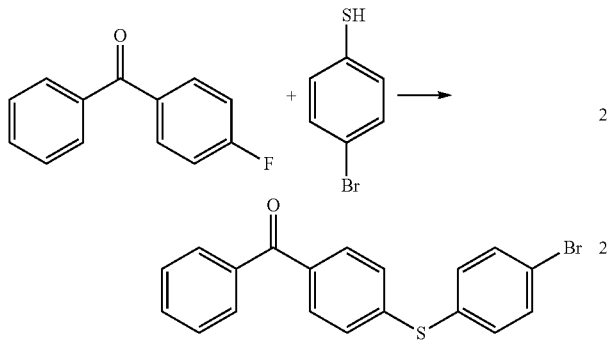

Synthesis Example 36

Synthesis of 4-(4-bromophenylsulfanyl)benzophenone dimethyl acetal 4-(4-Bromophenylsulfanyl)benzophenone dimethyl acetal (5.1 g) is obtained in the same procedure as Synthesis Example 21 except that
4-(4-bromophenylsulfanyl)benzophenone is used instead of 4-bromo-4'-phenylsulfanylbenzophenone.

[Chem. 73]

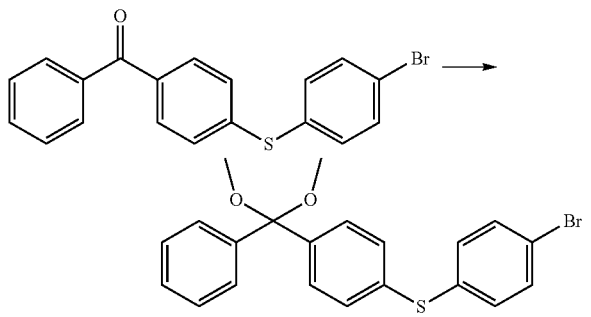

Synthesis Example 37

Synthesis of {4-[4-(dimethoxy-phenyl-methyl)phenylsulfanyl]phenyl}diphenylsulfonium-nonafluorobutanesulfonate (Sulfonium Salt 13)

{4-[4-(Dimethoxy-phenyl-methyl)phenylsulfanyl]phenyl}diphenylsulfonium-nonafluorobutanesulfonate (4.0 g) is obtained in the same procedure as Synthesis Example 22 except that 4-(4-bromophenylsulfanyl)benzophenone dimethyl acetal is used instead of 4-bromo-4'-phenylsulfanylbenzophenone dimethyl acetal. A molar absorption coefficient at 365 nm of the obtained compound is $1.0 \times 10^5$ $cm^2/mol$ or smaller.

[Chem. 74]

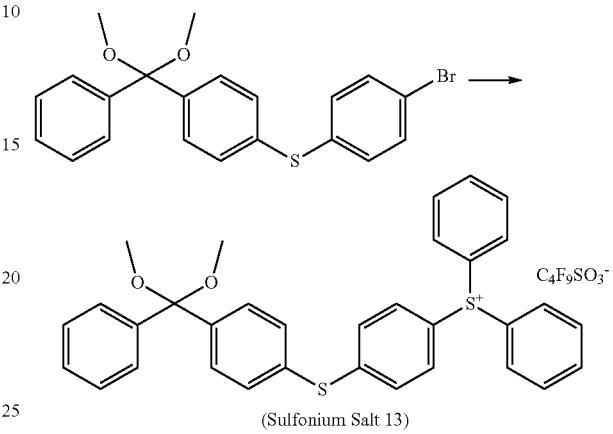

(Sulfonium Salt 13)

<Synthesis of Sulfonium Salt 14>

Synthesis Example 38

Synthesis of (4-fluorophenyl)-(6-methoxynaphthalen-2-yl)methanone (4-Fluorophenyl)-(6-methoxynaphthalen-2-yl)methanone (4.3 g) is obtained in the same procedure as Synthesis Example 1 except that 2-bromo-6-methoxynaphthalene is used instead of 4-bromothioanisole.

[Chem. 75]

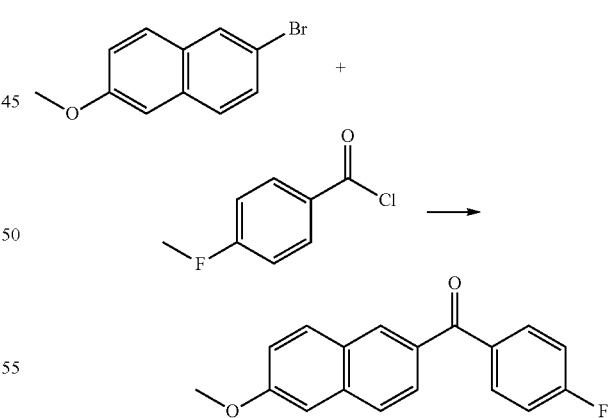

Synthesis Example 39

Synthesis of [4-(4-bromophenoxy)phenyl]-(6-methoxynaphthalen-2-yl)methanone

[4-(4-Bromophenoxy)phenyl]-(6-methoxynaphthalen-2-yl)methanone (5.9 g) is obtained in the same procedure as Synthesis Example 2 except that (4-fluorophenyl)-(6- methoxynaphthalen-2-yl)methanone is used instead of 4-fluoro-4'-methylsulfanylbenzophenone and 4-bromophenol is used instead of thiophenol.

[Chem. 76]

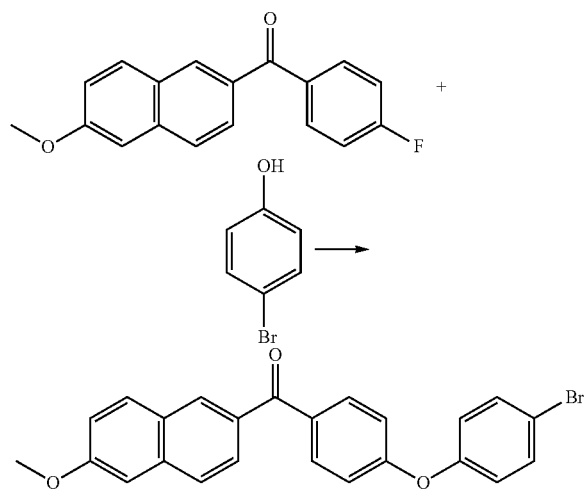

Synthesis Example 40

Synthesis of 2-{[4-(4-bromophenoxy)phenyl]-dimethoxymethyl}-6-methoxynaphthalene 2-{[4-(4-Bromophenoxy)phenyl]-dimethoxymethyl}-6-methoxynaphthalene (5.0 g) is obtained in the same procedure as Synthesis Example 20 except that [4-(4-bromophenoxy)phenyl]-(6-methoxynaphthalen-2-yl)methanone is used instead of 4-bromo-4'-phenylsulfanylbenophenone.

[Chem. 77]

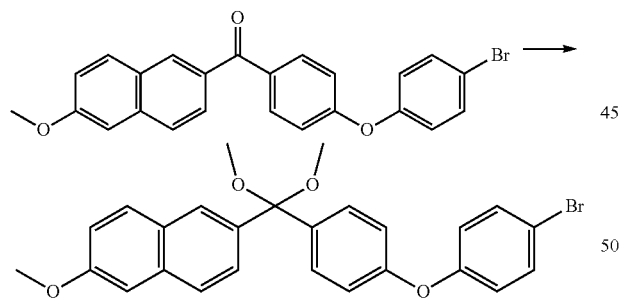

Synthesis Example 41

Synthesis of {4-{4-[dimethoxy-(6-methoxynaphthalen-2-yl)methyl]phenoxy}phenyl}diphenylsulfonium-nonafluorobutanesulfonate (Sulfonium Salt 14)

{4-{4-[Dimethoxy-(6-methoxynaphthalen-2-yl)methyl]phenoxy}phenyl}diphenylsulfonium-nonafluorobutanesulfonate (4.0 g) is obtained in the same procedure as Synthesis Example 22 except that 2-{[4-(4-bromophenoxy)phenyl]-dimethoxymethyl}-6-methoxynaphthalene is used instead of 4-bromo-4'-phenylsulfanylbenzophenone dimethyl acetal. A molar absorption coefficient at 365 nm of the obtained compound is $1.0 \times 10^5$ cm$^2$/mol or smaller.

[Chem. 78]

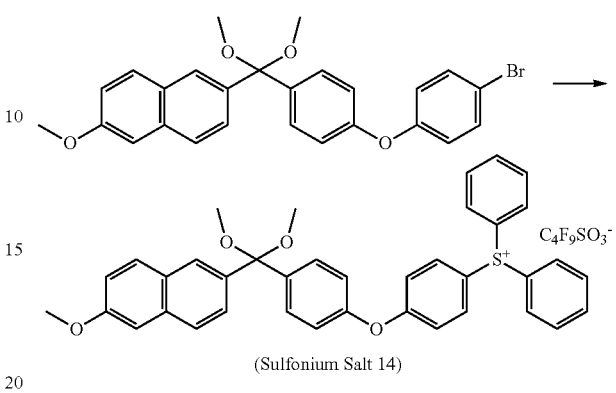

(Sulfonium Salt 14)

<Synthesis of Iodonium Salt 1>

Synthesis Example 42

Synthesis of 2,4-dimethoxy-4'-iodobenzophenone 2,4-Dimethoxy-4'-iodobenzophenone (5.3 g) is obtained in the same procedure as Synthesis Example 16 except that 4-iodobenzoyl chloride is used instead of 4-fluorobenzoyl chloride.

[Chem. 79]

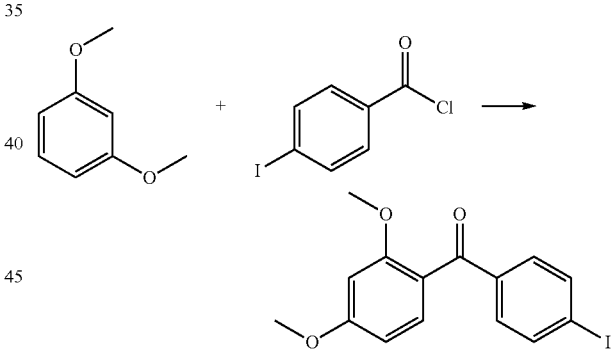

Synthesis Example 43

Synthesis of (4-t-butylphenyl)[4-(2,4-dimethoxybenzoyl)phenyl]iodonium-nonafluorobutanesulfonate 2,4-Dimethoxy-4'-iodobenzophenone (4 g) obtained in Synthesis Example 41 is added to sulfuric acid (16 g), then potassium persulfate (10 g) is added thereto in small portions at 10° C. or lower, and a mixture is stirred for 30 minutes. After stirring, t-butylbenzene (18 g) is added thereto, and a mixture is further stirred at 25° C. for 3 hours. After stirring, pure water (30 g) is added thereto at 10° C. or lower, then methylene chloride (40 g) and potassium nonafluorobutanesulfonate (3.7 g) is added thereto, and a mixture is stirred at 25° C. for about 2 hours. A stirred mixture is phase-separated, washed three times with water, and then methylene chloride is evaporated to obtain a crude product. The crude product is purified by silica gel column chromatography (methylene chloride/methanol=90/10 (volume ratio)) to obtain (4-t-butylphenyl)[4-(2,4-dimethoxybenzoyl)phenyl]iodonium-nonafluorobutanesulfonate (3.5 g). A molar absorption coefficient at 365 nm of the obtained compound is $1.0 \times 10^6$ $cm^2/mol$ or greater.

[Chem. 80]

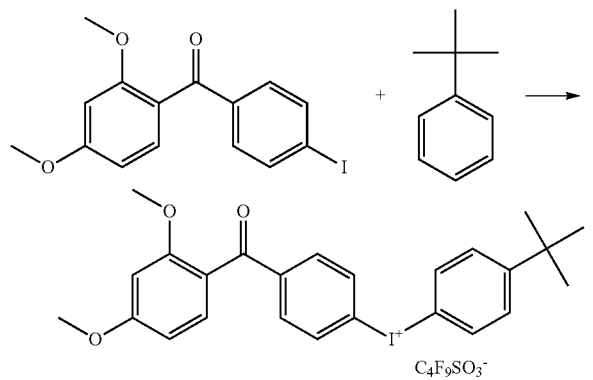

Synthesis Example 44

Synthesis of (4-t-butylphenyl){4-[(2,4-dimethoxyphenyl)dimethoxymethyl]phenyl}iodonium-nonafluorobutanesulfonate (Iodonium Salt 1)

(4-t-Butylphenyl)[4-[(2,4-dimethoxyphenyl)dimethoxymethyl]phenyl]iodonium-nonafluorobutanesulfonate (1.0 g) is obtained in the same procedure as Synthesis Example 4 except that (4-t-butylphenyl)[4-(2,4-dimethoxybenzoyl)phenyl]iodonium-nonafluorobutanesulfonate is used instead of dimethyl-[4-(4-phenylsulfanyl-benzoyl)phenyl]sulfonium-nonafluorobutanesulfonate. A molar absorption coefficient at 365 nm of the obtained compound is $1.0 \times 10^5$ $cm^2/mol$ or smaller, which is one-tenth or smaller in comparison with that of (4-t-butylphenyl)[4-(2,4-dimethoxybenzoyl)phenyl]iodonium-nonafluorobutanesulfonate obtained in Synthesis Example 43.

[Chem. 81]

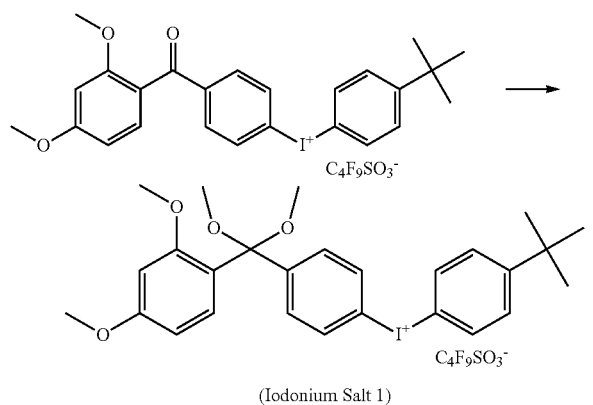

(Iodonium Salt 1)

<Synthesis of Iodonium Salt 2>

Synthesis Example 45

Synthesis of (4, 7-dimethoxynaphthalen-1-yl)-(4-iodophenyl)methanone (4,7-Dimethoxynaphthalen-1-yl)-(4-iodophenyl)methanone (5.4 g) is obtained in the same procedure as Synthesis Example 19 except that 1,6-dimethoxynaphthalene is used instead of diphenyl sulfide and 4-iodobenzoyl chloride is used instead of 4-bromobenzoyl chloride.

[Chem. 82]

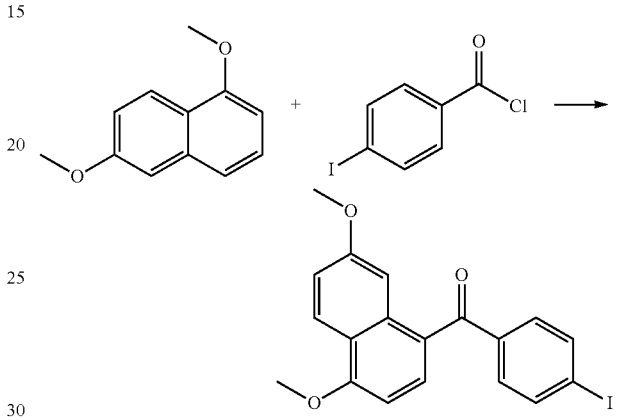

Synthesis Example 46

Synthesis of [4-(4,7-dimethoxynaphthalen-1-ylcarbonyl)phenyl]phenyliodonium-nonafluorobutanesulfonate

[4-(4,7-Dimethoxynaphthalen-1-ylcarbonyl)phenyl]phenyliodonium-nonafluorobutanesulfonate (3.3 g) is obtained in the same procedure as Synthesis Example 42 except that (4,7-dimethoxynaphthalen-1-yl)-(4-iodophenyl)methanone is used instead of 2,4-dimethoxy-4'-iodobenzophenone. A molar absorption coefficient at 365 nm of the obtained compound is $1.0 \times 10^6$ $cm^2/mol$ or greater.

[Chem. 83]

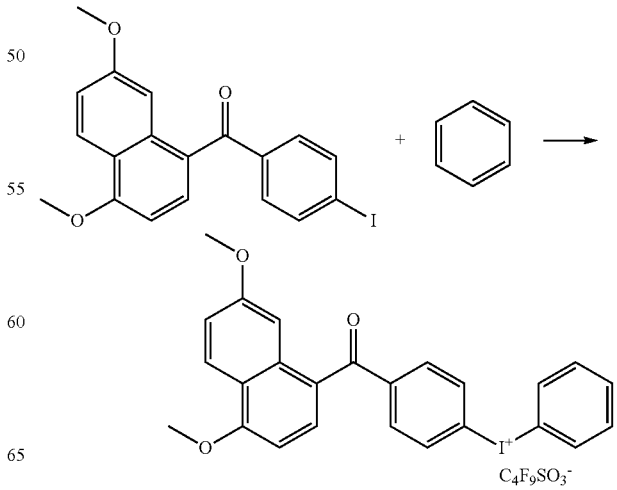

Synthesis Example 47

Synthesis of {4-[(4,7-dimethoxynaphthalen-1-yl)dimethoxymethyl]phenyl}phenyliodonium-nonafluorobutanesulfonate (Iodonium Salt 2)

{4-[(4,7-Dimethoxynaphthalen-1-yl)-dimethoxy-methyl]phenyl}phenyliodonium-nonafluorobutanesulfonate (1.0 g) is obtained in the same procedure as Synthesis Example 4 except that {4-(4,7-dimethoxynaphthalene-1-carbonyl)phenyl}phenyliodonium-nonafluorobutanesulfonate is used instead of dimethyl-[4-(4-phenylsulfanylbenzoyl)phenyl]sulfonium-nonafluorobutanesulfonate. A molar absorption coefficient at 365 nm of the obtained compound is $1.0 \times 10^5$ cm$^2$/mol or smaller, which is one-tenth or smaller in comparison with that of {4-(4,7-dimethoxynaphthalen-1-ylcarbonyl)phenyl}phenyliodonium-nonafluorobutanesulfonate obtained in Synthesis Example 46.

[Chem. 84]

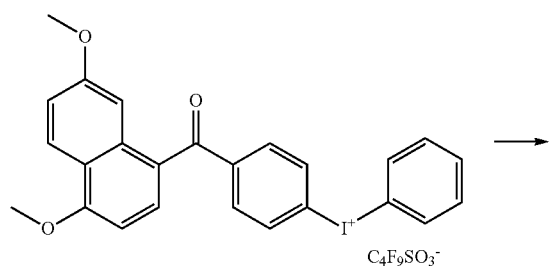

(Iodonium Salt 2)

<Synthesis of Sulfonium Salt 15>

Synthesis Example 48

Synthesis of {4-[dimethoxy-(4-phenylsulfanylphenyl)methyl]phenyl}diphenylsulfonium-p-styrenesulfonate (Sulfonium Salt 15)

{4-[Dimethoxy-(4-phenylsulfanylphenyl)methyl]phenyl}diphenylsulfonium-p-styrenesulfonate (2.8 g) is obtained in the same procedure as Synthesis Example 22 except that sodium p-styrenesulfonate hydrate is used instead of potassium nonafluorobutanesulfonate. A molar absorption coefficient at 365 nm of the obtained compound is $1.0 \times 10^5$ cm$^2$/mol or smaller.

[Chem. 85]

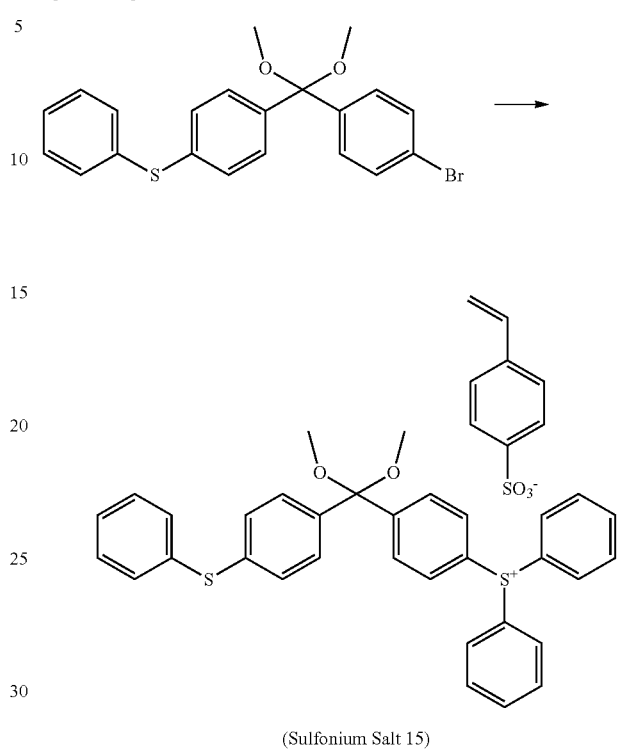

(Sulfonium Salt 15)

<Synthesis of Sulfonium Salt 16>

Synthesis Example 49

Synthesis of {4-[dimethoxy-(4-phenylsulfanylphenyl) methyl]phenyl}diphenylsulfonium-(4-methacryloyl-1,1,2-trifluorobutanesulfonate) (Sulfonium Salt 16)

{4-[Dimethoxy-(4-phenylsulfanylphenyl)methyl]phenyl}diphenylsulfonium-(4-methacryloyl-1,1,2-trifluorobutanesulfonate) (3.0 g) is obtained in the same procedure as Synthesis Example 22 except that sodium 4-methacryloyloxy-1,1,2-trifluorobutanesulfonate is used instead of potassium nonafluorobutanesulfonate. A molar absorption coefficient at 365 nm of the obtained compound is $1.0 \times 10^5$ cm$^2$/mol or smaller.

[Chem. 86]

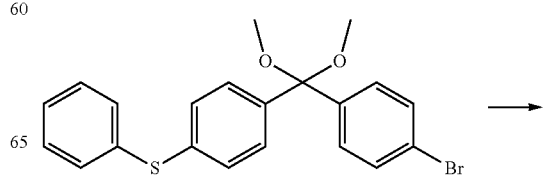

-continued

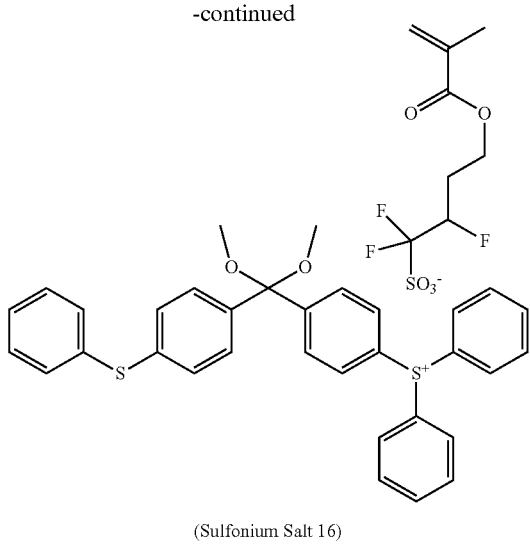

(Sulfonium Salt 16)

<Synthesis of Sulfonium Salt 17>

Synthesis Example 50

Synthesis of 4-bromo-4'-phenylsulfinylbenzophenone

Formic acid (53.3 g) is added to 4-bromo-4'-phenylsulfanylbenzophenone (10.1 g) obtained in Synthesis Example 20, a mixture is stirred at 50° C., then 35% by mass of aqueous solution (2.9 g) of hydrogen peroxide is added dropwise thereto in small portions, and a mixture is stirred at 50° C. After 1 hour, a reaction solution is cooled with ice cooling, and pure water (28.2 g) and toluene (80.3 g) are added thereto. A mixture is phase-separated, an organic layer is washed three times with pure water (30 g), and then an organic solvent is evaporated to obtain 4-bromo-4'-phenylsulfinylbenzophenone (10.0 g).

[Chem. 87]

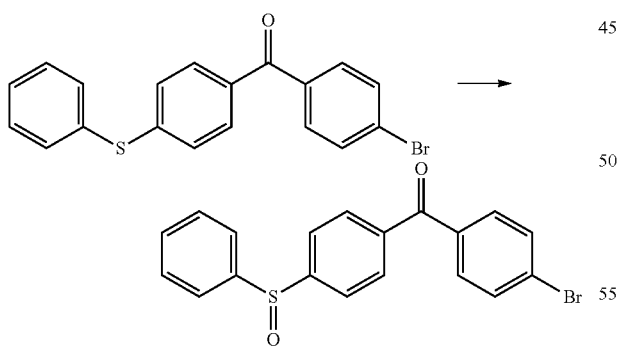

Synthesis Example 51

Synthesis of 4-(4-hydroxyphenylsulfanyl)-4'-phenylsulfinylbenzophenone

4-Bromo-4'-phenylsulfinylbenzophenone (7.7 g), potassium carbonate (3.6 g) and 4-hydroxybenzenethiol (3.0 g) are dissolved in DMF (23.1 g), and a mixture is stirred at 60° C. After 2 hours, a reaction solution is cooled with ice cooling, and pure water (70 g) is added dropwise thereto to precipitate a solid. The precipitated solid is filtered, and re-dissolved in methylene chloride (40 g). A solution is washed three times with pure water (40 g), and then methylene chloride is evaporated to obtain a crude crystal. The crude crystal is purified by silica gel column chromatography (hexane/ethyl acetate=2/1 (volume ratio)) to obtain 4-(4-hydroxyphenylsulfanyl)-4'-phenylsulfinylbenzophenone (6.4 g).

[Chem. 88]

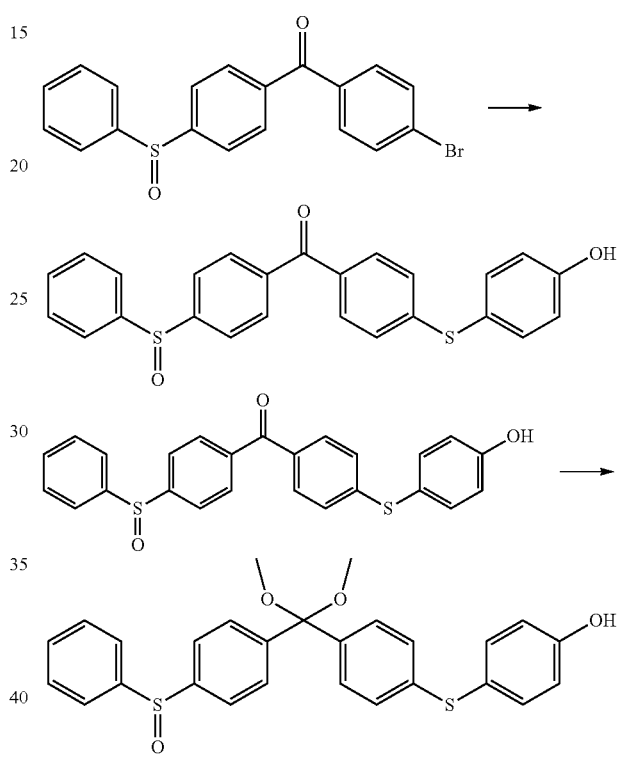

Synthesis Example 52

Synthesis of 4-(4-hydroxyphenylsulfanyl)-4'-phenylsulfinylbenzophenone dimethyl acetal 4-(4-Hydroxyphenylsulfanyl) -4'-phenylsulfinylbenzophenone dimethyl acetal (5.0 g) is obtained in the same procedure as Synthesis Example 21 except that 4-(4-hydroxyphenylsulfanyl)-4'-phenylsulfinylbenzophenone is used instead of 4-bromo-4'-phenylsulfanylbenzophenone.

[Chem. 89]

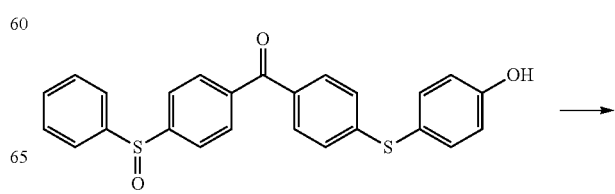

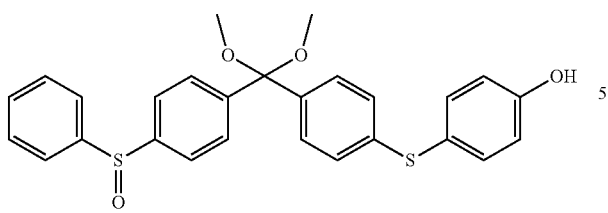

Synthesis Example 53

Synthesis of (4-{dimethoxy-[4-(4-hydroxyphenylsulfanyl)phenyl]methyl}phenyl)diphenylsulfonium-nonafluorobutanesulfonate (Sulfonium Salt 17)

4-(4-Hydroxyphenylsulfanyl)-4'-phenylsulfinylbenzophenone dimethyl acetal (5.0 g) is dissolved in dehydrated methylene chloride (30.0 g), and a 2 M THF solution (6.8 mL) of phenylmagnesium chloride is added dropwise thereto with ice cooling. Then, trichlorosilane (1.7 g) is added dropwise thereto, and a mixture is stirred for 1 hour. After stirring, 10% by mass of aqueous solution (30 g) of ammonium chloride is added thereto at 5° C. or lower, a mixture is further stirred, and washed twice with isopropyl ether (5.0 g). Then, methylene chloride (40 g) and potassium nonafluorobutanesulfonate (3.4 g) are added thereto, and a mixture is stirred at 25° C. for 2 hours. A stirred mixture is phase-separated, washed three times with pure water (20 g), and then methylene chloride is evaporated to obtain a crude crystal. The crude crystal is purified by silica gel column chromatography (methylene chloride/methanol=90/10 (volume ratio)) to obtain (4-{dimethoxy-[4-(4-hydroxyphenylsulfanyl)phenyl]methyl}phenyl) diphenylsulfonium-nonafluorobutanesulfonate (3.4 g).

[Chem. 90]

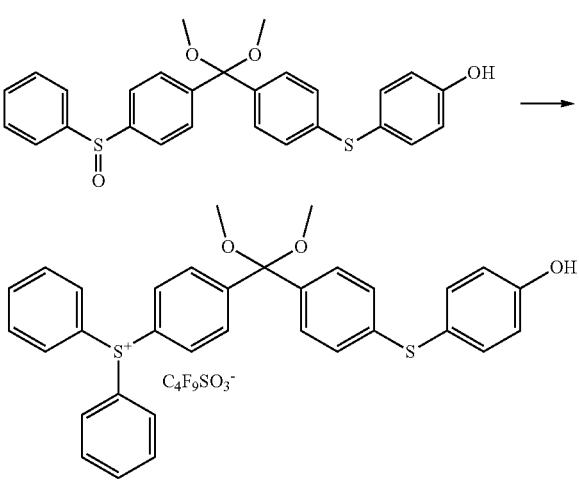

(Sulfonium Salt 17)

<Synthesis of Sulfonium Salt 18>

Synthesis Example 54

Synthesis of (2-hydroxy-9-oxo-9H-fluoren-3-yl)diphenylsulfonium-nonafluorobutanesulfonate 2-Hydroxy-9-fluorenone (1.0 g), diphenyl sulfoxide (1.0 g) and diphosphorus pentaoxide (0.4 g) are added to methanesulfonic acid (6.0 g), and a mixture is stirred with ice cooling. After 18 hours, pure water (20 g) is added dropwise to a reaction solution, and a mixture is washed twice with isopropyl ether (5.0 g). Then, methylene chloride (20 g) and potassium nonafluorobutanesulfonate (1.7 g) are added thereto, and a mixture is stirred at 25° C. for 2 hours. A stirred mixture is phase-separated, wash three times with pure water (10 g), and then methylene chloride is evaporated to obtain a crude crystal. The crude crystal is purified by silica gel column chromatography (methylene chloride/methanol=90/10 (volume ratio)) to obtain (2-hydroxy-9-oxo-9H-fluoren-3-yl)diphenylsulfonium-nonafluorobutanesulfonate (2.1 g).

[Chem. 91]

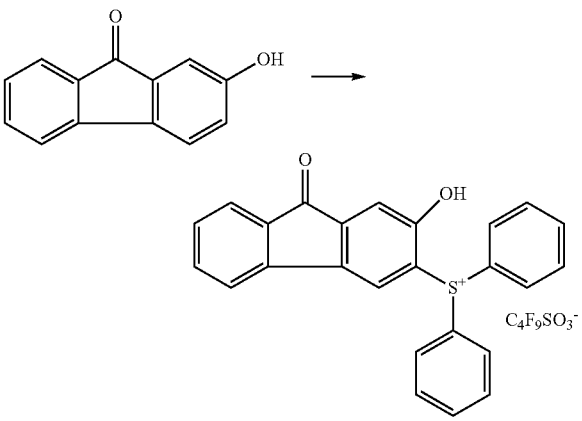

Synthesis Example 55

Synthesis of (2-hydroxy-9,9-dimethoxy-9H-fluoren-3-yl)diphenylsulfonium-nonafluorobutanesulfonate (2-Hydroxy-9,9-dimethoxy-9H-fluoren-3-yl)diphenylsulfonium-nonafluorobutanesulfonate (2.1 g) is obtained in the same procedure as Synthesis Example 21 except that (2-hydroxy-9-oxo-9H-fluoren-3-yl)diphenylsulfonium-nonafluorobutanesulfonate is used instead of 4-bromo-4'-phenylsulfanylbenzophenone.

[Chem. 92]

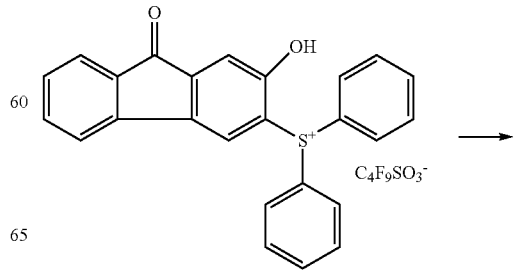

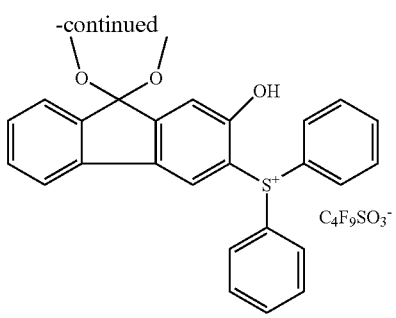

Synthesis Example 56

Synthesis of [spiro(1,3-dioxolane-2,9'-[9H]fluorene), 2'-hydrox-3'-yl]diphenylsulfonium-nonafluorobutanesulfonate (Sulfonium Salt 18)

(2-Hydroxy-9,9-dimethoxy-9H-fluoren-3-yl) diphenylsulfonium-nonafluorobutanesulfonate (2.0 g) and ethylene glycol (0.7 g) are dissolved in dehydrated THF (16.0 g). Then, p-toluenesulfonic acid (48.0 mg) is added thereto, and a mixture is stirred at room temperature under nitrogen atmosphere. After 18 hours, triethylamine (0.2 g) was added to the reaction solution. THF is evaporated, then methylene chloride (20 g) and pure water (20 g) are added thereto. A mixture is phase-separated, washed twice with pure water (20 g), and then methylene chloride is evaporated to obtain {spiro(1,3-dioxolane-2,9'-[9H]fluorene),2'-hydrox-3'-yl}diphenylsulfonium-nonafluorobutanesulfonate (1.8 g).

[Chem. 93]

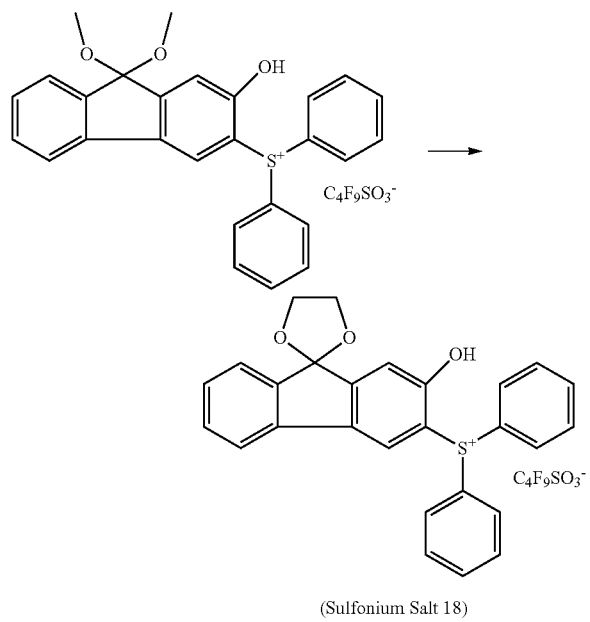

(Sulfonium Salt 18)

<Synthesis of Sulfonium Salt 19>

Synthesis Example 57

Synthesis of 1-(6-methoxy-2-naphthalenyl)-3-(4-methylphenyl)-2-propen-1-one.

2-Acetyl-6-methoxynaphthalene (1.6 g) and 4-methylbenzaldehyde (1.1 g) are dissolved in ethanol (16 g), and a mixture is stirred. 10% by mass of aqueous solution (0.4 g) of sodium hydroxide is added dropwise thereto with ice cooling, and a mixture is further stirred. After 3 hours, a precipitated solid in a reaction solution is filtered, and washed with ethanol (8 g). A recovered solid is dried to obtain 1-(6-methoxy-2-naphthalenyl)-3-(4-methylphenyl)-2-propen-1-one (2.2 g).

[Chem. 94]

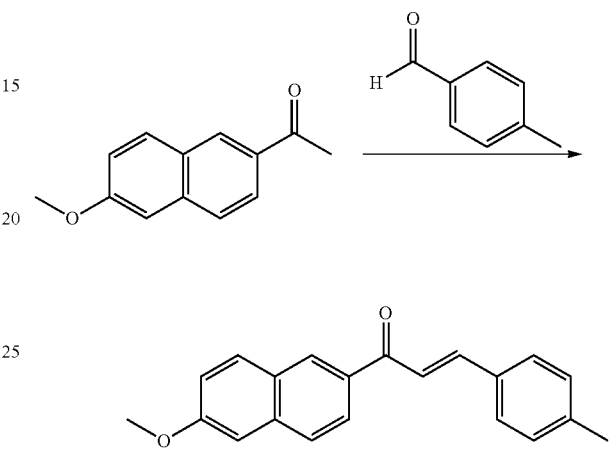

Synthesis Example 58

Synthesis of {6-[3-(4-methylphenyl)-1-oxo-2-propenyl]-2-methoxynaphthalen-1-yl}diphenylsulfonium-nonafluorobutanesulfonate 1-(6-Methoxy-2-naphthalenyl)-3-(4-methylphenyl)-2-propen-1-one (0.8 g) and diphosphorus pentaoxide (0.3 g) are added to methanesulfonic acid (2.4 g), and a mixture is stirred. Diphenyl sulfoxide (0.4 g) is added thereto in small portions with ice cooling, and a mixture is further stirred. After 3 hours, pure water (20 g) is added dropwise thereto with ice cooling, a mixture is further stirred, and washed twice with isopropyl ether (5.0 g). Then, methylene chloride (20 g) and potassium nonafluorobutanesulfonate (0.7 g) are added thereto, and a mixture is stirred for 2 hours. A stirred mixture is phase-separated, washed three times with pure water (10 g), and then methylene chloride is evaporated to obtain a crude crystal. The crude crystal is purified by silica gel column chromatography (methylene chloride/methanol=90/10 (volume ratio)) to obtain {6-[3-(4-methylphenyl)-1-oxo-2-propenyl]-2-methoxynaphthalen-1-yl}diphenylsulfonium-nonafluorobutanesulfonate (0.9 g).

[Chem. 95]

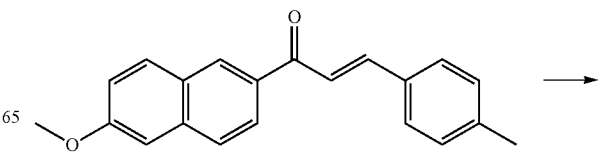

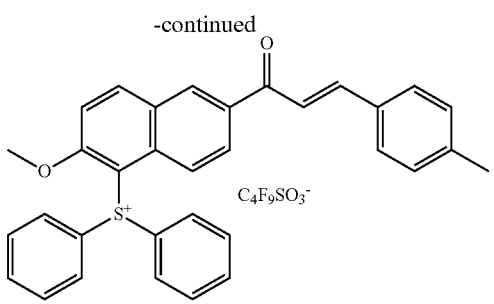

Synthesis Example 59

Synthesis of {6-[3-(4-methylphenyl)-1,1-dimethoxy-2-propenyl]-2-methoxynaphthalen-1-yl}diphenylsulfonium-nonafluorobutanesulfonate (Sulfonium Salt 19)

{6-[3-(4-Methylphenyl)-1,1-dimethoxy-2-propenyl]-2-methoxynaphthalen-1-yl}diphenylsulfonium-nonafluorobutanesulfonate (0.9 g) is obtained in the same procedure as Synthesis Example 4 except that {6-[3-(4-methylphenyl)-1-oxo-2-propenyl]-2-methoxynaphthalen-1-yl}diphenylsulfonium-nonafluorobutanesulfonate is used instead of dimethyl-[4-(4-phenylsulfanyl)benzoylphenyl]sulfonium-nonafluorobutanesulfonate.

[Chem. 96]

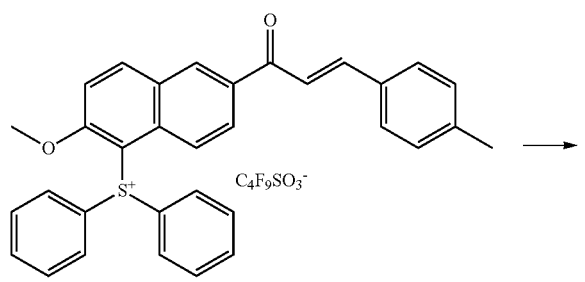

(Sulfonium Salt 19)

<Synthesis of Sulfonium Salt 20>

Synthesis Example 60

Synthesis of 2,3-dibromo-1-(6-methoxy-2-naphthalenyl)-3-(4-methylphenyl)-1-propanone 1-(6-Methoxy-2-naphthalenyl)-3-(4-methylphenyl)-2-propen-1-one (1.2 g) obtained in Synthesis Example 57 is dissolved in methylene chloride (9.6 g). Bromine (1.0 g) is dissolved in methylene chloride (2.0 g) to add dropwise thereto with ice cooling, and a mixture is stirred. After 2 hours, pure water (5 g) is added to a reaction solution, and a mixture is further stirred. A stirred mixture is phase-separated, an organic layer is washed twice with pure water (5 g), and then an organic solvent is evaporated to obtain 2,3-dibromo-1-(6-methoxy-2-naphthalenyl)-3-(4-methylphenyl)-1-propanone (1.8 g).

[Chem. 97]

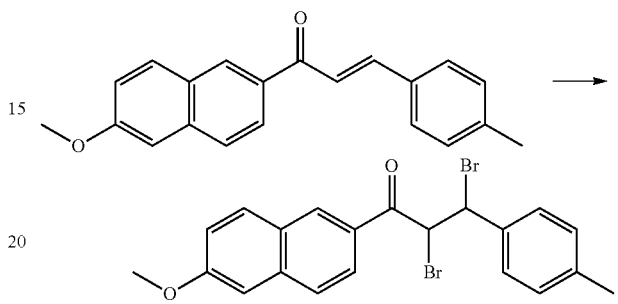

Synthesis Example 61

Synthesis of 1-(6-methoxy-2-naphthalenyl)-3-(4-methylphenyl)-2-propyn-1-one 2,3-Dibromo-1-(6-methoxy-2-naphthalenyl)-3-(4-methylphenyl)-1-propanone (1.8 g) and diazabicycloundecene (0.8 g) is added to acetonitrile (14 g), and a mixture is stirred at room temperature. After 2 hours, potassium t-butoxide (1.6 g) is added thereto, and a mixture is further stirred. After 2 hours, pure water (36 g) is added to a reaction solution to precipitate a solid. The precipitated solid is filtered, washed with pure water (20 g), and then dried to obtain 1-(6-methoxy-2-naphthalenyl)-3-(4-methylphenyl)-2-propyn-1-one (1.0 g).

[Chem. 98]

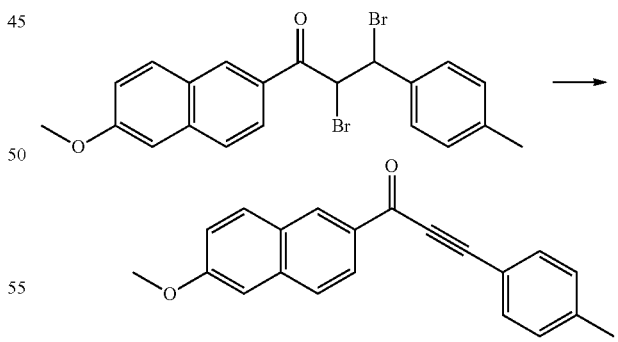

Synthesis Example 62

Synthesis of {6-[3-(4-methylphenyl)-1-oxo-2-propynyl]-2-methoxynaphthalen-1-yl}diphenylsulfonium-nonafluorobutanesulfonate {6-[3-(4-Methylphenyl)-1-oxo-2-propynyl]-2-methoxynaphthalen-1-yl}diphenylsulfonium-nonafluorobutanesulfonate (0.8 g) is obtained in the same procedure as Synthesis Example 58 except that 1-(6-methoxy-2-naphthalenyl)-3-(4-methylphenyl)-2-propyn-1-one is used instead of 1-(6-methoxy-2-naphthalenyl)-3-(4-methylphenyl)-2-propen-1-one.

[Chem. 99]

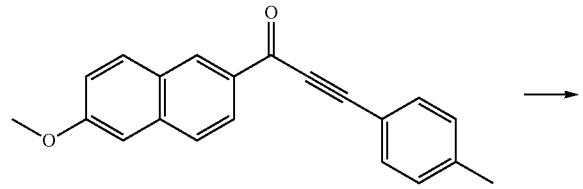

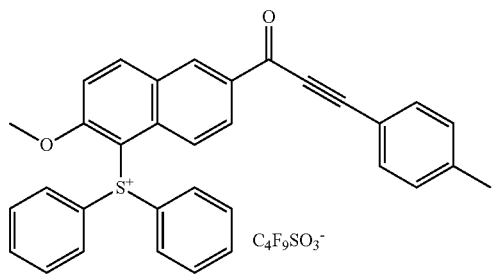

Synthesis Example 63

Synthesis of {6-[3-(4-methylphenyl)-1,1-dimethoxy-2-propynyl]-2-methoxynaphthalen-1-yl}diphenylsulfonium-nonafluorobutanesulfonate (Sulfonium Salt 20)

{6-[3-(4-Methylphenyl)-1,1-dimethoxy-2-propynyl]-2-methoxynaphthalen-1-yl}diphenylsulfonium-nonafluorobutanesulfonate (0.8 g) is obtained in the same procedure as Synthesis Example 4 except that {6-[3-(4-methylphenyl)-1-oxo-2-propynyl]-2-methoxynaphthalen-1-yl}diphenylsulfonium-nonafluorobutanesulfonate is used instead of dimethyl-[4-(4-phenylsulfanyl)benzoylphenyl]sulfonium-nonafluorobutanesulfonate.

[Chem. 100]

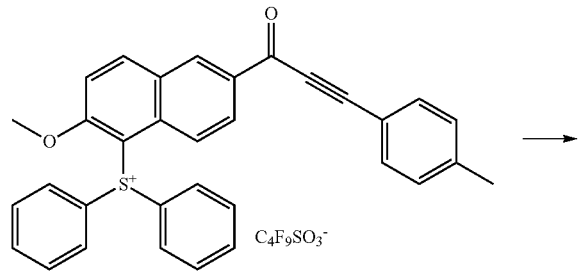

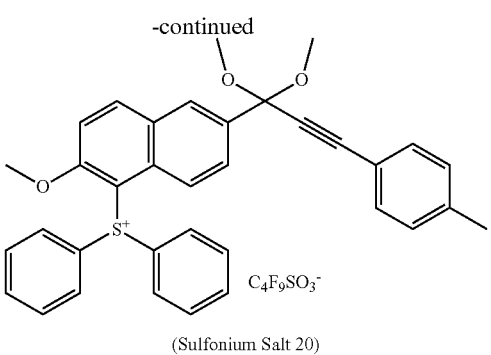

(Sulfonium Salt 20)

<Synthesis of Sulfonium Salt 21>

Synthesis Example 64

Synthesis of 4-phenylsulfanylbenzil

4-Phenylsulfanylbenzil (0.8 g) is obtained in the same procedure as Synthesis Example 2 except that 4-chlorobenzil (1 g) is used instead of 4-fluoro-4'-methylsulfanylbenzophenone.

[Chem. 101]

Synthesis Example 65

Synthesis of [4-(benzoylcarbonyl)phenyl]dimethylsulfonium-nonafluorobutanesulfonate 4-Phenylsulfanylbenzil (0.8 g), diphenyliodonium-nonafluorobutanesulfonate (1.6 g) and copper (II) acetate dihydrate (55 mg) are added to chlorobenzene (8.0 g), and a mixture is stirred at 80° C. After 2 hours, a reaction solution is cooled to 25° C., and pure water (5.0 g) is added thereto. A mixture is phase-separated, an organic layer is washed twice with pure water (5.0 g), and then an organic solvent is evaporated to obtain a crude crystal. The crude crystal is purified by silica gel column chromatography (methylene chloride/methanol=90/10 (volume ratio)) to obtain [4-(benzoylcarbonyl)phenyl]dimethylsulfonium-nonafluorobutanesulfonate (1.0 g).

[Chem. 102]

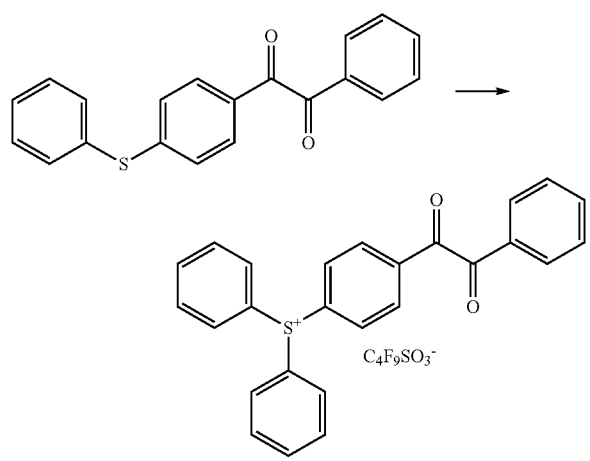

Synthesis Example 66

Synthesis of [4-(benzoyldimethoxymethyl)phenyl]dimethylsulfonium-nonafluorobutanesulfonate (Sulfonium Salt 21)

[4-(Benzoyldimethoxymethyl)phenyl]dimethylsulfonium-nonafluorobutanesulfonate (0.9 g) is obtained in the same procedure as Synthesis Example 4 except that [4-(benzoylcarbonyl)phenyl]dimethylsulfonium-nonafluorobutanesulfonate is used instead of dimethyl-[4-(4-phenylsulfanyl) benzoylphenyl]sulfonium-nonafluorobutanesulfonate.

[Chem. 103]

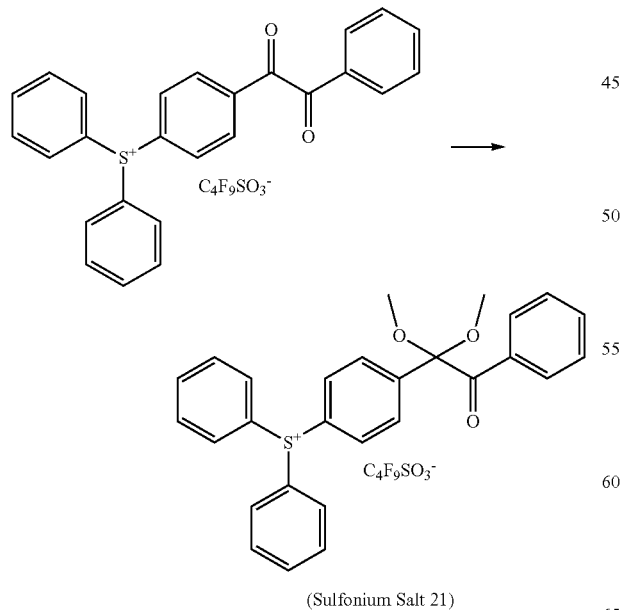

(Sulfonium Salt 21)

\<Synthesis of Sulfonium Salt 22\>

Synthesis Example 67

Synthesis of 4-bromo-4'-(4-methoxyphenyl)benzophenone

4-Bromo-4'-(4-methoxyphenyl)benzophenone (3.1 g) is obtained in the same procedure as Synthesis Example 16 except that 4-bromobenzoyl chloride is used instead of 4-fluorobenzoyl chloride, 4-phenylanisole is used instead of 2,4-dimethoxybenzene, and as purification method, silica gel column chromatography (hexane/ethyl acetate=80/20 (volume ratio)) is performed instead of recrystallization with ethanol.

[Chem. 104]

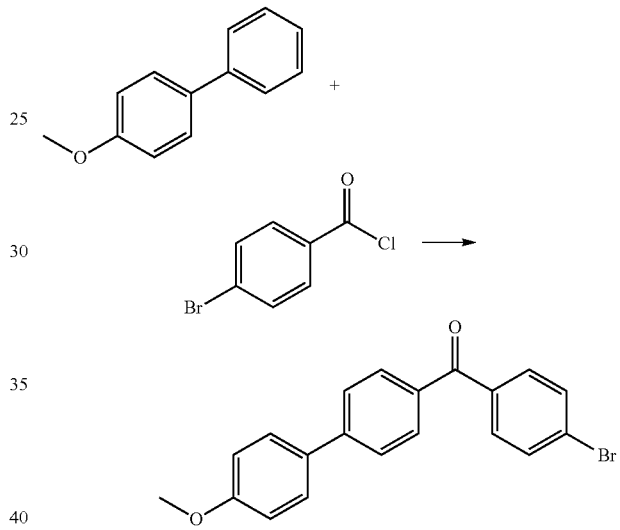

Synthesis Example 68

Synthesis of 4-bromo-4'-(4-methoxyphenyl)benzophenone dimethyl acetal

4-Bromo-4'-(4-methoxyphenyl)benzophenone (3.0 g) is obtained in the same procedure as Synthesis Example 21 except that 4-bromo-4'-(4-methoxyphenyl)benzophenone is used instead of 4-bromo-4'-phenylsulfanylbenophenone.

[Chem. 105]

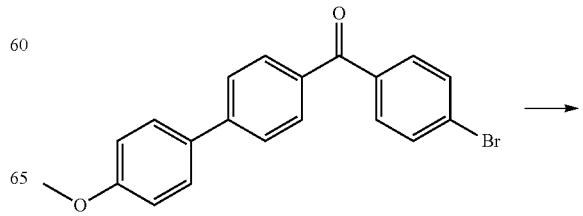

-continued

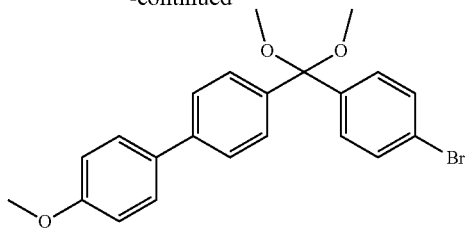

Synthesis Example 69

Synthesis of [4-(4'-methoxybiphenyl-4-carbonyl)phenyl]-diphenylsulfonium-nonafluorobutanesulfonate

[4-(4'-Methoxybiphenyl-4-carbonyl)phenyl]-diphenylsulfonium-nonafluorobutanesulfonate (4.7 g) is obtained in the same procedure as Synthesis Example 22 except that 4-bromo-4'-(4-methoxyphenyl)benzophenone dimethyl acetal is used instead of 4-bromo-4'-phenylsulfanylbenzophenone dimethyl acetal and 10% by mass of aqueous solution of hydrochloric acid is used instead of 10% by mass of aqueous solution of ammonium chloride.

[Chem. 106]

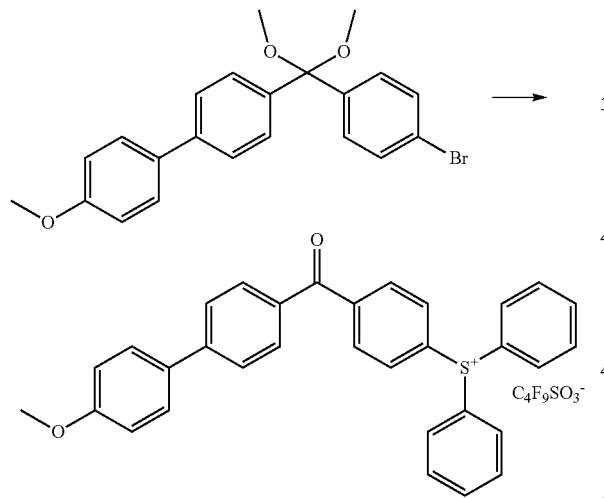

Synthesis Example 70

Synthesis of [4-(4'-hydroxybiphenyl-4-carbonyl)phenyl]-diphenylsulfonium-nonafluorobutanesulfonate

[4-(4'-Methoxybiphenyl-4-carbonyl)phenyl]-diphenylsulfonium-nonafluorobutanesulfonate (4.0 g) is added to acetic acid (40 ml). 48% by mass of aqueous solution (10.2 g) of HBr is added dropwise thereto at 70° C. After dropwise addition, a mixture is stirred at 110° C. for 20 hours. Then, water (150 g) is added thereto, methylene chloride (40 g) is added thereto, and a mixture is stirred. A stirred mixture is phase-separated, washed three times with water, and then methylene chloride is evaporated to obtain a crude crystal. The crude crystal is purified by silica gel column chromatography (methylene chloride/methanol=90/10 (volume ratio)) to obtain [4-(4'-hydroxybiphenyl-4-carbonyl)phenyl]-diphenylsulfonium-nonafluorobutanesulfonate (2.4 g).

[Chem. 107]

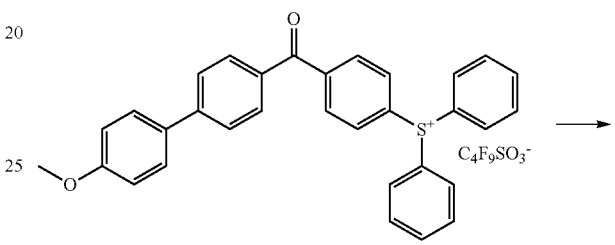

Synthesis Example 71

Synthesis of {4-[(4'-hydroxybiphenyl-4-yl)dimethoxymethyl]-phenyl}-diphenylsulfonium-nonafluorobutanesulfonate (Sulfonium Salt 22)

[4-(4'-Hydroxybiphenyl-4-carbonyl)phenyl]-diphenylsulfonium-nonafluorobutanesulfonate (1.0 g) obtained in Synthesis Example 70 is dissolved in methanol (2.5 g), trimethyl orthoformate (1.0 g) and concentrated sulfuric acid (4.0 mg) are added thereto, and a mixture is stirred at 60° C. for 2 hours. After stirring, triethylamine (0.5 g) is added thereto, a reaction solution is added to a mixed solution of methylene chloride (30 g) and pure water (10 g), a mixture is stirred for 10 minutes, and an organic layer is recovered. An obtained organic layer is washed three times with water, and then methylene chloride is evaporated to obtain {4-[(4'-hydroxybiphenyl-4-yl) dimethoxymethyl]-phenyl}-diphenylsulfonium-nonafluorobutanesulfonate (1.0 g).

[Chem. 108]

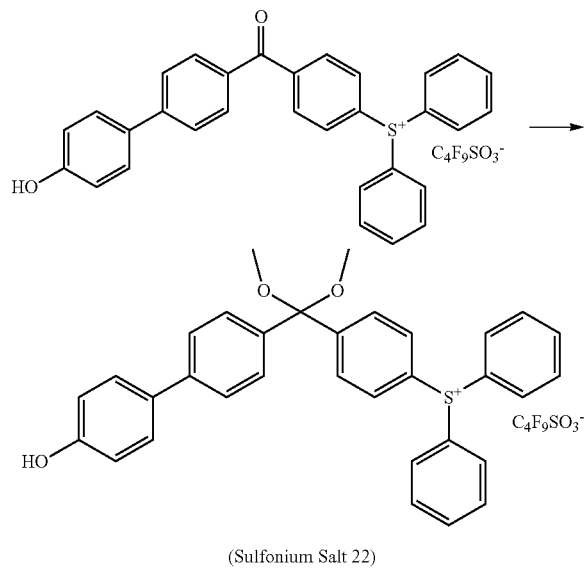

(Sulfonium Salt 22)

<Synthesis of Sulfonium Salt 23>

Synthesis Example 72

Synthesis of (6-bromo-naphthalen-2-yl)-(4-methoxyphenyl)methanone (6-Bromo-naphthalen-2-yl)-(4-methoxyphenyl)methanone (4.1 g) is obtained in the same procedure as Synthesis Example 16 except that 6-bromonaphthalenecarbonyl chloride is used instead of 4-fluorobenzoyl chloride and anisole is used instead of 2,4-dimethoxybenzene.

[Chem. 109]

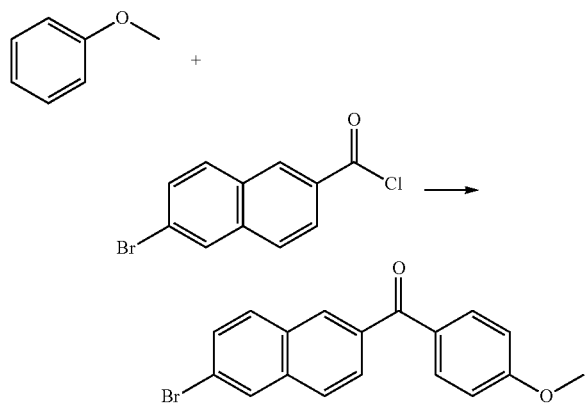

Synthesis Example 73

Synthesis of (6-bromo-naphthalen-2-yl)-(4-methoxyphenyl)methanone dimethyl acetal (6-Bromo-naphthalen-2-yl)-(4-methoxyphenyl)methanone dimethyl acetal (3.0 g) is obtained in the same procedure as Synthesis Example 21 except that (6-bromo-naphthalen-2-yl)-(4-methoxyphenyl)methanone is used instead of 4-bromo-4'-phenylsulfanylbenzophenone.

[Chem. 110]

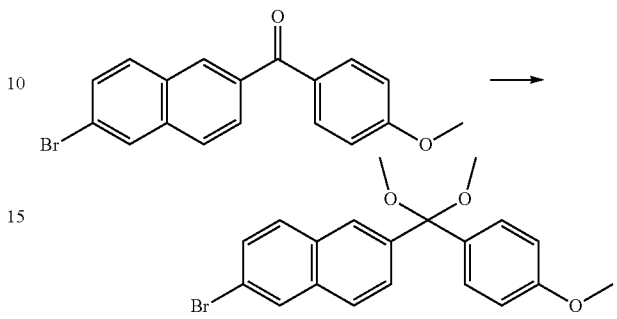

Synthesis Example 74

Synthesis of [6-(4-methoxybenzoyl)naphthalen-2-yl]diphenylsulfonium-nonafluorobutanesulfonate

[6-(4-Methoxybenzoyl)naphthalen-2-yl]diphenylsulfonium-nonafluorobutanesulfonate (4.5 g) is obtained in the same procedure as Synthesis Example 69 except that (6-bromo-naphthalen-2-yl)-(4-methoxyphenyl)methanone dimethyl acetal is used instead of 4-bromo-4'-(4-methoxyphenyl)benzophenone dimethyl acetal.

[Chem. 111]

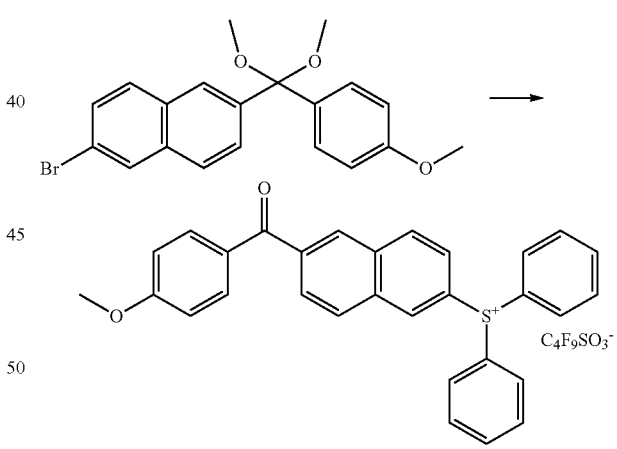

Synthesis Example 75

Synthesis of [6-(4-hydroxybenzoyl)naphthalen-2-yl]diphenylsulfonium-nonafluorobutanesulfonate

[6-(4-Hydroxybenzoyl) naphthalen-2-yl]diphenylsulfonium-nonafluorobutanesulfonate (3.8 g) is obtained in the same procedure as Synthesis Example 70 except that [6-(4-methoxybenzoyl) naphthalen-2-yl]diphenylsulfonium-nonafluorobutanesulfonate is used instead of [4-(4'-methoxybiphenyl-4-carbonyl)phenyl-diphenylsulfonium-nonafluorobutanesulfonate.

[Chem. 112]

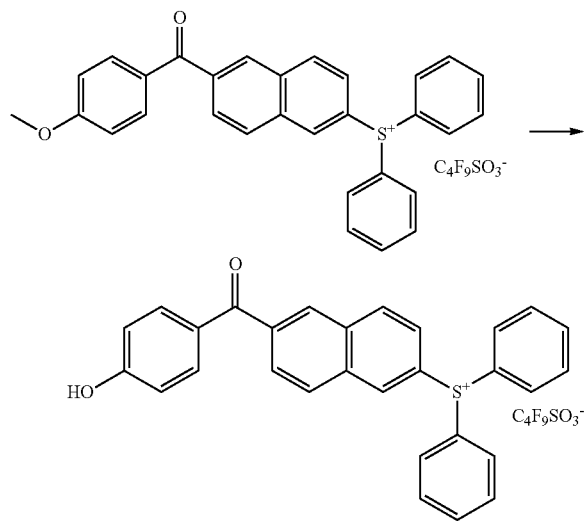

Synthesis Example 76

Synthesis of {6-[dimethoxy-(4-methoxyphenyl)methyl]naphthalen-2-yl}diphenylsulfonium-nonafluorobutanesulfonate (Sulfonium Salt 23)

{6-[Dimethoxy-(4-methoxyphenyl)methyl]naphthalen-2-yl}diphenylsulfonium-nonafluorobutanesulfonate (3.6 g) is obtained in the same procedure as Synthesis Example 71 except that [6-(4-hydroxybenzoyl)naphthalen-2-yl]diphenylsulfonium-nonafluorobutanesulfonate is used instead of {4-[(4'-hydroxybiphenyl-4-yl)dimethoxymethyl]-phenyl}-diphenylsulfonium-nonafluorobutanesulfonate.

[Chem. 113]

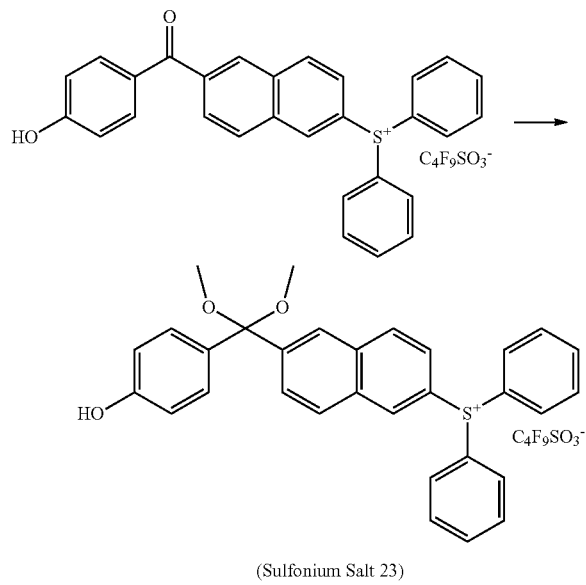

(Sulfonium Salt 23)

<Synthesis of Polymer A>

Synthesis Example 50

Synthesis of Polymer A

Polyhydroxystyrene (8.0 g) with weight-average molecular weight of 8000 and 35% by mass of aqueous solution (0.010 g) of hydrochloric acid are dissolved in dehydrated dioxane (28 g). Cyclohexyl vinyl ether (2.73 g) is dissolved in dehydrated dioxane (2.80 g), and a mixture is added dropwise to the solution of polyhydroxystyrene over 30 minutes. After dropwise addition, a mixture is set to 40° C., and stirred for 2 hours. After stirring, a mixture is cooled, and then dimethylaminopyridine (0.014 g) is added thereto. Thereafter, an obtained solution is added dropwise to pure water (260 g) to precipitate a polymer. The precipitated polymer is separated by filtration under reduced pressure to obtain a solid, the solid is washed twice with pure water (300 g), and then dried under vacuum to obtain Polymer A (9.2 g), represented below, as a white solid. A monomer ratio of unit of the polymer in the present invention is not limited to the below.

[Chem. 114]

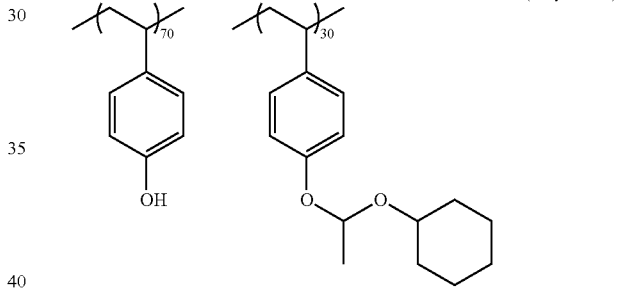

(Polymer A)

<Synthesis of Polymer C>

Synthesis Example 51

Synthesis of Polymer B

Acetoxystyrene (7.0 g), t-butyl methacrylate (3.1 g), butyl mercaptan (0.022 g) and dimethyl-2,2'-azobis(2-methylpropionate) (AIBN) (0.40 g) are dissolved in tetrahydrofuran (THF) (35 g), and a mixture is deoxygenated. A deoxygenated mixture is added dropwise over 4 hours to THF (20 g) which is set to reflux temperature under nitrogen flow in advance. After dropwise addition, a mixture is stirred for 2 hours, and then cooled to room temperature. A cooled mixture is added dropwise to a mixed solvent of hexane (149 g) and THF (12 g) to precipitate a polymer. The precipitated polymer is separated by filtration under reduced pressure to obtain a solid, the solid is washed with hexane (52 g), and then dried under vacuum to obtain Polymer B (10.3 g), represented by the following formula, as a white solid. A weight-average molecular weight calculated by polystyrene conversion using a gel permeation chromatography is 9200. A monomer ratio of unit of the polymer in the present invention is not limited to the below.

[Chem. 115]

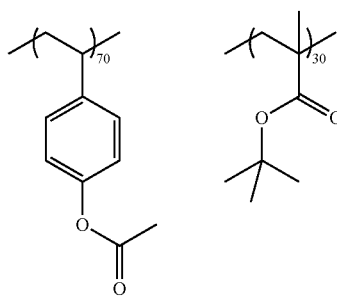

(Polymer B)

Synthesis Example 52

Synthesis of Polymer C

Polymer B (6.0 g), triethylamine (6.0 g), methanol (6.0 g) and pure water (1.5 g) are dissolved in propylene glycol monomethyl ether (30 g), and a mixture is stirred at reflux temperature for 6 hours. Then, a mixture is cooled to 25° C., and an obtained solution is added dropwise to a mixed liquid of acetone (30 g) and pure water (30 g) to precipitate a polymer. The precipitated polymer is separated by filtration under reduced pressure to obtain a solid, the solid is washed twice with pure water (30 g), and then dried under vacuum to obtain Polymer C (4.3 g), represented by the following formula, as a white solid. A weight-average molecular weight calculated by polystyrene conversion using a gel permeation chromatography is 9100. A monomer ratio of unit of the polymer in the present invention is not limited to the below.

[Chem. 116]

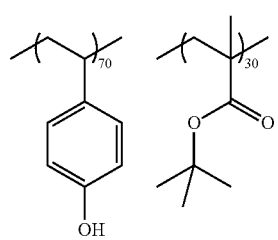

(Polymer C)

<Synthesis of Polymer D>

Synthesis Example 53

Synthesis of Polymer D

α-Methacryloxy-γ-butyrolactone (5.0 g), 2-methyladamantane-2-methacrylate (6.0 g), 3-hydroxyadamantane-1-methacrylate (4.3 g) and dimethyl-2,2'-azobis(2-methylpropionate) (0.51 g) are dissolved in propylene glycol-1-monomethyl ether acetate (PGMEA) (26 g), and a mixture is deoxygenated. A deoxygenated mixture is added dropwise over 4 hours to PGMEA (7.5 g) which is heated to 85° C. in advance. A mixture is stirred for 2 hours, and then cooled. After cooling, a mixture is added dropwise to hexane (180 g) to reprecipitate. A reprecipitated solid is filtered, dispersion-washed with hexane (70 g), filtered again, and then dried under vacuum to obtain Polymer D (8.5 g), represented by the following formula, as a compound to react with an acid. A monomer ratio of unit of the polymer in the present invention is not limited to the below.

[Chem. 117]

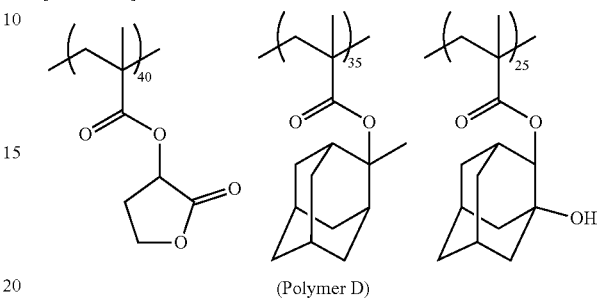

(Polymer D)

<Synthesis of Polymer F>

Synthesis Example 54

Synthesis of Polymer E

Polymer E (10.1 g), represented by the following formula, is obtained in the same procedure as Synthesis Example 51 except that p-t-butoxystyrene is used instead of t-butyl methacrylate. A monomer ratio of unit of the polymer in the present invention is not limited to the below.

[Chem. 118]

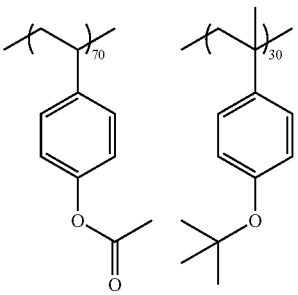

(Polymer E)

Synthesis Example 55

Synthesis of Polymer F

Polymer F (4.1 g), represented by the following formula, is obtained in the same procedure as Synthesis Example 52 except that Polymer E is used instead of Polymer B. A monomer ratio of unit of the polymer in the present invention is not limited to the below.

[Chem. 119]

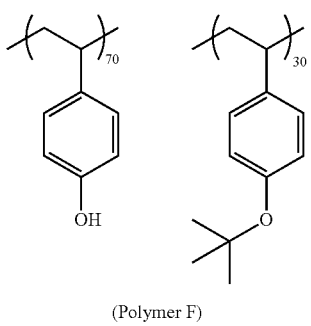

(Polymer F)

<Synthesis of Polymer G>

Synthesis Example 56

Synthesis of Polymer G

Polymer G (8.0 g), represented by the following formula, is obtained in the same procedure as Synthesis Example 53 except that 5-methacryloyloxynorbornane 2,6-lactone (5.5 g), 4-(1-ethoxyethoxy)phenyl methacrylate (6.2 g) and 4-hydroxyphenyl methacrylate (4.4 g) are used as monomers. A monomer ratio of unit of the polymer in the present invention is not limited to the below.

[Chem. 120]

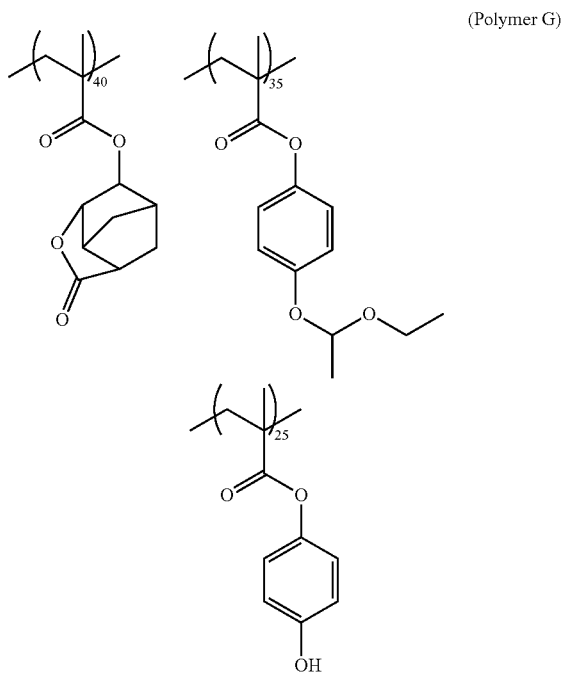

(Polymer G)

<Synthesis of Polymer I>

Synthesis Example 57

Synthesis of Polymer H

Polymer H (10.5 g), represented by the following formula, is obtained in the same procedure as Synthesis Example 51 except that 1-acetoxy-4-vinylnaphthalene is used instead of acetoxystyrene and 1-(2-tetrahydropyranyloxy)-4-vinylnaphthalene is used instead of t-butyl methacrylate. A monomer ratio of unit of the polymer in the present invention is not limited to the below.

[Chem. 121]

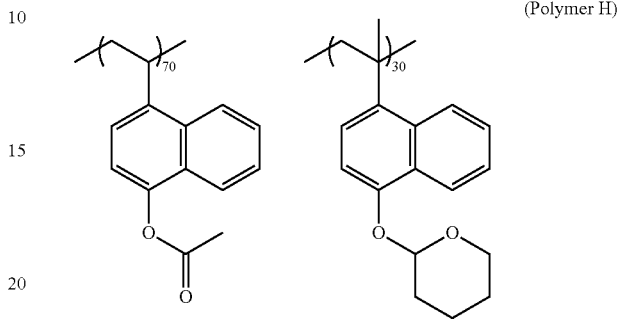

(Polymer H)

Synthesis Example 58

Synthesis of Polymer I

Polymer I (4.3 g), represented by the following formula, is obtained in the same procedure as Synthesis Example 52 except that Polymer H is used instead of Polymer B. A ratio of monomer unit of the polymer is not limited to the below.

[Chem. 122]

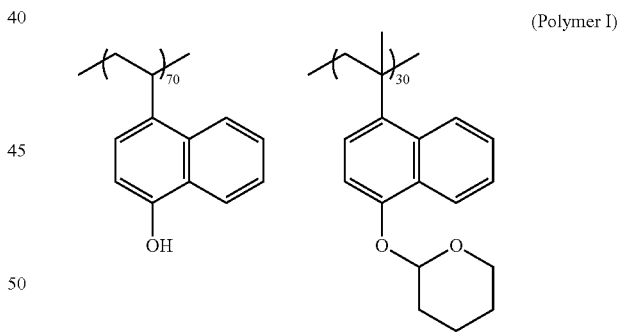

(Polymer I)

<Synthesis of Polymer J>

Synthesis Example 59

Synthesis of Polymer J

Polymer J (8.0 g), represented by the following formula, is obtained in the same procedure as Synthesis Example 53 except that 2-methacryloyloxy-1,3-propanesultone is used instead of α-methacryloxy-γ-butyrolactone. A monomer ratio of unit of the polymer in the present invention is not limited to the below.

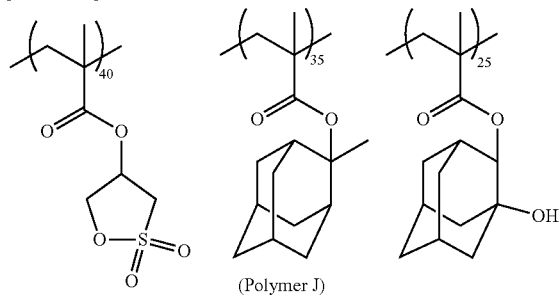

(Polymer J)

<Synthesis of Polymer K>

Synthesis Example 60

Synthesis of Polymer K

Polymer K (8.2 g), represented by the following formula, is obtained in the same procedure as Synthesis Example 53 except that 2-methacryloyloxy-1,3-propanesultone is used instead of α-methacryloxy-γ-butyrolactone and 1-ethoxyethyl methacrylate is used instead of 2-methyladamantane-2-methacrylate. A monomer ratio of unit of the polymer in the present invention is not limited to the below.

[Chem. 124]

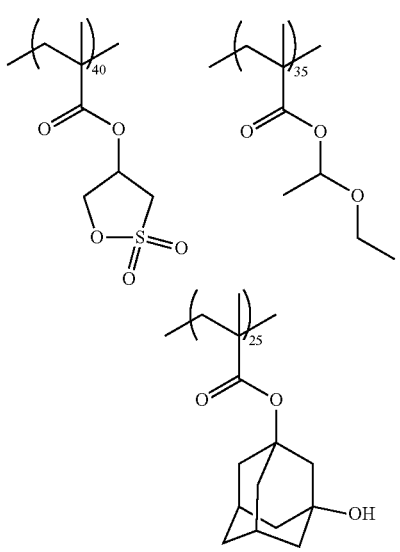

(Polymer K)

<Synthesis of Polymer L>

Synthesis Example 61

Synthesis of Polymer L

Polymer L (8.0 g), represented by the following formula, is obtained in the same procedure as Synthesis Example 53 except that 5-methacryloyloxynorbornane 2,6-sultone (7.2 g), 2-(1-ethoxyethoxy)-6-vinylnaphthalene (5.9 g) and 2-hydroxy-6-vinylnaphthalene (3.0 g) are used as polymers. A monomer ratio of unit of the polymer in the present invention is not limited to the below.

[Chem. 125]

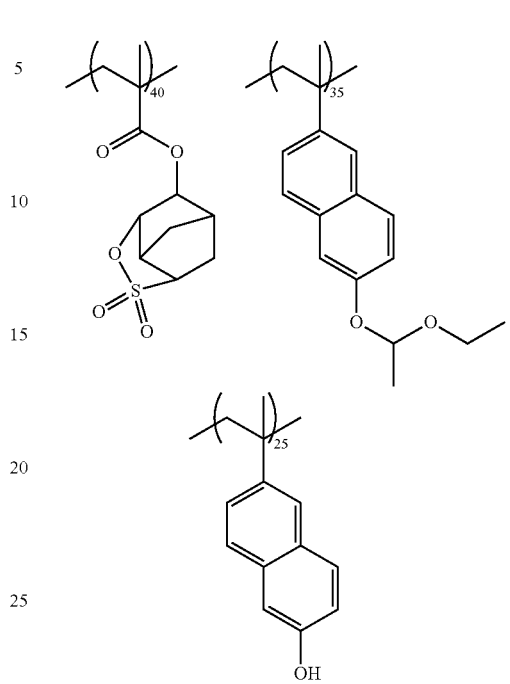

(Polymer L)

<Synthesis of Polymer M>

Synthesis Example 62

Synthesis of Polymer M

Polymer M (7.8 g), represented by the following formula, is obtained in the same procedure as Synthesis Example 53 except that Sulfonium Salt 16 (4.7 g) obtained in Synthesis Example 49, 5-methacryloyloxynorbornane 2,6-lactone (3.9 g), 4-(1-ethoxyethoxy)phenyl methacrylate (4.2 g) and 4-hydroxyphenyl methacrylate (3.2 g) are used as polymers. A monomer ratio of unit of the polymer in the present invention is not limited to the below.

[Chem. 126]

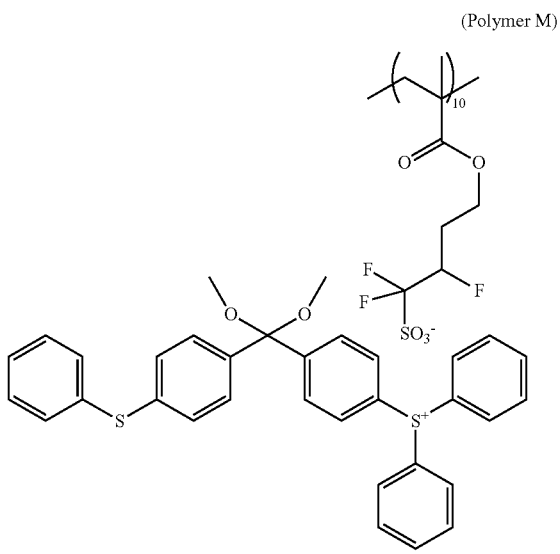

(Polymer M)

-continued

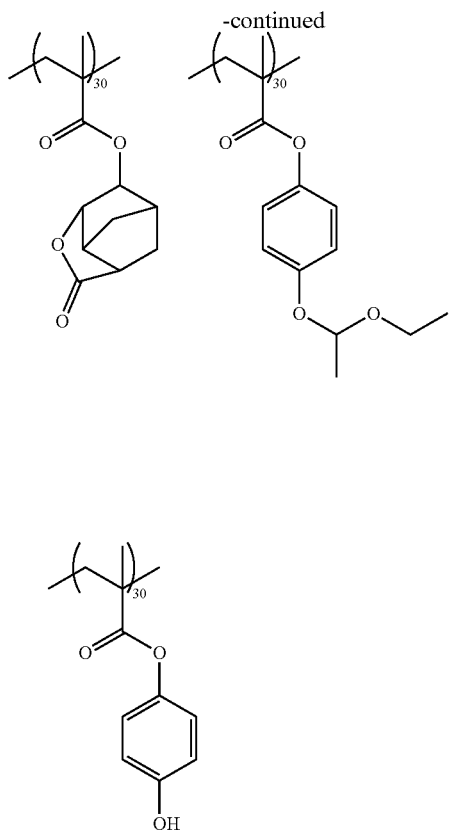

Examples 1 to 32 and Comparative Examples 1 to 6

<Evaluation of Electron Beam Sensitivity 1>

Each sample was prepared as follows. To cyclohexanone (3000 mg), any one of resin (500 mg) selected from Polymers A, C and D, each compound (0.036 mmol) appropriately selected solely or plurally from a photoacid generator (PAG) and a sensitizer compound, and an acid-diffusion controller (0.0012 mmol) were added in the ratio, to prepare Sample.

As the photoacid generator (PAG), Sulfonium Salts 1 to 23, Sulfonium Salt 24 represented below and Iodonium Salts 1 to 2 were used. As the sensitizer compound, Sensitizer Compound 1 and Comparative Sensitizer Compounds 1' to 2' represented below were used.

Sensitizer Compound 1 was synthesized as follows. 4-Methylsulfanyl-4'-phenylsulfanylbenzophenone (5.0 g) obtained in Synthesis Example 2, sulfuric acid (47 mg), and trimethyl orthoformate (13.5 g) are dissolved in methanol (12.5 g), and a mixture is stirred at reflux temperature for 3 hours. Then, a mixture is cooled to room temperature, 5% by mass of aqueous solution (50 g) of sodium hydrogen carbonate is added thereto, a mixture is further stirred for 10 minutes, and a precipitated crystal is filtrated. The crystal is recovered, re-dissolved in ethyl acetate (50 g), and a solution is washed with water. Thereafter, ethyl acetate is evaporated to obtain 4-methylsulfanyl-4'-phenylsulfanylbenzophenone dimethyl acetal (3.1 g).

[Chem. 127]

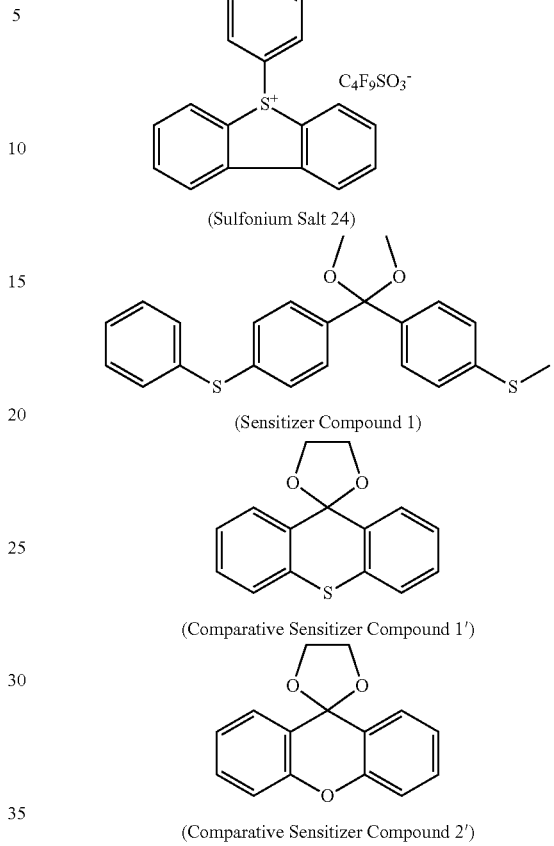

Evaluation of electron beam sensitivity is performed as follows. The resist composition sample 1 is spin-coated on a silicon wafer modified with hexamethylenedisilazane in advance. A spin-coated sample is prebaked on a hot plate at 110° C. for 1 minute to obtain a substrate on which a coating film having a thickness of 200 nm forms. To the coating film on the substrate, a line and space pattern of 200 nm is drawn by an electron beam of 30 keV using an electron beam lithography system. After irradiation with the electron beam, the entire surface of the substrate is exposed with exposure dose of 500 mJ/cm² using a UV exposure system, and then the substrate was heated on a hot plate at 110° C. for 1 minute. The substrate is developed with a developing solution, product name: NMD-3, 2.38% by mass of aqueous solution of tetramethylammonium hydroxide, manufactured by Tokyo Ohka Kogyo Co., Ltd., for 1 minute, and then rinsed with pure water to obtain a line and space pattern of 200 nm. An irradiation dose of the electron beam at this time is defined as $E_{size}$ [μC/cm²], and a sensitivity to the irradiation with the electron beam is evaluated. In addition, the obtained fine pattern is observed to measure LWR. The sensitivity evaluation and LWR measurement are also performed on the other samples in the same procedure as above. The sample compositions and results are described in Tables 1 to 3.

In Table 1, sensitivity and LWR of each sample of Examples 1 to 17 and Comparative Example 2 were calculated as relative values with sensitivity of sample of Comparative Sample 1 being 100 and with LWR of that being 1, and Sulfonium Salt 24 and Comparative Sensitizer Compound 1' being added to Comparative Sample 1. The smaller a value of sensitivity and LWR, the more effective.

In Table 2, evaluation results of samples of Examples 18 to 24 and Comparative Example 4 were calculated as relative values with sensitivity of Comparative Example 3 being 100 and with LWR of that being 1.

In Table 3, evaluation results of samples of Examples 25 to 32 and Comparative Example 6 were calculated as relative value, with sensitivity of Comparative Example 5 being 100 and with LWR of that being 1.

TABLE 1

| | Resist Composition | | | Sensitivity ($E_{size}$) | LWR |
|---|---|---|---|---|---|
| | Copolymer | Photoacid Generator | Sensitizer Compound | (Rel.) | (Rel.) |
| Example 1 | Polymer A | Sulfonium Salt 1 | Sulfonium Salt 24 | — | 75 | 0.95 |
| Example 2 | Polymer A | Sulfonium Salt 7 | Sulfonium Salt 24 | — | 60 | 0.95 |
| Example 3 | Polymer A | Sulfonium Salt 9 | Sulfonium Salt 24 | — | 55 | 0.95 |
| Example 4 | Polymer A | Sulfonium Salt 11 | Sulfonium Salt 24 | — | 70 | 0.98 |
| Example 5 | Polymer A | Sulfonium Salt 12 | Sulfonium Salt 24 | — | 53 | 0.98 |
| Example 6 | Polymer A | Iodonium Salt 1 | Sulfonium Salt 24 | — | 53 | 0.98 |
| Example 7 | Polymer A | Sulfonium Salt 1 | — | — | 85 | 0.93 |
| Example 8 | Polymer A | Sulfonium Salt 7 | — | — | 70 | 0.93 |
| Example 9 | Polymer A | Sulfonium Salt 9 | — | — | 65 | 0.93 |
| Example 10 | Polymer A | Sulfonium Salt 11 | — | — | 80 | 0.95 |
| Example 11 | Polymer A | Sulfonium Salt 12 | — | — | 60 | 0.95 |
| Example 12 | Polymer A | Iodonium Salt 1 | — | — | 63 | 0.98 |
| Example 13 | Polymer A | Sulfonium Salt 9 | — | Sensitizer Compound 1 | 58 | 0.95 |
| Example 14 | Polymer A | Iodonium Salt 1 | — | Sensitizer Compound 1 | 55 | 0.99 |
| Example 15 | Polymer A | Sulfonium Salt 17 | — | — | 68 | 0.93 |
| Example 16 | Polymer A | Sulfonium Salt 22 | — | — | 86 | 0.97 |
| Example 17 | Polymer A | Sulfonium Salt 23 | — | — | 62 | 0.93 |
| Comparative Example 1 | Polymer A | — | Sulfonium Salt 24 | Comparative Sensitizer Compound 1' | 100 | 1 |
| Comparative Example 2 | Polymer A | — | Sulfonium Salt 24 | Comparative Sensitizer Compound 2' | 140 | 1 |

TABLE 2

| | Resist Composition | | | Sensitivity ($E_{size}$) | LWR |
|---|---|---|---|---|---|
| | Copolymer | Photoacid Generator | Sensitizer Compound | (Rel.) | (Rel.) |
| Example 18 | Polymer C | Sulfonium Salt 1 | Sulfonium Salt 24 | — | 75 | 0.95 |
| Example 19 | Polymer C | Sulfonium Salt 2 | Sulfonium Salt 24 | — | 80 | 0.95 |
| Example 20 | Polymer C | Sulfonium Salt 3 | Sulfonium Salt 24 | — | 78 | 0.88 |
| Example 21 | Polymer C | Sulfonium Salt 9 | — | — | 65 | 0.93 |
| Example 22 | Polymer C | Sulfonium Salt 13 | — | — | 70 | 0.95 |
| Example 23 | Polymer C | Sulfonium Salt 18 | — | — | 63 | 0.98 |
| Example 24 | Polymer C | Sulfonium Salt 20 | — | — | 73 | 0.97 |
| Comparative Example 3 | Polymer C | — | Sulfonium Salt 24 | Comparative Sensitizer Compound 1' | 100 | 1 |

TABLE 3

| | Resist Composition | | | Sensitivity ($E_{size}$) | LWR |
|---|---|---|---|---|---|
| | Copolymer | Photoacid Generator | Sensitizer Compound | (Rel.) | (Rel.) |
| Example 25 | Polymer D | Sulfonium Salt 1 | Sulfonium Salt 24 | — | 75 | 0.95 |
| Example 26 | Polymer D | Sulfonium Salt 6 | Sulfonium Salt 24 | — | 83 | 0.95 |
| Example 27 | Polymer D | Sulfonium Salt 8 | — | — | 90 | 0.93 |
| Example 28 | Polymer D | Sulfonium Salt 9 | — | — | 65 | 0.93 |
| Example 29 | Polymer D | Sulfonium Salt 14 | — | — | 60 | 0.98 |
| Example 30 | Polymer D | Sulfonium Salt 19 | — | — | 63 | 0.95 |
| Example 31 | Polymer D | Sulfonium Salt 21 | — | — | 62 | 0.98 |
| Example 32 | Polymer D | Sulfonium Salt 23 | — | — | 58 | 0.98 |

TABLE 3-continued

| | Resist Composition | | | Sensitivity ($E_{size}$) (Rel.) | LWR (Rel.) |
|---|---|---|---|---|---|
| | Copolymer | Photoacid Generator | Sensitizer Compound | | |
| Comparative Example 5 | Polymer D | — | Sulfonium Salt 24 | Comparative Sensitizer Compound 1' | 100 | 1 |
| Comparative Example 6 | Polymer D | — | Sulfonium Salt 24 | Comparative Sensitizer Compound 2' | 140 | 1 |

It is found that: the sensitivities of Examples 1 to 17, which are samples containing onium salts according to some embodiments of the present invention, are higher than those of Comparative Examples 1 and 2; the sensitivities of Examples 18 to 24 are higher than those of Comparative Examples 3 and 4; and the sensitivities of Examples 25 to 32 are higher than those of Comparative Examples 5 and 6, respectively.

The reason might be as follows. Deprotection of the acetal group occurs in the onium salt according to some embodiments of the present invention by an acid generated in the resist film by irradiation with the electron beam as the first active energy ray, and the onium salt becomes a ketone derivative. Since the ketone derivative has absorption in UV as the second active energy ray, it can directly generate an acid by excitation by irradiation with UV. On the other hand, in Comparative Examples 1 to 6, a reaction involving electron transfer such as photoinduced electron transfer reaction like photosensitization is utilized. That is, it is assumed that since a sensitization reaction between molecules is utilized, the sensitivity is not good and decreases compared with the case when the acid is directly generated by excitation.

Furthermore, by using the onium salt according to some embodiments of the present invention, since acid diffusion involving electron transfer does not occur in the acid generation by irradiation with the second active energy ray, LWR can be suppressed as compared with Comparative Examples 1 to 6 utilizing the sensitization reaction between molecules.

The reason why the sensitivities of Example 13 and Example 14 become higher than that of Example 9 and Example 12 respectively might be as follows. In Example 13 and Example 14, at the time of irradiation with the second active energy ray, an acid is generated by the excitation of the ketone derivative having the absorption in the second active energy ray, and then an acid is generated by photosensitization occurring between the photosensitizer derived from the Sensitizing Compound 1 and Sulfonium Salt 9 or Iodonium Salt 1 having a high electron accepting property at the time of irradiation with the first active energy ray.

Examples 1, 33 to 39 and Comparative Examples 1 and 7 to 8

<Electron Beam Sensitivity Evaluation 2>

A line and space pattern of 200 nm is obtained by the same operation as in the above example <Electron Beam Sensitivity Evaluation 1>, except that PEB is performed for 30 seconds on a hot plate at 60 °C. after the electron beam irradiation. An irradiation dose of the electron beam at this time is defined as $E_{size}$ [μC/cm$^2$], and a sensitivity when PEB is performed after the irradiation with the electron beam is evaluated. In addition, the obtained pattern is observed to measure LWR. The sample compositions and results are described in Table 4. Sensitivity and LWR of each sample (Examples 33 to 39 and Comparative Example 8) were calculated as relative values with sensitivity of sample of Comparative Sample 7 being 100 and with LWR of that being 1, and Sulfonium Salt 24 and Comparative Sensitizer Compound 1' being added to Comparative Sample 7. In order to compare the effects of PEB, the sensitivity and LWR of the samples of Example 1 and Comparative Example 1 were calculated as relative values with the ones of Comparative Example 7, and evaluated. That is, in Table 4, in order to compare the effects of PEB, the evaluation of the Example 1, as evaluation of the sample in which Sulfonium Salt 1 and Sulfonium Salt 24 are added without PEB; and the evaluation of the Comparative Example 1 as evaluation of the sample in which Sulfonium Salt 24 and Comparative Sensitizing Compound 1' are added without PEB; are described.

The smaller a value of sensitivity and LWR, the more effective.

TABLE 4

| | Resist Composition | | | Sensitivity ($E_{size}$) (Rel.) | LWR (Rel.) |
|---|---|---|---|---|---|
| | Copolymer | Photoacid Generator | Sensitizer Compound | | |
| Example 33 | Polymer A | Sulfonium Salt 1 | Sulfonium Salt 24 | — | 75 | 0.95 |
| Example 34 | Polymer A | Sulfonium Salt 1 | — | — | 85 | 0.93 |
| Example 35 | Polymer A | Sulfonium Salt 7 | — | — | 70 | 0.93 |
| Example 36 | Polymer A | Sulfonium Salt 9 | — | — | 65 | 0.93 |
| Example 37 | Polymer A | Sulfonium Salt 12 | — | — | 60 | 0.95 |
| Example 38 | Polymer A | Sulfonium Salt 1 | — | — | 63 | 0.98 |
| Example 39 | Polymer A | Sulfonium Salt 7 | — | — | 78 | 0.90 |
| Comparative Example 7 | Polymer A | — | Sulfonium Salt 24 | Comparative Sensitizer Compound 1' | 100 | 1 |
| Comparative Example 8 | Polymer A | — | Sulfonium Salt 24 | Comparative Sensitizer Compound 2' | 140 | 1 |
| Example 1 | Polymer A | Sulfonium Salt 1 | Sulfonium Salt 24 | — | 90 | 0.93 |
| Comparative Example 1 | Polymer A | — | Sulfonium Salt 24 | Comparative Sensitizer Compound 1' | 120 | 0.98 |

Even when PEB is performed at 60 °C. after the irradiation with the electron beam in the pattern forming step, in Examples 33 to 39, which are samples containing the onium salts according to some embodiments of the present invention, the sensitivity is higher and the LWR can be suppressed like the Examples 1 to 32, more than that in Comparative Examples 7 and 8 utilizing the sensitization reaction between molecules. In addition, comparing Example 33, Example 1 and Comparative Example 1, it is assumed that since in Example 33, PEB after the irradiation with the electron beam diffuses the acid generated by the electron beam as the first active energy ray, more ketone derivatives having absorption in the second active energy ray are generated in the resist film, the sensitivity is improved as compared with Example 1 and Comparative Example 1, which do not have PEB step after the irradiation with the electron beam.

In Example 33, the LWR is somewhat deteriorated as compared with Example 1 due to the effect of acid diffusion by PEB, but since the acid diffusion involving electron transfer does not occur in the acid generation by the irradiation with the second energy ray, the LWR can be suppressed as compared with Comparative Example 1 in which the sensitization reaction is utilized.

The polymer A has a higher proportion, than the polymer C, of hydroxystyrene and its derivative, which having a lower ionization potential, than the polymer C, and the polymer A has slightly higher secondary electron generation efficiency than the polymer C, so that the acid generation efficiency is improved by the irradiation with the electron beam as the first active energy ray and activation energy of a reactive group to an acid is lower, and the deprotection reaction progresses efficiently. Therefore, comparing Example 35 and Example 39, the sensitivity of Example 35 is higher than that of Example 39.

Examples 40 to 44 and Comparative Example 9

<Electron Beam Sensitivity Evaluation 3>

A line and space pattern of 200 nm is obtained by the same operation as in the above example <Electron Beam Sensitivity Evaluation 2>. An irradiation dose of the electron beam at this time is defined as $E_{size}$ [μC/cm²], and a sensitivity when PEB is performed by the irradiation with the electron beam is evaluated. In addition, the obtained fine pattern is observed to measure LWR. The sample compositions and results are described in Table 5. Sensitivity and LWR of each sample (Examples 40 to 44) were calculated as relative values with sensitivity of sample of Comparative Sample 9 being 100 and with LWR of that being 1, and Sulfonium Salt 24 and Comparative Sensitizer Compound 1' being added to Comparative Sample 9.

The smaller a value of sensitivity and LWR, the more effective.

TABLE 5

| | Resist Composition | | | Sensitivity ($E_{size}$) (Rel.) | LWR (Rel.) |
|---|---|---|---|---|---|
| | Copolymer | Photoacid Generator | Sensitizer Compound | | |
| Example 40 | Polymer D | Sulfonium Salt 7 | — | — | 70 | 0.90 |
| Example 41 | Polymer J | Sulfonium Salt 7 | — | — | 65 | 0.93 |
| Example 42 | Polymer K | Sulfonium Salt 7 | — | — | 60 | 0.95 |
| Example 43 | Polymer G | Sulfonium Salt 7 | — | — | 63 | 0.98 |
| Example 44 | Polymer M | — | — | — | 58 | 0.85 |
| Comparative Example 9 | Polymer D | — | Sulfonium Salt 24 | Comparative Sensitizer Compound 1' | 100 | 1 |

In Examples 40 to 43, which are samples containing the onium salts according to some embodiments of the present invention, the sensitivity is higher and the LWR can be suppressed as in Examples 1 to 32 more than Comparative Example 9 utilizing a sensitization reaction between molecules. It is found that even when the onium salt of the present invention is contained in the polymer as in Example 44, the same function as the sample to which the onium salt is added can be obtained, so that the sensitivity is higher than Comparative Example 9 and the LWR can be suppressed.

Comparing Examples 40 to 42, it is assumed that by using a polymer containing a sultone compound as in Examples 41 and 42, an acid generated by decomposition of the sultone compound after irradiation with the electron beam as the first active energy ray contributes to deprotection reaction of the acetal of the onium salt according to some embodiments of the present invention. As a result, more ketone derivatives having absorption in the second active energy ray can be produced, so that the sensitivities of Examples 41 and 42 are higher than those of Example 40. Further, in Example 42, it is assumed that since the acid reactive compound is an acid dissociable protecting group having low activation energy, the acid generated by the decomposition of the sultone compound after the irradiation with the electron beam as the first active energy ray also contributes to polarity conversion by reaction with the acid reactive compound. Then, the solubility of the resin in the developing solution changes more. Therefore, the sensitivity of Examples 42 is higher than those of Example 41.

Comparing Examples 43 and 44, in Example 44, it is assumed since an anion moiety of the onium salt according to the present invention is copolymerized with a polymer, an acid generated upon irradiation with the electron beam as the first active energy ray and the second active energy ray hardly diffuse, and the LWR can be suppressed more than Example 43.

INDUSTRIAL APPLICABILITY

According to some embodiments of the present invention, a resin composition containing an onium salt can be provided. A structure of the onium salt changes to a ketone derivative by an active species generated by irradiation with a first active energy ray such as an electron beam or an extreme ultraviolet, and the ketone derivative generates an active species by irradiation with a second active energy ray.

By using the above resin composition, a resist composition having high sensitivity and excellent pattern characteristics such as LWR can be obtained.

The invention claimed is:

1. An onium salt represented by any one selected from a following general formula (1), a following general formula (2), a following general formula (11), and a following general formula (12),

[Chem. 1]

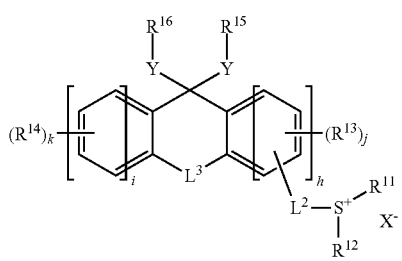
(1)

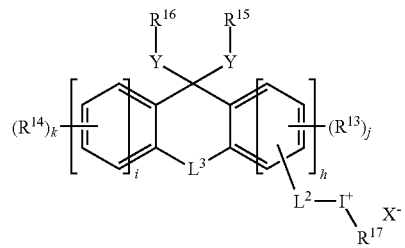
(2)

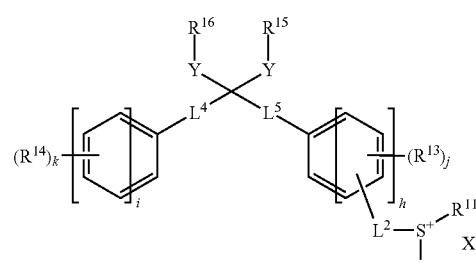
(11)

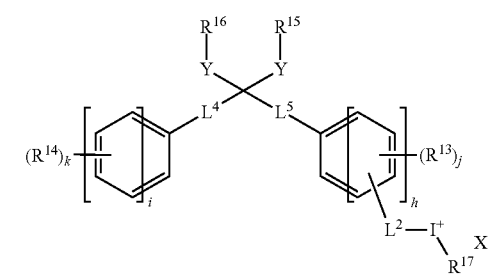
(12)

wherein:
in the general formula (1),
each of $R^{11}$ and $R^{12}$ is any one independently selected from the group consisting of: a linear, branched or cyclic alkyl group which may have a substituent (A), the alkyl group having 1 to 12 carbon atoms; a linear, branched or cyclic alkenyl group which may have the substituent (A), the alkenyl group having 1 to 12 carbon atoms; an aryl group which may have a substituent (B), the aryl group having 6 to 10 carbon atoms; and a heteroaryl group which may have the substituent (A), the heteroaryl group having 4 to 12 carbon atoms;
a number of carbon atoms of each of the alkyl group, the alkenyl group and the heteroaryl group does not include a number of carbon atoms of the substituent (A);
a number of carbon atoms of the aryl group does not include a number of carbon atoms of the substituent (B);
when the aryl group of $R^{11}$ and $R^{12}$ may have the substituent (B), the substituent (B) is selected from the group consisting of a hydroxy group, a cyano group, a mercapto group, a carboxy group, a carbonyl group, an alkoxy group (—OR), an acyl group (—COR), an alkoxycarbonyl group (—COOR), an amino group, an alkylamino group (—NHR), a dialkylamino group (—N(R)$_2$), a phosphino group, a silyl group, a halogen atom, a trialkylsilyl group (—Si—(R)$_3$); and a main chain of a polymer;
the R in the substituent (B) is the alkyl group having 1 to 20 carbon atoms;
when the alkyl group, the alkenyl group and the heteroaryl group may have the substituent (A), the substituent (A)

is selected from the group consisting of group (—OR), an acyl group (—COR), an alkoxycarbonyl group (—COOR), an aryl group (—Ar), an aryloxy group (—OAr), an amino group, an alkylamino group (—NHR), a dialkylamino group (—N(R)$_2$), an arylamino group (—NHAr), a diarylamino group (—N(Ar)$_2$), an N-alkyl-N-arylamino group (—NRAr), a phosphino group, a silyl group, a halogen atom, a trialkylsilyl group (—Si—(R)$_3$), a silyl group substituting at least one alkyl group of the trialkylsilyl group with Ar, an alkylsulfanyl group (—SR), an arylsulfanyl group (—SAr) and a main chain of a polymer;

the R in the substituent (A) is the alkyl group having 1 to 20 carbon atoms;

the Ar in the substituent (A) is the aryl group having 1 to 20 carbon atoms;

any two or more of $R^{11}$, $R^{12}$ and an aryl group bonded to a sulfonium group may be bonded each other directly with a single bond, or through any one selected from the group consisting of:

an oxygen atom; a sulfur atom; a nitrogen atom-containing group; and a methylene group to form a ring structure with a sulfur atom bonded to $R^{11}$, $R^{12}$ and the aryl group bonded to the sulfonium group are bonded;

at least one methylene group in $R^{11}$ and $R^{12}$ may be substituted with a divalent hetero atom-containing group;

each of $R^{13}$ and $R^{14}$ is any one independently selected from the group consisting of: an alkyl group; a hydroxy group; a mercapto group; an alkoxy group; an alkylcarbonyl group; an arylcarbonyl group; an alkoxycarbonyl group; an aryloxycarbonyl group; an arylsulfanylcarbonyl group; an arylsulfanyl group; an alkylsulfanyl group; an aryl group; a heteroaryl group; an aryloxy group; an alkylsulfinyl group; an arylsulfinyl group; an alkylsulfonyl group; an arylsulfonyl group; a (meth)acryloyloxy group; a hydroxy(poly)alkyleneoxy group; an amino group; a cyano group; a nitro group; and a halogen atom, where $R^{13}$ and $R^{14}$ have 1 to 12 carbon atoms when $R^{13}$ and $R^{14}$ have a carbon atom, and these groups may have the substituent (A);

the substituent (A) of $R^{13}$ and $R^{14}$ is the same as the substituent (A) of $R^{11}$ and $R^{12}$;

each of $R^{15}$ and $R^{16}$ is any one independently selected from the group consisting of: a linear, branched or cyclic alkyl group which may have the substituent (A), the alkyl group having 1 to 12 carbon atoms; a linear, branched or cyclic alkenyl group which may have the substituent (A), the alkenyl group having 1 to 12 carbon atoms; an aryl group which may have the substituent (A), the aryl group having 6 to 14 carbon atoms; and a heteroaryl group which may have the substituent (A), the heteroaryl group having 4 to 12 carbon atoms;

$R^{15}$ and $R^{16}$ may be bonded each other directly with a single bond or through any one selected from the group consisting of: an oxygen atom; a sulfur atom; and an alkylene group to form a ring structure;

at least one methylene group in $R^{15}$ and $R^{16}$ may be substituted with a divalent hetero atom-containing group;

the substituent (A) of $R^{15}$ and $R^{16}$ is the same as the substituent (A) of $R^{11}$ and $R^{12}$;

$L^2$ is any one selected from the group consisting of: a direct bond; a linear, branched or cyclic alkylene group having 1 to 12 carbon atoms; an alkenylene group having 1 to 12 carbon atoms; an arylene group having 6 to 14 carbon atoms; a heteroarylene group having 4 to 12 carbon atoms; and a group in which these groups are bonded through an oxygen atom, a sulfur atom or a nitrogen atom-containing group;

$L^3$ is selected from the group consisting of: a direct bond; a methylene group; a sulfur atom; a nitrogen atom-containing group; and an oxygen atom;

Y is an oxygen atom or a sulfur atom;

each of h and i is independently an integer of 1 to 3;

j is an integer of 0 to 4 when h is 1, 0 to 6 when h is 2, and 0 to 8 when h is 3;

k is an integer of 0 to 5 when i is 1, 0 to 7 when i is 2, and 0 to 9 when i is 3;

$X^-$ is a monovalent counter anion;

in the general formula (2), each of $R^{13}$ to $R^{16}$, $L^2$, $L^3$, Y, h to k and $X^-$ is independently selected from a same option as each of $R^{13}$ to $R^{16}$, $L^2$, $L^3$, Y, h to k and $X^-$ in the formula (1);

$R^{17}$ is any one selected from the group consisting of: an aryl group which may have the substituent (A); and a heteroaryl group which may have the substituent (A); and $R^{17}$ and an aryl group bonded to an iodonium group may be bonded each other to form a ring structure with an iodine atom bonded to $R^{17}$ and the aryl group bonded to the iodonium group;

in the general formula (11), each of $R^{11}$ to $R^{16}$, $L^2$, Y, h to k and $X^-$ is independently selected from a same option as each of $R^{11}$ to $R^{16}$, $L^2$, Y, h to k and $X^-$ in the formula (1); and each of $L^4$ and $L^5$ is any one independently selected from the group consisting of: a direct bond; an alkenylene group having 2 carbon atoms; an alkynylene group having 2 carbon atoms; and a carbonyl group;

in the general formula (12), each of $R^{13}$ to $R^{17}$, $L^2$, Y, h to k and $X^-$ is independently selected from a same option as each of $R^{13}$ to $R^{17}$, $L^2$, Y, h to k and $X^-$ in the formula (2); and each of $L^4$ and $L^5$ is any one independently selected from the group consisting of: a direct bond; an alkenylene group having 2 carbon atoms; an alkynylene group having 2 carbon atoms; and a carbonyl group.

2. The onium salt of claim 1, wherein the onium salt is represented by any one selected from the general formula (11) and the general formula (12).

3. The onium salt of claim 1, wherein the onium salt is represented by a following general formula (6),

[Chem. 2]

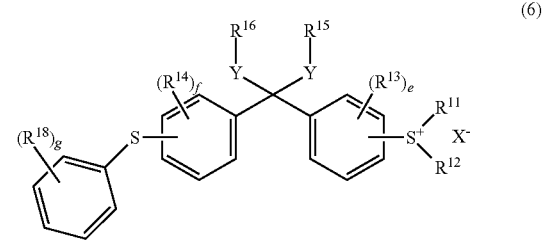

where:
in the general formula (6),
each of $R^{11}$ to $R^{16}$, $X^-$ and Y is independently selected from a same option as each of $R^{11}$ to $R^{16}$, $X^-$ and Y in the general formula (1);

$R^{18}$ is any one selected from the group consisting of: an alkyl group; a hydroxy group; a mercapto group; an alkoxy group; an alkylcarbonyl group; an arylcarbonyl group; an alkoxycarbonyl group; an aryloxycarbonyl group; an arylsulfanylcarbonyl group; an arylsulfanyl group; an alkylsulfanyl group; an aryl group; a heteroaryl group; an aryloxy group; an alkylsulfinyl group; an arylsulfinyl group; an alkylsulfonyl group; an arylsulfonyl group; a (meth)acryloyloxy group; a hydroxy(poly)alkyleneoxy group; an amino group; a cyano group; a nitro group; and a halogen atom, where $R^{18}$ has 1 to 12 carbon atoms when $R^{18}$ has a carbon atom;

e is an integer of 0 to 4;

f is an integer of 0 to 4; and g is an integer of 0 to 5.

4. A photoacid generator comprising at least the onium salt of claim 1.

5. A composition comprising: the photoacid generator of claim 4; and an acid reactive compound.

6. The composition of claim 5, further comprising an acid-diffusion controller.

7. The composition of claim 5, wherein the acid reactive compound is a resin (B) whose solubility in a developing solution changes by an acid, the resin (B) having at least one of units represented by following formulas (3a) to (3d),

[Chem. 3]

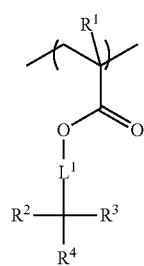
(3a)

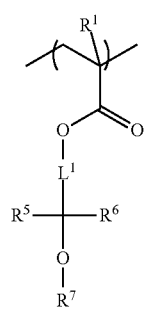
(3b)

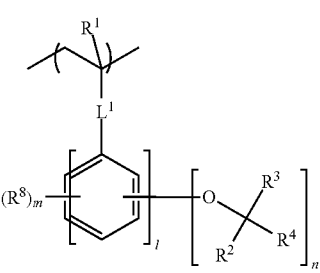
(3c)

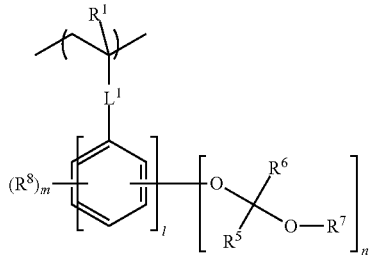
(3d)

where:

in the formulas (3a) to (3d), $R^1$ is any one selected from the group consisting of: a hydrogen atom; an alkyl group; and a halogenated alkyl group;

each of $R^2$ and $R^3$ is independently a linear, branched or cyclic alkyl group;

$R^4$ is a linear, branched or cyclic alkyl group which may have a substituent (C);

the substituent (C) is selected from the group consisting of a hydroxyl group, an alkoxy group, an oxo group, an amino group and an alkylamino group;

two or more of $R^2$, $R^3$ and $R^4$ may be bonded each other directly with a single bond or through any one selected from the group consisting of a methylene group to form a ring structure;

each of $R^5$ and $R^6$ is any one independently selected from the group consisting of: a hydrogen atom,; and a linear, branched or cyclic alkyl group;

$R^7$ is a linear, branched or cyclic alkyl group which may have the substituent (D);

the substituent (D) is selected from the group consisting of a hydroxyl group, an alkoxy group, an oxo group, an amino group and an alkylamino group;

two or more of $R^5$, $R^6$, and $R^7$ may be bonded to each other directly with a single bond or through any one selected from the group consisting of a methylene group to form a ring structure;

$L^1$ is any one selected from the group consisting of: a direct bond; a carbonyloxy group; a carbonylamino group; a linear, branched or cyclic alkylenecarbonyloxy group; and a linear, branched or cyclic alkylenecarbonylamino group;

each of $R^8$ is any one independently selected from the group consisting of: an alkyl group; a hydroxy group; an alkoxy group; an alkylcarbonyl group; an alkylsulfanyl group; an alkylsulfinyl group; an alkylsulfonyl group; an amino group; a cyano group; a nitro group; and a halogen atom;

l is an integer of 1 to 2;

m is an integer of 0 to 4 when l is 1, and an integer of 0 to 6 when l is 2;

n is an integer of 1 to 5 when l is 1, and an integer of 1 to 7 when l is 2; and m+n is 1 to 5 when l is 1, and 1 to 7 when l is 2.

8. The composition of claim 7, wherein:

the resin (B) has at least one of units represented by following general formulas (4a) to (4b); or the composition further comprises a resin (C) having at least one of units represented by following general formulas (4a) to (4b),

[Chem. 4]

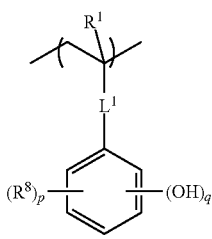
(4a)

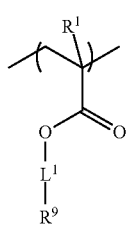
(4b)

where:

in the general formulas (4a) and (4b), each of $R^1$, $R^8$ and $L^1$ is independently selected from a same option as each of $R^1$, $R^8$ and $L^1$ in the formulas (3a)-(3d);

$R^9$ is a cyclic group having at least one selected from the group consisting of —C(O)—O—, —SO$_2$— and —O—SO$_2$—;

p is an integer of 0 to 4; and q is an integer of 1 to 5.

9. The composition of claim 5, wherein the photoacid generator is an acid-generator unit-containing resin in which X⁻ in the onium salt has a unit represented by a following general formula (5),

[Chem. 5]

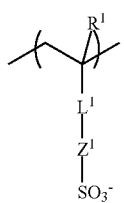
(5)

where:

in the general formula (5), $R^1$ is any one selected from the group consisting of: a hydrogen atom; an alkyl group; and a halogenated alkyl group; $L^1$ is any one selected from the group consisting of: a direct bond; a carbonyloxy group; a carbonylamino group; a linear, branched or cyclic alkylene carbonyloxy group; and a linear, branched or cyclic alkylenecarbonylamino group;

$Z^1$ is any one selected from the group consisting of: a linear or branched alkylene group having 1 to 12 carbon atoms; a linear or branched alkenylene group having 1 to 12 carbon atoms; and an arylene group having 6 to 14 carbon atoms;

a part or all of hydrogen atoms of the alkylene group, the alkenylene group and the arylene group may be substituted with a fluorine atom; and at least one methylene group in the alkylene group, the alkenylene group and the arylene group may be substituted with a divalent hetero atom-containing group.

10. A method of manufacturing a device, comprising:

forming a resist film by applying the composition of claim 5 to a substrate;

irradiating the resist film with a first active energy ray;

irradiating a resist film after irradiating with the first active energy ray, with a second active energy ray; and obtaining a pattern by developing a resist film after irradiating with the second active energy ray.

11. The method of claim 10, wherein a wavelength of the first active energy ray is shorter than a wavelength of the second active energy ray.

12. The method of claim 11, wherein the first active energy ray is an electron beam or an extreme ultraviolet.

13. The method of claim 10, further comprising heating with a heating wire or a laser between irradiating with the first active energy ray and irradiating with the second active energy ray.

14. The method of claim 10, wherein the method further comprises:

generating a first active species from the composition in the resist film by irradiating with the first active energy ray;

changing a structure of the photoacid generator by the first active species; and generating a second active species from a structure-changed photoacid generator by irradiating with the second active energy ray.

15. The method of claim 14, wherein the structure-changed photoacid generator is a ketone derivative.

* * * * *